(12) United States Patent
Angell et al.

(10) Patent No.: US 11,434,201 B2
(45) Date of Patent: Sep. 6, 2022

(54) PROCESSES FOR PREPARING PYRROLIDINE COMPOUNDS

(71) Applicant: Vertex Pharmaceuticals Incorporated, Boston, MA (US)

(72) Inventors: Paul T. Angell, Carlsbad, CA (US); Robert M. Hughes, San Diego, CA (US); Berenice Lewandowski, Braintree, MA (US); Benjamin J. Littler, Carlsbad, CA (US); William A. Nugent, Noblesville, IN (US); David Smith, Newton, MA (US); John Studley, Witney (GB)

(73) Assignee: Vertex Pharmaceuticals Incorporated, Boston, MA (US)

( * ) Notice: Subject to any disclaimer, the term of this patent is extended or adjusted under 35 U.S.C. 154(b) by 292 days.

(21) Appl. No.: 16/635,346

(22) PCT Filed: Aug. 2, 2018

(86) PCT No.: PCT/US2018/044963
§ 371 (c)(1),
(2) Date: Jan. 30, 2020

(87) PCT Pub. No.: WO2019/028228
PCT Pub. Date: Feb. 7, 2019

(65) Prior Publication Data
US 2020/0369608 A1    Nov. 26, 2020

(51) Int. Cl.
*C07D 207/06* (2006.01)
(52) U.S. Cl.
CPC .................. *C07D 207/06* (2013.01)
(58) Field of Classification Search
CPC . C07D 207/06; C07D 207/263; C07D 207/12
See application file for complete search history.

(56) References Cited

U.S. PATENT DOCUMENTS

| | | | |
|---|---|---|---|
| 5,410,061 A | 4/1995 | Gilmore et al. | |
| 6,441,004 B1 | 8/2002 | Faull et al. | |
| 6,787,651 B2 | 9/2004 | Stolle et al. | |
| 6,949,572 B2 | 9/2005 | Bertinato et al. | |
| 6,979,692 B2 | 12/2005 | Bertinato et al. | |
| 7,368,573 B2 | 5/2008 | Bertinato et al. | |
| 8,058,299 B2 | 11/2011 | Bolin et al. | |
| 9,663,508 B2 | 5/2017 | Bregman et al. | |
| 9,782,408 B2 | 10/2017 | Miller et al. | |
| 9,981,910 B2 | 5/2018 | Altenbach et al. | |
| 10,118,916 B2 | 11/2018 | Altenbach et al. | |
| 10,131,670 B2 | 11/2018 | Strohbach et al. | |
| 10,138,227 B2 | 11/2018 | Altenbach et al. | |
| 10,208,053 B2 | 2/2019 | Strohbach et al. | |
| 10,258,624 B2 | 4/2019 | Miller et al. | |
| 10,570,115 B2 | 2/2020 | Alcacio et al. | |
| 10,654,829 B2 | 5/2020 | Dhamankar et al. | |
| 10,793,547 B2 | 10/2020 | Abela et al. | |
| 2002/0055631 A1 | 5/2002 | Augeri et al. | |
| 2002/0086887 A1 | 7/2002 | Augeri et al. | |
| 2005/0171185 A1 | 8/2005 | Yamasaki et al. | |
| 2005/0197376 A1 | 9/2005 | Kayakiri et al. | |
| 2007/0105833 A1 | 5/2007 | Ruah et al. | |
| 2010/0227888 A1 | 9/2010 | Ruah et al. | |
| 2011/0165118 A1 | 7/2011 | Chan et al. | |
| 2013/0072483 A1 | 3/2013 | Wenge et al. | |
| 2013/0267493 A1 | 10/2013 | Bhattacharya et al. | |
| 2013/0317000 A1 | 11/2013 | Chowdhury et al. | |
| 2013/0317001 A1 | 11/2013 | Andrez et al. | |
| 2014/0080825 A1 | 3/2014 | Hadida-Ruah et al. | |
| 2014/0296200 A1 | 10/2014 | Brown et al. | |
| 2015/0320736 A1 | 11/2015 | Phenix et al. | |

(Continued)

FOREIGN PATENT DOCUMENTS

| | | |
|---|---|---|
| AU | 2013231151 A1 | 10/2013 |
| AU | 2013270464 A1 | 1/2014 |
| CA | 2145473 A1 | 9/1995 |
| EP | 0 194 599 A2 | 9/1986 |
| EP | 0 673 930 A1 | 9/1995 |
| EP | 1 318 978 B1 | 2/2006 |
| JP | 10-114654 A | 5/1998 |
| WO | WO 96/03380 A1 | 2/1996 |
| WO | WO 96/22022 A1 | 7/1996 |
| WO | WO 97/18712 A1 | 5/1997 |
| WO | WO 97/22586 A1 | 6/1997 |
| WO | WO 98/31226 A1 | 7/1998 |
| WO | WO 99/16744 A1 | 4/1999 |
| WO | WO 99/37153 A1 | 7/1999 |
| WO | WO 99/41238 A1 | 8/1999 |
| WO | WO 00/76969 A1 | 12/2000 |

(Continued)

OTHER PUBLICATIONS

John T. Lai et al. (J. Org. Chem. 1980, vol. 45 (8); p. 1513-1514).*

(Continued)

*Primary Examiner* — Valerie Rodriguez-Garcia
(74) *Attorney, Agent, or Firm* — Finnegan, Henderson, Farabow, Garrett & Dunner LLP

(57) ABSTRACT

Processes for preparing 5,5-dimethyl-3-methylenepyrrolidin-2-one, (S)-3,5,5-trimethylpyrrolidine-2-one, (R)-3,5,5-trimethylpyrrolidine-2-one, (S)-2,4,4-trimethylpyrrolidine, and (R)-2,4,4-trimethylpyrrolidine, and their salt forms are disclosed.

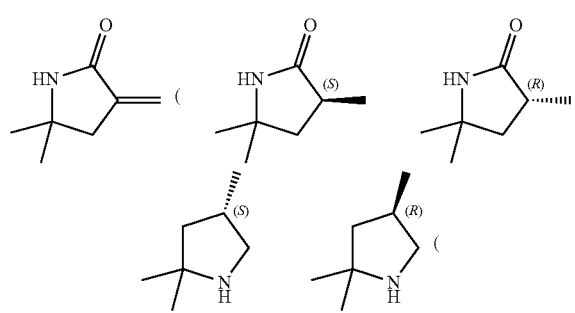

22 Claims, No Drawings

(56) References Cited

U.S. PATENT DOCUMENTS

| | | |
|---|---|---|
| 2015/0322002 A1 | 11/2015 | Dehnhardt et al. |
| 2018/0099932 A1 | 4/2018 | Altenbach et al. |
| 2018/0141954 A1 | 5/2018 | Strohbach et al. |
| 2018/0170938 A1 | 6/2018 | Strohbach et al. |
| 2018/0244611 A1 | 8/2018 | Altenbach et al. |
| 2018/0244640 A1 | 8/2018 | Altenbach et al. |
| 2019/0055220 A1 | 2/2019 | Bear et al. |
| 2019/0077784 A1 | 3/2019 | Altenbach et al. |
| 2019/0153000 A1 | 5/2019 | Munoz et al. |
| 2019/0240197 A1 | 8/2019 | Chu et al. |
| 2019/0269683 A1 | 9/2019 | Miller et al. |
| 2020/0138798 A1 | 5/2020 | Chen et al. |
| 2020/0283405 A1 | 9/2020 | Alcacio et al. |

FOREIGN PATENT DOCUMENTS

| | | |
|---|---|---|
| WO | WO 01/08487 A1 | 2/2001 |
| WO | WO 01/15533 A1 | 3/2001 |
| WO | WO 01/39597 A2 | 6/2001 |
| WO | WO 02/15902 A1 | 2/2002 |
| WO | WO 02/24636 A2 | 3/2002 |
| WO | WO 02/30895 A1 | 4/2002 |
| WO | WO 02/085120 A2 | 10/2002 |
| WO | WO 02/096883 A1 | 12/2002 |
| WO | WO 03/002533 A1 | 1/2003 |
| WO | WO 03/022050 A1 | 3/2003 |
| WO | WO 03/028458 A1 | 4/2003 |
| WO | WO 03/043423 A1 | 5/2003 |
| WO | WO 03/043655 A1 | 5/2003 |
| WO | WO 03/101959 A1 | 12/2003 |
| WO | WO 03/103394 A2 | 12/2003 |
| WO | WO 2004/021788 A1 | 3/2004 |
| WO | WO 2004/021987 A2 | 3/2004 |
| WO | WO 2004/037798 A1 | 5/2004 |
| WO | WO 2004/039753 A2 | 5/2004 |
| WO | WO 2004/043939 A1 | 5/2004 |
| WO | WO 2004/046141 A1 | 6/2004 |
| WO | WO 2004/056775 A1 | 7/2004 |
| WO | WO 2004/056777 A1 | 7/2004 |
| WO | WO 2004/078114 A2 | 9/2004 |
| WO | WO 2004/085420 A1 | 10/2004 |
| WO | WO 2004/111014 A1 | 12/2004 |
| WO | WO 2005/049018 A1 | 6/2005 |
| WO | WO 2005/054191 A1 | 6/2005 |
| WO | WO 2005/070006 A2 | 8/2005 |
| WO | WO 2005/075435 A1 | 8/2005 |
| WO | WO 2005/080373 A1 | 9/2005 |
| WO | WO 2005/085216 A1 | 9/2005 |
| WO | WO 2005/099705 A2 | 10/2005 |
| WO | WO 2005/108369 A1 | 11/2005 |
| WO | WO 2006/002421 A2 | 1/2006 |
| WO | WO 2006/030807 A1 | 3/2006 |
| WO | WO 2006/039212 A2 | 4/2006 |
| WO | WO 2006/065204 A1 | 6/2006 |
| WO | WO 2006/066968 A1 | 6/2006 |
| WO | WO 2006/067392 A2 | 6/2006 |
| WO | WO 2007/019397 A2 | 2/2007 |
| WO | WO 2007/021982 A2 | 2/2007 |
| WO | WO 2007/053641 A2 | 5/2007 |
| WO | WO 2007/075946 A1 | 7/2007 |
| WO | WO 2007/079139 A2 | 7/2007 |
| WO | WO 2007/087066 A2 | 8/2007 |
| WO | WO 2007/113327 A2 | 10/2007 |
| WO | WO 2007/117715 A2 | 10/2007 |
| WO | WO 2007/134279 A2 | 11/2007 |
| WO | WO 2008/005457 A2 | 1/2008 |
| WO | WO 2008/100867 A2 | 8/2008 |
| WO | WO 2008/127399 A2 | 10/2008 |
| WO | WO 2008/141385 A1 | 11/2008 |
| WO | WO 2009/006315 A1 | 1/2009 |
| WO | WO 2009/027730 A1 | 3/2009 |
| WO | WO 2009/032116 A1 | 3/2009 |
| WO | WO 2009/038683 A2 | 3/2009 |
| WO | WO 2009/064848 A1 | 5/2009 |
| WO | WO 2009/071947 A2 | 6/2009 |
| WO | WO 2009/073757 A1 | 6/2009 |
| WO | WO 2009/076142 A2 | 6/2009 |
| WO | WO 2009/127822 A2 | 10/2009 |
| WO | WO 2009/138758 A2 | 11/2009 |
| WO | WO 2010/003444 A2 | 1/2010 |
| WO | WO 2010/007116 A2 | 1/2010 |
| WO | WO 2010/019239 A2 | 2/2010 |
| WO | WO 2010/022307 A2 | 2/2010 |
| WO | WO 2010/025295 A2 | 3/2010 |
| WO | WO 2010/053471 A1 | 5/2010 |
| WO | WO 2010/054138 A2 | 5/2010 |
| WO | WO 2010/065824 A2 | 6/2010 |
| WO | WO 2010/083441 A2 | 7/2010 |
| WO | WO 2010/102758 A2 | 9/2010 |
| WO | WO 2010/108162 A1 | 9/2010 |
| WO | WO 2010/110231 A1 | 9/2010 |
| WO | WO 2010/123822 A1 | 10/2010 |
| WO | WO 2010/138588 A2 | 12/2010 |
| WO | WO 2011/019413 A1 | 2/2011 |
| WO | WO 2011/068560 A1 | 6/2011 |
| WO | WO 2011/072241 A1 | 6/2011 |
| WO | WO 2011/102514 A1 | 8/2011 |
| WO | WO 2011/116397 A1 | 9/2011 |
| WO | WO 2011/119984 A1 | 9/2011 |
| WO | WO 2011/127241 A2 | 10/2011 |
| WO | WO 2011/127290 A2 | 10/2011 |
| WO | WO 2011/128251 A1 | 10/2011 |
| WO | WO 2011/133751 A2 | 10/2011 |
| WO | WO 2011/133951 A1 | 10/2011 |
| WO | WO 2011/150016 A1 | 12/2011 |
| WO | WO 2012/027247 A2 | 3/2012 |
| WO | WO 2012/027731 A2 | 3/2012 |
| WO | WO 2012/052540 A1 | 4/2012 |
| WO | WO 2012/087938 A2 | 6/2012 |
| WO | WO 2012/089721 A1 | 7/2012 |
| WO | WO 2012/089722 A2 | 7/2012 |
| WO | WO 2012/102297 A1 | 8/2012 |
| WO | WO 2012/110519 A1 | 8/2012 |
| WO | WO 2012/116960 A1 | 9/2012 |
| WO | WO 2012/139891 A1 | 10/2012 |
| WO | WO 2012/166415 A1 | 12/2012 |
| WO | WO 2012/170061 A1 | 12/2012 |
| WO | WO 2013/033068 A1 | 3/2013 |
| WO | WO 2013/037955 A1 | 3/2013 |
| WO | WO 2013/038373 A1 | 3/2013 |
| WO | WO 2013/041602 A1 | 3/2013 |
| WO | WO 2013/070961 A1 | 5/2013 |
| WO | WO 2013/082102 A1 | 6/2013 |
| WO | WO 2013/112804 A1 | 8/2013 |
| WO | WO 2013/118805 A1 | 8/2013 |
| WO | WO 2013/130669 A1 | 9/2013 |
| WO | WO 2013/158121 A1 | 10/2013 |
| WO | WO 2013/177224 A1 | 11/2013 |
| WO | WO 2013/185112 A1 | 12/2013 |
| WO | WO 2013/185202 A1 | 12/2013 |
| WO | WO 2014/008458 A2 | 1/2014 |
| WO | WO 2014/014841 A1 | 1/2014 |
| WO | WO 2014/017093 A1 | 1/2014 |
| WO | WO 2014/028381 A1 | 2/2014 |
| WO | WO 2014/028968 A1 | 2/2014 |
| WO | WO 2014/039714 A2 | 3/2014 |
| WO | WO 2014/047427 A2 | 3/2014 |
| WO | WO 2014/071122 A1 | 5/2014 |
| WO | WO 2014/071247 A1 | 5/2014 |
| WO | WO 2014/071378 A1 | 5/2014 |
| WO | WO 2014/086723 A1 | 6/2014 |
| WO | WO 2014/086739 A1 | 6/2014 |
| WO | WO 2014/086751 A1 | 6/2014 |
| WO | WO 2014/096388 A2 | 6/2014 |
| WO | WO 2014/109858 A1 | 7/2014 |
| WO | WO 2014/144100 A2 | 9/2014 |
| WO | WO 2014/152013 A1 | 9/2014 |
| WO | WO 2014/152018 A1 | 9/2014 |
| WO | WO 2014/180562 A1 | 11/2014 |
| WO | WO 2014/181287 A1 | 11/2014 |
| WO | WO 2014/190199 A1 | 11/2014 |
| WO | WO 2015/010832 A1 | 1/2015 |
| WO | WO 2015/031608 A1 | 3/2015 |
| WO | WO 2015/069287 A1 | 5/2015 |

(56) References Cited

FOREIGN PATENT DOCUMENTS

| | | |
|---|---|---|
| WO | WO 2015/073231 A1 | 7/2015 |
| WO | WO 2015/160787 A1 | 10/2015 |
| WO | WO 2016/057730 A1 | 2/2016 |
| WO | WO 2016/057572 A1 | 4/2016 |
| WO | WO 2016/081556 A1 | 5/2016 |
| WO | WO 2016/105484 A1 | 6/2016 |
| WO | WO 2016/105485 A2 | 6/2016 |
| WO | WO 2016/128529 A1 | 8/2016 |
| WO | WO 2016/160945 A1 | 10/2016 |
| WO | WO 2017/053455 A1 | 3/2017 |
| WO | WO 2017/172802 A1 | 10/2017 |
| WO | WO 2017/173274 A1 | 10/2017 |
| WO | WO 2017/177124 A1 | 10/2017 |
| WO | WO 2017/187321 A1 | 11/2017 |
| WO | WO 2017/223188 A1 | 12/2017 |
| WO | WO 2018/064632 A1 | 4/2018 |
| WO | WO 2018/081377 A1 | 5/2018 |
| WO | WO 2018/081378 A1 | 5/2018 |
| WO | WO 2018/081381 A1 | 5/2018 |
| WO | WO 2018/107100 A1 | 6/2018 |
| WO | WO 2018/116185 A1 | 6/2018 |
| WO | WO 2018/127130 A1 | 7/2018 |
| WO | WO 2018/183367 A1 | 10/2018 |
| WO | WO 2018/201126 A1 | 11/2018 |
| WO | WO 2018/227049 A1 | 12/2018 |
| WO | WO 2019/010092 A1 | 1/2019 |
| WO | WO 2019/018353 A1 | 1/2019 |
| WO | WO 2019/018395 A1 | 1/2019 |
| WO | WO 2019/028228 A1 | 2/2019 |
| WO | WO 2019/071078 A1 | 4/2019 |
| WO | WO 2019/079760 A1 | 4/2019 |
| WO | WO 2019/113089 A1 | 6/2019 |
| WO | WO 2019/113476 A1 | 6/2019 |
| WO | WO 2019/152940 A1 | 8/2019 |
| WO | WO 2019/026075 A1 | 10/2019 |
| WO | WO 2019/191620 A1 | 10/2019 |
| WO | WO 2019/200246 A1 | 10/2019 |

OTHER PUBLICATIONS

"A CFTR corrector (lumacaftor) and a CFTR potentiator (ivacaftor) for treatment of patients with cystic fibrosis who have a phe508del CFTR mutation: a phase 2 randomised controlled trial", Boyle, M., The Lancet Respiratory Medicine (Jul. 1, 2014) Retrieved from the Internet: https://www-clinicalkeycom-ez03.infotrieve.com/#!/content/playContent/1-S2.0S2213260014701328?returnurl=null&referrer=null.
Anilkumar, G.N. et al. (2011) "IL Novel HCV NS5B polymerase inhibitors: Discovery of indole C2 acyl sulfonamides" *Biogranic & Medicinal Chemistry Letters*, 22(1):713-717.
Atzrodt J, Derdau V, Fey T, Zimmermann J. "The Renaissance of H/D Exchange" Angew. Chem. Int. Ed. 2007: 46, 7744-7765.
Atzrodt J, Derdau V, Kerr W, Reid M. "C-H functionalization for hydrogen isotope exchange" Angew. Chem. Int. Ed. 2018: 57, 3022-3047.
Belikov, V.G., (2007) *Farmatsevticheskaya khimiya (Pharmaceutical Chemistry)*, Moscow: MEDpress-inform, pp. 27-29.
Borhade, S.R. et al. (2013) "Synthesis of Novel Aryl and Heteroaryl Acyl Sulfonimidamides via Pd-Catalyzed Carbonylation Using a Nongaseous Precursor" *Organic Lett*, 15(5):1056-1059.
Braman, V.; Liu, J. F.; Harbeson, S.; Uttamsingh, V.; Bridson, G.; Wu, L.; Shipley, J. E. "Preliminary Clinical Outcomes for CTP-354, a Novel Subtype-Selective GABA(A) Modulator" Presented at the American Neurological Association (ANA) 2014 Annual Meeting, Baltimore, MD, Oct. 12-14, 2014.
Byrn, S. et al. (1995) "Pharmaceutical solids: A strategic approach to regulatory considerations," (12): 945-954.
Caira, M. R. (1998) "Crystalline Polymorphism of Organic Compounds," *Topics in Current Chemistry*, 163-208.
Cargnin S, Serafini M, Pirali T. "A primer of deuterium in drug design" Future Med. Chem. 2019; 11 (16):2039-2042.

Chen, Y. (Jan. 2, 20166) "*N*-Monoacylation of Sulfonimidamides" *Synthesis*, 48(7):1019-1028.
Czeskis B, Elmore, CS, Haight A, Hesk D, Maxwell BD, Miller SA, Raglione T, Schildknegt K, Traverse JF, Wang P. "Deuterated active pharmaceutical ingredients: A science-based proposal for synthesis, analysis, and control. Part 1: Framing the problem" J. Label. Compd. Radiopharm. 2019, 62: 690-694. DOI: 10.1002/jlcr.3743.
Dao HT, Li C, Michaudel Q, Maxwell BD, Baran PS. J. Am. Chem. Soc. 2015; 137, 8046-8049.
Database Caplus, Accession No. 1965:51408. Abstract of French Patent No. FR M2868, filed Nov. 23, 1964, by Roussel-UCLAF [online]. Retrieved Jan. 6, 2017 (1 page).
Database Caplus, Accession No. 1965:51409. Abstract of German Patent No. DE 1182243, filed Nov. 26, 1964, by Badische Anilin & Soda-Fabrik A.G. [online]. Retrieved Jan. 6, 2017 (2 pages).
Database Pubchem, CID: 20050716. Compound Summary, *1-[2-[[2-[(2-Amino-3-methylbutanoyl)amino]-3-methylpentanoyl]amino]-3-phenylpropanoyl]pyrrolidine-2-carboxylic acid*. NIH, U.S. National Library of Medicine, National Center for Biotechnology Information; Modify Date: Nov. 30, 2019. [online]. Retrieved from https://pubchem.ncbi.nlm.nih.gov/compound/20050716, on Dec. 3, 2019 (7 pages).
Database Pubchem, CID: 20091118. Compound Summary, *[4-(5-Hexylpyrimidin-2-yl)phenyl] 2-methoxypropanoate*. NIH, U.S. National Library of Medicine, National Center for Biotechnology Information; Modify Date: Nov. 30, 2019. [online]. Retrieved from https://pubchem.ncbi.nlm.nih.gov/compound/20091118, on Dec. 3, 2019 (9 pages).
Database Pubchem, CID: 20120819. Compound Summary, *4-(Cyclopentyloxy)-3-fluorobenzene-1-sulfonyl chloride*. NIH, U.S. National Library of Medicine, National Center for Biotechnology Information; Modify Date: Nov. 30, 2019. [online]. Retrieved from https://pubchem.ncbi.nlm.nih.gov/compound/20120819, on Dec. 3, 2019 (8 pages).
Database Pubchem, CID: 2545578. Compound Summary, *T5339296*. NIH, U.S. National Library of Medicine, National Center for Biotechnology Information; Modify Date: Jan. 16, 2016. [online]. Retrieved from https://pubchem.ncbi.nlm.nih.gov/compound/2545578, on Jan. 22, 2016 (9 pages).
Database Pubchem, CID: 44419393. Compound Summary, *CHEMBL374189*. NIH, U.S. National Library of Medicine, National Center for Biotechnology Information; Modify Date: Jan. 16, 2016. [online]. Retrieved from https://pubchem.ncbi.nlm.nih.gov/compound/44419393, on Jan. 22, 2016 (11 pages).
Database Pubchem, CID: 49774135. Compound Summary, *SCHEMBL13395127*. NIH, U.S. National Library of Medicine, National Center for Biotechnology Information; Modify Date: Jan. 16, 2016 [online], Retrieved from https://pubchem.ncbi.nlm.nih.gov/compound/49774135, on Jan. 22, 2016 (10 pages).
Database Pubchem, CID: 58132855. Compound Summary, *SCHEMBL831192*. NIH, U.S. National Library of Medicine, National Center for Biotechnology Information, PubChem Open Chemistry Database; Modify Date: Jan. 16, 2016 [online]. Retrieved from: https://pubchem.ncbi.nlm.nih.gov/compound/58132855, on Jan. 22, 2016 (10 pages).
Dorwald, F. A. (2006) "Side Reactions in Organic Synthesis" Wiley: VCH, Weinheim p. IX of Preface p. 1-15.
Gant TG. "Using Deuterium in Drug Discovery: Leaving the Label in the Drug" J Med. Chem. 2014; 57(9): 3595-3611.
Garg, V et al. "Pharmacokinetic and Drug-Drug Interaction Profiles of the Combination of Tezacaftor/Ivacaftor", Clinical and Translational Science—CTS, vol. 12, No. 3, Jan. 29, 2019 (Jan. 29, 2019), pp. 267-275, XP055719490, US ISSN: 1752-8054, DOI: 10.1111/cts.12610.
Halford B. "The deuterium switcheroo" Chemical & Engineering News 2016; 94(27), 32-36.
Hopkins, C.R. et al. (2006) "Design and synthesis of novel N-sulfonyl-2-indole carboxamides as potent PPAR-gamma binding agents with potential application to the treatment of osteoporosis" Bioorganic & Medicinal Chemistry Letters, 16(21):5659-5663.
International Patent Application No. PCT/US2015/54316: International Search Report and Written Opinion, dated Feb. 5, 2016 (11 pages).

(56) References Cited

OTHER PUBLICATIONS

International Patent Application No. PCT/US2017/025381: International Search Report and Written Opinion, dated Jun. 6, 2017 (11 pages).
International Patent Application No. PCT/US2017/054611: International Search Report and Written Opinion, dated Jan. 3, 2018 (10 pages).
International Patent Application No. PCT/US2017/065425: International Search Report and Written Opinion, dated Feb. 27, 2018 (10 pages).
International Patent Application No. PCT/US2018/036610: International Search Report and Written Opinion, dated Sep. 19, 2018 (9 pages).
International Patent Application No. PCT/US2018/040427: International Search Report and Written Opinion, dated Oct. 9, 2018 (15 pages).
International Patent Application No. PCT/US2018/042415: International Search Report and Written Opinion, dated Oct. 31, 2018 (12 pages).
International Patent Application No. PCT/US2018/042486: International Search Report and Written Opinion, dated Nov. 7, 2018 (13 pages).
International Patent Application No. PCT/US2018/044963: International Search Report and Written Opinion, dated Sep. 25, 2018 (15 pages).
International Patent Application No. PCT/US2018/056772: International Search Report and Written Opinion, dated Jan. 29, 2019 (13 pages).
International Patent Application No. PCT/US2018/063871: International Search Report and Written Opinion, dated Feb. 25, 2019 (16 pages).
International Patent Application No. PCT/US2019/016537: International Search Report and Written Opinion, dated Apr. 23, 2019 (13 pages).
International Patent Application No. PCT/US2018/064522: International Search Report and Written Opinion, dated Jun. 25, 2019 (21 pages).
International Patent Application No. PCT/US2019/018042: International Search Report and Written Opinion, dated Apr. 17, 2019 (10 pages).
International Patent Application No. PCT/US2019/024890: International Search Report and Written Opinion, dated Jun. 17, 2019 (13 pages).
International Patent Application No. PCT/US2019/026075: International Search Report and Written Opinion, dated Jun. 17, 2019 (13 pages).
International Patent Application No. PCT/US2019/027202: International Search Report and Written Opinion, dated Jun. 17, 2019 (10 pages).
International Patent Application No. PCT/US2020/028699: International Search Report and Written Opinion, dated Jul. 20, 2020 (9 pages).
International Patent Application No. PCT/US2020/034199: International Search Report and Written Opinion, dated Aug. 11, 2020 (15 pages).
Jain, B.C. et al. (1947) "Studies in Sulphanilamides. Part XIII. Reaction With Dicarboxylic Acids. Some New N1- and N4-ACYL and Heterocyclic Derivatives" *Journal of the Indian Chemical Society*, 24:173-176.
Kettle, J.G. et al. (2004) "N-Benzylindole-2-carboxylic acids: potent functional antagonists of the CCR2b chemokine receptor" *Bioorganic & Medicinal Chemistry Letters*, 14(2): 405-408.
Kieltsch, I et al. Laureates: Awards and Honors SCS Fall Meeting 2007 260 Recent Advances in Electrophilic CF 3 -Transfer Using Hypervalent Iodine(III) Reagents 11, A Chimia Chimia Schweizerische Chemische Gesellschaft ISSN, vol. 62, No. 62, Jan. 1, 2008 (Jan. 1, 2008), pp. 260-263, XP055591571, DOI: 10.2533/chimia.2008.260.
Lai, J.T. et al. (1980) "Rearrangement of 2,2,6,6-tetramethyl-4-piperidone in phase-transfer catalyzed reactions," *Journal of Organic Chemistry*, 45(8):1513-1514.

Liu, J. F. et al. "CTP-354: A Novel Deuterated Subtype-Selective GABA(A) Modulator for Treatment of Neuropathic Pain, Spasticity and Anxiety Disorders" Presented at the American College of Neuropsychopharmacology (ACNP) 51st Annual Meeting, Hollywood, FL, Dec. 2-6, 2012.
Matter, H. et al. (2002) "Design and Quantitative Structure-Activity Relationship of 3-Amidinobenzyl-1H-indole-2-carboxamides as Potent, Nonchiral, and Selective Inhibitors of Blood Coagulation Factor Xa" *Journal of Medicinal Chemistry*, 45(13):2749-2769.
Maxwell BD, Tran SB, Lago M, Li J, and Bonacorsi Jr SJ. "The syntheses of [14C]BMS-823778 for use in a human ADME clinical study and of [13CD313CD2]BMT-094817, a stable-isotope labeled standard of a newly detected human metabolite" J. Label. Compd. Radiopharm. 2016; 59, 255-259.
Montemayor, Kristina et al. "Unmasking catamenial hemoptysis in the era of CFTR modulator therapy", Journal of Cystic Fibrosis, Elsevier, NL, vol. 19, No. 4, Jan. 24, 2020 (Jan. 24, 2020), XP086202454, ISSN: 1569-1993, DOI: 10.1016/J.JCF.2020.01.005 [retrieved on Jan. 24, 2020].
NCT03029455 "A Study to Evaluate Safety and Pharmacokinetics of VX-659 in Healthy Subjects and in Adults With Cystic Fibrosis". Vertex Pharmaceuticals Incorporated, Retrieved from the Internet: https://clinicaltrials.gov/ct2/show/study/NCT03029455.
Norman, P. (2014) "Novel picolinamide-based cystic fibrosis transmembrane regulator modulators: evaluation of WO2013038373, WO2013038376, WO2013038381, WO2013038386, and WO2013038390," *Expert Opinion on Therapeutic Patents*, 24(7):829-837.
Notice of Allowance and Fee(s) Due for U.S. Appl. No. 15/836,627, dated Jun. 18, 2020.
Notman, N. (2016) "2Heavy drugs gaining momentum" [online] Retrieved from the internet: https://www.chemistryworld.com/features/2heavy-drugs-gaining-momentum/1010186.article, on Oct. 7, 2019.
Passarella, D. et al. (2001) "Cyclodimerization of indol-2-ylacetylenes. An example of intermolecular enyne-alkyne cycloaddition" *Journal of the Chemical Society*, Perkin Transactions 1, 127-129.
Pirali T, Serafini M, Cargnin S, Genazzani AA. "Applications of Deuterium in Medicinal Chemistry" J Med. Chem. 2019; 62(11): 5276-5297.
Qun, C. et al. "Synthesis of 3,3,3-trifluoro-2,2-dimethylpropionic acid", Huaxue Shiji—Chemical Reagents, Beijing : Huaxue Huaxue Shiji Keji Qingbao Zhongxinzhan, CN, vol. 38, No. 4, Jan. 1, 2016 (Jan. 1, 2016), pp. 386-388, XP009513488, ISSN: 0258-3283, DOI: 10.13822/J.CNKI.HXSJ.2016.04.026.
Rosebraugh, C.J. (2015) "Highlights of Prescribing Information for Orkambi," [online] Retrieved from the Internet: https://www.accessdata.fda.gov/drugsatfda_docs/label/2015/206038Orig1s000lbl.pdf, on Aug. 24, 2017.
Schmidt C. "First deuterated drug approved" Nat. Biotechnol. 2017, 35, 493-494.
Silverman, R. (2004) The Organic Chemistry of Drug Design and Drug Action, Elsevier, pp. 29-32.
Soloducho, J. (1989) "Synthesis of Some Pyrido [2,3-c][1,2,6]triazinone Derivatives" *Journal für Pracktische Chemie*, 331(3):503-506.
Tsong-Long H. et al. "Synthesis and pharmacological characterization of 2-aminobenzaldehyde oxime analogs as dual inhibitors of neutrophil elastase and proteinase 3", Bioorganic & Medicinal Chemistry, vol. 23, No. 5, Jan. 16, 2015, pp. 1123-1134, XP029199003.
Tullis, E. et al. (2018) "Preliminary safety and efficacy of triple-combination CFTR modulator regimens," *Respirology*, 23(51):33.
U.S. Appl. No. 16/620,265, filed Dec. 6, 2019, by Chen et al.
U.S. Appl. No. 16/625,028, filed Dec. 20, 2019, by Chu et al.
U.S. Appl. No. 16/631,989, filed Jan. 17, 2020, by Haseltine et al.
U.S. Appl. No. 16/635,346, filed Jan. 30, 2020, by Angell et al.
U.S. Appl. No. 16/836,155, filed Mar. 31, 2020, by Miller et al.
Uttamsingh, V. et al. (2016) "WS13.6 CTP-656 tablet confirmed superiority of pharmacokinetic profile relative to Kalydeco in Phase I clinical studies" *Journal of Cystic Fibrosis*, 15:S22.

(56) References Cited

OTHER PUBLICATIONS

Venkatesh, S. et al. (2000) "Role of the development scientist in compound lead selection and optimization" *J. Pharm. Sci.* 89(2), 145-154.

Verado, G. et al. (1999) "Reductive One Batch Synthesis of N-Substituted Pyrrolidines from Primary Amines and 2,5-Dimethoxytetrahydrofuran" *Synthesis*, (1):74-79.

Vertex Pharmaceuticals, Inc. (Mar. 28, 2017) "Two Phase 3 Studies of the Tezacaftor/Ivacaftor Combination Treatment Met Primary Endpoints with Statistically Significant Improvements in Lung Function (FEV1) in People With Cystic Fibrosis" [online] Retrieved from the Internet: http://investors.vrtx.com/static-files/f15217ac-4a8b-436a-9215-79144ec2e59b, on Oct. 10, 2019.

Vertex Pharmaceuticals, Inc. (Jul. 18, 2017) "Vertex Announces Positive Phase 1 & Phase 2 Data from Three Different Triple Combination Regimens in People with Cystic Fibrosis Who Have One F508del Mutation and One Minimal Function Mutation (F508del/Min)", Retrieved from the Internet: URL: http://investors.vrtx.com/news-releases/news-release-details/vertex/announces-positive-phase-1-phase-2-data-three-different [retrieved on Mar. 27, 2019].

Vertex Pharmaceuticals, Inc. (Nov. 3, 2017) "Vertex announces presentations of data at North American Cystic Fibrosis Conference that Demonstrate Important Progress Toward Goal of Helping All People with CF," Health and Medicine Week, vol. 3, p. 196.

"Vertex Provides Update on Ongoing Phase 3 Program for VX-661 in Combination with Ivacaftor for the Treatment of Cystic Fibrosis" (Aug. 15, 2016) Retrieved from the Internet: https://www.businesswire.com/news/home/20160815006099/en/Vertex-Update-Ongoing-Phase-3-Program-VX-661.

Vodak, D. (2014) "Design and Development of HPMCAS-Based Spray-Dried Dispersions," 303-322.

Wainwright, C.E. et al. (2015) "Lumacaftor-Ivacaftor in Patients with Cystic Fibrosis Homozygous for Phe508del CFTR," *The New England Journal of Medicine*, 373(3):220-231.

Willson T. M. et al. (1996) "Bone targeted drugs 2. Synthesis of estrogens with hydroxyapatite affinity," Bioorg. & Med. Chem. Lett., (6):1047-1050.

Winn, M. et al. (1993) "2-(Alkylamino)nicotinic Acid and Analogs. Potent Angiotensin II Antagonists" *Journal of Medicinal Chemistry*, 36(18):2676-2688.

Yarnell AT. "Heavy-Hydrogen Drugs Turn Heads, Again" Chemical & Engineering News 2009; 87(25), 36-39.

\* cited by examiner

PROCESSES FOR PREPARING PYRROLIDINE COMPOUNDS

This application is a national stage application under 35 U.S.C. § 371 of international application number PCT/US2018/044963, filed Aug. 2, 2018, which designated the U.S. and claims priority to U.S. Provisional Patent Application No. 62/540,395, filed Aug. 2, 2017, which are incorporated herein by reference in their entirety.

(S)-2,2,4-trimethylpyrrolidine free base and salt forms thereof, (R)-2,2,4-trimethylpyrrolidine free base and salt forms thereof, (S)-3,5,5-trimethylpyrrolidine-2-one, (R)-3,5,5-trimethylpyrrolidine-2-one, and 5,5-dimethyl-3-methylenepyrrolidin-2-one are useful molecules that can be used in the synthesis of pharmaceutically active molecules, such as modulators of CFTR activity, for example those disclosed in PCT Publication Nos. WO 2016/057572, WO 2018/064632, and WO 2018/107100, including the following molecules, which are being investigated in clinical trials for the treatment of cystic fibrosis:

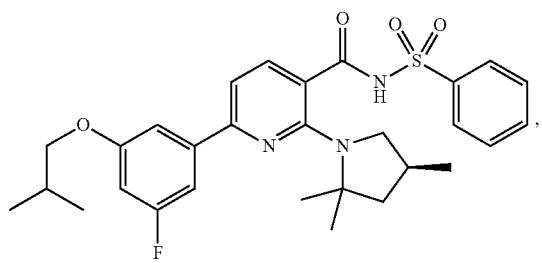

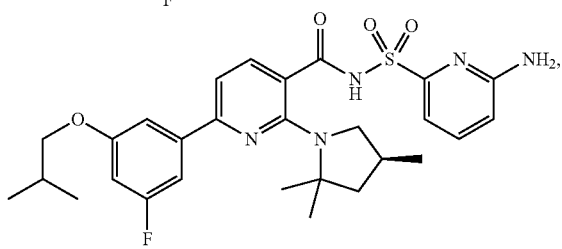

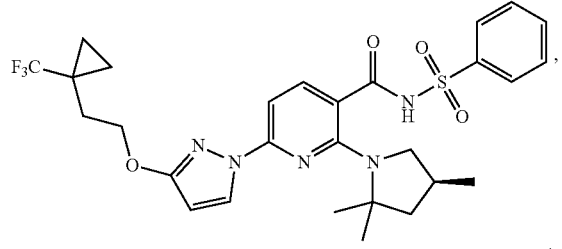

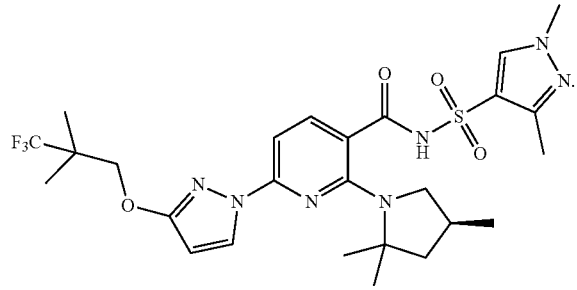

There remains, however, a need for more efficient, convenient, and/or economical processes for the preparation of these molecules.

Disclosed herein are processes for preparing 5,5-dimethyl-3-methylenepyrrolidin-2-one, (S)-3,5,5-trimethylpyrrolidine-2-one, (R)-3,5,5-trimethylpyrrolidine-2-one, (S)-2,2,4-trimethylpyrrolidine, and (R)-2,2,4-trimethylpyrrolidine, and their salt forms:

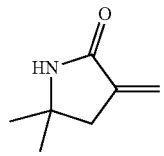

(5,5-dimethyl-3-methylenepyrrolidin-2-one);

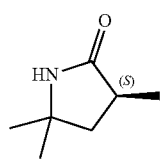

((S)-3,5,5-trimethylpyrrolidine-2-one));

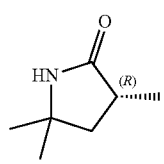

((R)-3,5,5-trimethylpyrrolidine-2-one));

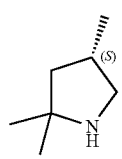

((S)-2,2,4-trimethylpyrrolidine); and

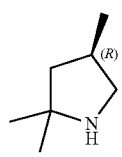

((R)-2,2,4-trimethylpyrrolidine).

In some embodiments, processes for preparing 5,5-dimethyl-3-methylenepyrrolidin-2-one are disclosed.

In some embodiments, the disclosure is drawn to processes for preparing (S)-2,2,4-trimethylpyrrolidine free base or (S)-2,2,4-trimethylpyrrolidine salts. In some embodiments, the (S)-2,2,4-trimethylpyrrolidine salt is (S)-2,2,4-trimethylpyrrolidine hydrochloride.

In some embodiments, the disclosure is drawn to processes for preparing (R)-2,2,4-trimethylpyrrolidine free base or (R)-2,2,4-trimethylpyrrolidine salts. In some embodiments, the (R)-2,2,4-trimethylpyrrolidine salt is (R)-2,2,4-trimethylpyrrolidine hydrochloride.

In some embodiments, the disclosure is drawn to processes for preparing (S)-3,5,5-trimethylpyrrolidine-2-one.

In some embodiments, the disclosure is drawn to processes for (R)-3,5,5-trimethylpyrrolidine-2-one.

In some embodiments, a process for preparing (S)-2,2,4-trimethylpyrrolidine is depicted in Scheme 1 and comprises:
(a) reacting 2,2,6,6-tetramethyl-piperidin-4-one or a salt thereof with chloroform and at least one base;
(b) reacting the products of the reaction in (a) with an acid to produce 5,5-dimethyl-3-methylenepyrrolidin-2-one;
(c) hydrogenating 5,5-dimethyl-3-methylenepyrrolidin-2-one to produce (S)-3,5,5-trimethyl-pyrrolidin-2-one; and
(d) reducing (S)-3,5,5-trimethyl-pyrrolidin-2-one to produce (S)-2,2,4-trimethylpyrrolidine.

Scheme 1. Synthesis of (S)-2,2,4-trimethylpyrrolidine

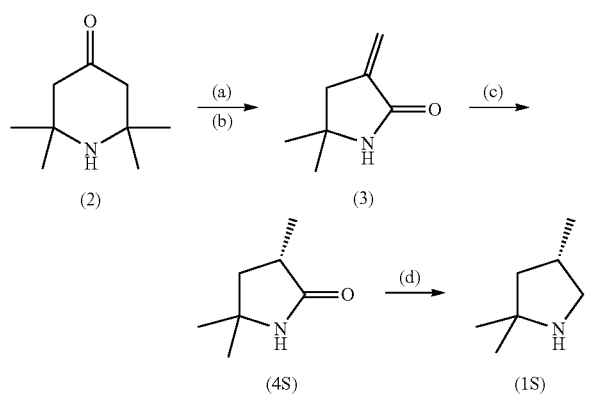

In some embodiments, a salt of 2,2,6,6-tetramethyl-piperidin-4-one is used. Non-limiting examples of salts include a hydrochloride salt, a hydrobromide salt, a sulfate salt, a phoshpate salt, a fumarate salt, an oxalate salt, a maleate salt, a citrate salt, or a benzoate salt. In some embodiments, 2,2,6,6-tetramethyl-piperidin-4-one hydrochloride is used. These salts can be prepared by conventional methods in the art, by for example, treating 2,2,6,6-tetramethyl-piperidin-4-one with an acid.

In some embodiments, a process for preparing a salt of (S)-2,2,4-trimethylpyrrolidine is disclosed and comprises:
(a) reacting 2,2,6,6-tetramethyl-piperidin-4-one or a salt thereof with chloroform and at least one base;
(b) reacting the products of the reaction in (a) with an acid to produce 5,5-dimethyl-3-methylenepyrrolidin-2-one;
(c) hydrogenating 5,5-dimethyl-3-methylenepyrrolidin-2-one to produce (S)-3,5,5-trimethyl-pyrrolidin-2-one;
(d) reducing (S)-3,5,5-trimethyl-pyrrolidin-2-one to produce (S)-2,2,4-trimethylpyrrolidine; and
(e) treating (S)-2,2,4-trimethylpyrrolidine with acid to produce a salt of (S)-2,2,4-trimethylpyrrolidine.

In some embodiments, a process for preparing (R)-2,2,4-trimethylpyrrolidine is depicted in Scheme 2 and comprises:
(a) reacting 2,2,6,6-tetramethyl-piperidin-4-one or a salt thereof with chloroform and at least one base;
(b) reacting the products of the reaction in (a) with an acid to produce 5,5-dimethyl-3-methylenepyrrolidin-2-one;
(c) hydrogenating 5,5-dimethyl-3-methylenepyrrolidin-2-one to produce (R)-3,5,5-trimethyl-pyrrolidin-2-one; and
(d) reducing (R)-3,5,5-trimethyl-pyrrolidin-2-one to produce (R)-2,2,4-trimethylpyrrolidine.

Scheme 2. Synthesis of (R)-2,2,4-trimethylpyrrolidine

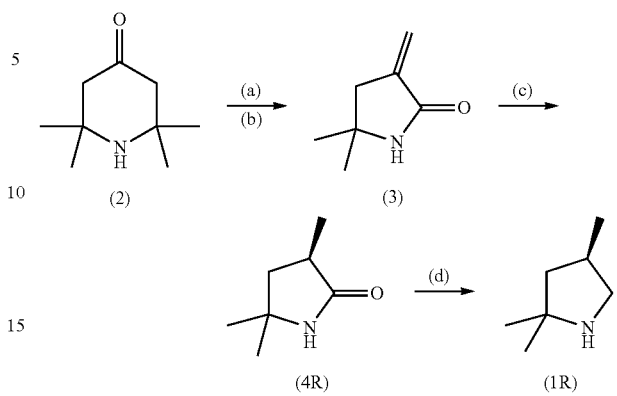

In some embodiments, a process for preparing a salt of (R)-2,2,4-trimethylpyrrolidine is disclosed and comprises:
(a) reacting 2,2,6,6-tetramethyl-piperidin-4-one or a salt thereof with chloroform and at least one base;
(b) reacting the products of the reaction in (a) with an acid to produce 5,5-dimethyl-3-methylenepyrrolidin-2-one;
(c) hydrogenating 5,5-dimethyl-3-methylenepyrrolidin-2-one to produce (R)-3,5,5-trimethyl-pyrrolidin-2-one;
(d) reducing (R)-3,5,5-trimethyl-pyrrolidin-2-one to produce (R)-2,2,4-trimethylpyrrolidine; and
(e) treating (R)-2,2,4-trimethylpyrrolidine with acid to produce a salt of (R)-2,2,4-trimethylpyrrolidine.

In some embodiments, a process for preparing 5,5-dimethyl-3-methylenepyrrolidin-2-one is depicted in Scheme 3 and comprises:
(a) reacting 2,2,6,6-tetramethyl-piperidin-4-one or a salt thereof with chloroform and at least one base; and
(b) reacting the products of the reaction in (a) with an acid to produce 5,5-dimethyl-3-methylenepyrrolidin-2-one.

Scheme 3. Synthesis of 5,5-dimethyl-3-methylenepyrrolidin-2-one

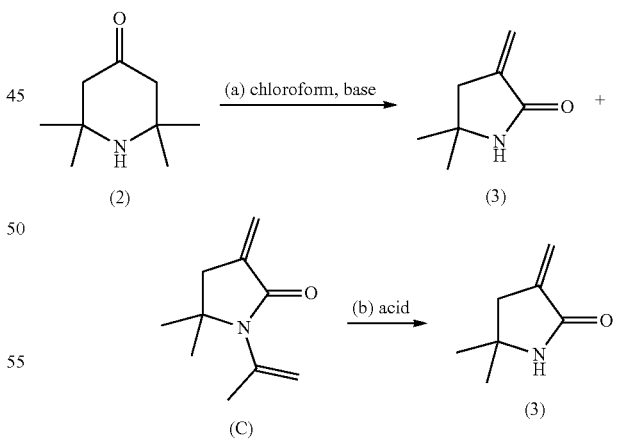

The reaction of 2,2,6,6-tetramethyl-piperidin-4-one (Compound 2 in scheme 3) or a salt thereof with chloroform and at least one base in the reaction in (a) generates a mixture of 5,5-dimethyl-3-methylenepyrrolidin-2-one (Compound 3) and 5,5-dimethyl-3-methylene-1-(prop-1-en-2-yl)pyrrolidin-2-one (Compound C), as shown in scheme 3. To isolate compound 3, previous methods involved separation of compound 3 and compound C, which required additional time, materials, and solvent. It also resulted in low yields of compound 3, due to high amounts of the compound C byproduct. In an effort to increase yield of compound 3, it was unexpectedly found that the crude mixture of compound 3 and compound C can be treated with acid, as shown in the reaction in (b), and compound C is converted to Compound 3. In some embodiments, the reaction in (b) is conducted without isolation of the product(s) of the reaction in (a). This results in a process with fewer purifications and less reliance on materials and solvents, which can provide compound 3 in higher efficiency and lower cost.

In some embodiments, a process for preparing (S)-3,5,5-trimethylpyrrolidin-2-one is depicted in Scheme 4 and comprises:

(a) reacting 2,2,6,6-tetramethyl-piperidin-4-one or a salt thereof with chloroform and at least one base;

(b) reacting the products of the reaction in (a) with an acid to produce 5,5-dimethyl-3-methylenepyrrolidin-2-one; and (c) hydrogenating 5,5-dimethyl-3-methylenepyrrolidin-2-one to produce (S)-3,5,5-trimethyl-pyrrolidin-2-one.

Scheme 4. Synthesis of (S)-3,5,5-trimethylpyrrolidin-2-one

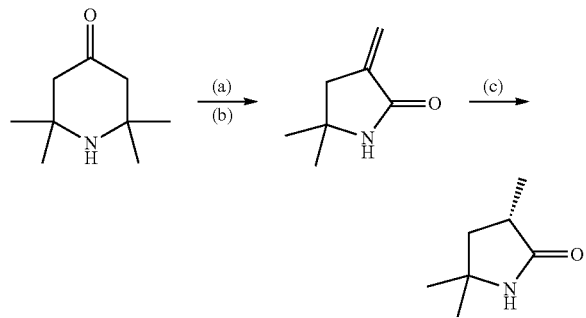

In some embodiments, a process for preparing (R)-3,5,5-trimethylpyrrolidin-2-one is depicted in Scheme 5 and comprises:

(a) reacting 2,2,6,6-tetramethyl-piperidin-4-one with chloroform and at least one base;

(b) reacting the products of the reaction in (a) with an acid to produce 5,5-dimethyl-3-methylenepyrrolidin-2-one; and (c) hydrogenating 5,5-dimethyl-3-methylenepyrrolidin-2-one to produce (R)-3,5,5-trimethyl-pyrrolidin-2-one.

Scheme 5. Synthesis of (R)-3,5,5-trimethyl pyrrolidin-2-one

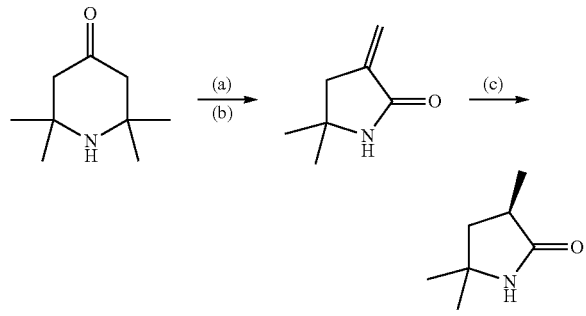

(a) Reaction of 2,2,6,6-tetramethyl-piperidin-4-one or a Salt Thereof with Chloroform and at Least One Base In some embodiments, 2,2,6,6-tetramethyl-piperidin-4-one or a salt thereof is reacted with chloroform and at least one base. In some embodiments, the at least one base is chosen from potassium t-butoxide, potassium hydroxide, and sodium hydroxide. In some embodiments, the at least one base is sodium hydroxide.

In some embodiments, 3 to 15 molar equivalents of the at least one base relative to the mole of 2,2,6,6-tetramethylpiperidin-4-one are added for the reaction in (a). In some embodiments, 5 to 12 molar equivalents of the at least one base are added. In some embodiments, 7.5 molar equivalents of the at least one base are added. In some embodiments, 10 molar equivalents of said at least one base are added. In some embodiments, 8 molar equivalents of sodium hydroxide are added.

In some embodiments, the at least one base in the reaction (a) is in solid form in at least one anhydrous solvent. In some embodiments, the at least one anhydrous solvent is chosen from dimethylsulfoxide and isopropyl alcohol.

In some embodiments, the at least one base in the reaction (a) is in the form of an aqueous solution having a concentration ranging from 20 wt % to 80 wt % relative to the total weight of the solution. In some embodiments, the at least one base is 20 wt % aqueous NaOH. In some embodiments, the at least one base is 30 wt % aqueous NaOH. In some embodiments, the at least one base is 40 wt % aqueous NaOH. In some embodiments, the at least one base is 50 wt % aqueous NaOH.

In some embodiments, chloroform in the reaction (a) is present in an amount ranging from 1 to 4 molar equivalents relative to the mole of 2,2,6,6-tetramethylpiperidin-4-one. In some embodiments, the chloroform is present in an amount ranging from 1.5 to 3.5 molar equivalents relative to the mole of 2,2,6,6-tetramethylpiperidin-4-one. In some embodiments, the chloroform is present in an amount of 1.75 molar equivalents relative to the mole of 2,2,6,6-tetramethylpiperidin-4-one.

In some embodiments, 2,2,6,6-tetramethyl-piperidin-4-one or a salt thereof is reacted with chloroform, at least one base, and at least one solvent. In some embodiments, the at least one solvent is chosen from organic solvents. In some embodiments, the at least one solvent is immiscible with water. In some embodiments, the volume of the at least one solvent ranges from 0.1 to 10 volume equivalents relative to the volume of 2,2,6,6-tetramethylpiperidin-4-one. In some embodiments, the volume of the at least one solvent ranges from 1 to 4 volume equivalents relative to the volume of 2,2,6,6-tetramethylpiperidin-4-one. In some embodiments, the volume of the at least one solvent ranges from 1 to 3 volume equivalents relative to the volume of 2,2,6,6-tetramethylpiperidin-4-one. In some embodiments, the volume of the at least one solvent ranges from 1.5 to 2.5 volume equivalents relative to the volume of 2,2,6,6-tetramethylpiperidin-4-one. In some embodiments, the volume of the at least one solvent is 2 volume equivalents of the at least one solvent relative to the volume of 2,2,6,6-tetramethylpiperidin-4-one. In some embodiments, the at least one solvent is chosen from dichloromethane, heptane, chloroform, trifluorotoluene, tetrahydrofuran (THF), and N-methylpyrrolidone (NMP). In some embodiments, the at least one solvent is chosen from dichloromethane and heptane. In some embodiments, the at least one solvent is dichloromethane.

In some embodiments, the reaction (a) is performed without the at least one solvent.

In some embodiments, the reaction in (a) is performed without the use of phase transfer catalyst.

In some embodiments, in the reaction in (a), in addition to chloroform and at least one base, 2,2,6,6-tetramethyl-piperidin-4-one is reacted with at least one phase transfer catalyst. In some embodiments, the at least one phase transfer catalyst is chosen from tetraalkylammonium salts and crown ethers such as 18-crown-6 and 15-crown-5 phase transfer catalysts. In some embodiments, the at least one phase transfer catalyst is chosen from crown ethers, such as 18-crown-6 and 15-crown-5 phase transfer catalysts. In some embodiments, the at least one phase transfer catalyst is chosen from tetraalkylammonium salts. In some embodiments, the at least one phase transfer catalyst is chosen from tetraalkylammonium halides. In some embodiments, the at least one phase transfer catalyst is chosen from tributylmethylammonium chloride, tributylmethylammonium bromide, tetrabutylammonium bromide (TBAB), tetrabutylammonium chloride (TBAC), tetrabutylammonium iodide (TBAI), tetrabutylammonium hydroxide (TBAH), benzyltrimethylammonium chloride, tetraoctylammonium bromide (TOAB), tetraoctylammonium chloride (TOAC), tetraoctylammonium iodide (TOAI), trioctylmethylammonium chloride, and trioctylmethylammonium bromide.

In some embodiments, 0.01 molar equivalents to 0.2 molar equivalents of the at least one phase transfer catalyst relative to the mole of 2,2,6,6-tetramethylpiperidin-4-one is added to the reaction in (a). In some embodiments, 0.02 molar equivalents to 0.1 molar equivalents of said at least one phase transfer catalyst relative to the mole of 2,2,6,6-tetramethylpiperidin-4-one is added. In some embodiments, 0.03 molar equivalents to 0.06 molar equivalents of said at least one phase transfer catalyst relative to the mole of 2,2,6,6-tetramethylpiperidin-4-one is added. In some embodiments, 0.01 molar equivalents to 1 molar equivalent, such as to 0.2 molar equivalents, 0.4 molar equivalents, 0.6 molar equivalents, or 0.8 molar equivalents of said at least one phase transfer catalyst relative to the mole of 2,2,6,6-tetramethylpiperidin-4-one is added.

(b) Reaction of the Products of the Reaction in (a) with Acid to Produce 5,5-dimethyl-3-methylenepyrrolidin-2-one In some embodiments, the acid of the reaction in (b) is chosen from aqueous solutions of protic acids. In some embodiments, the protic acids are chosen from hydrochloric acid, methane sulfonic acid, triflic acid, and sulfuric acid. In some embodiments, the concentration of said aqueous solutions of protic acids range from 1M to 18M. In some embodiments, the concentration of said aqueous solutions of protic acids range from 2M to 10M. In some embodiments, the acid of the reaction in (b) is chosen from HCl having a concentration ranging from 2M to 3M. In some embodiments, the acid of the reaction in (b) is chosen from 2M HCl. In some embodiments, the acid of the reaction in (b) is chosen from 2.5M HCl. In some embodiments, the acid of the reaction in (b) is chosen from 3M HCl. In some embodiments, 0.5 to 10 molar equivalents of said acid relative to the mole of 2,2,6,6-tetramethylpiperidin-4-one are added to the reaction in (b). In some embodiments, 1 to 4 molar equivalents of said acid relative to the mole of 2,2,6,6-tetramethylpiperidin-4-one are added to the reaction in (b). In some embodiments, 1.5 molar equivalents of said acid relative to the mole of 2,2,6,6-tetramethylpiperidin-4-one are added to the reaction in (b).

In some embodiments, the yield of 5,5-dimethyl-3-methylenepyrrolidin-2-one produced from the reactions in (a) and (b) ranges from 40% to 70% relative to the mole of 2,2,6,6-tetramethylpiperidin-4-one. In some embodiments, the yield of 5,5-dimethyl-3-methylenepyrrolidin-2-one produced from the reactions in (a) and (b) ranges from 30% to 80% relative to the mole of 2,2,6,6-tetramethylpiperidin-4-one. In some embodiments, the yield of 5,5-dimethyl-3-methylenepyrrolidin-2-one produced from the reactions in (a) and (b) ranges from 50% to 70% relative to the mole of 2,2,6,6-tetramethylpiperidin-4-one. In some embodiments, the yield of 5,5-dimethyl-3-methylenepyrrolidin-2-one produced from the reactions in (a) and (b) ranges from 60% to 80% relative to the mole of 2,2,6,6-tetramethylpiperidin-4-one.

(c) Hydrogenating 5,5-dimethyl-3-methylenepyrrolidin-2-one to Produce (S)- or (R)-3,5,5-trimethylpyrrolidin-2-one In some embodiments, 5,5-dimethyl-3-methylenepyrrolidin-2-one is hydrogenated to produce (S)- or (R)-3,5,5-trimethyl-pyrrolidin-2-one.

In some embodiments, the hydrogenation comprises reacting 5,5-dimethyl-3-methylenepyrrolidin-2-one with at least one catalyst and hydrogen gas to produce (S)-3,5,5-trimethyl-pyrrolidin-2-one. In some embodiments, the at least one catalyst is chosen from metals from the platinum group. As used herein, the term "platinum group" means ruthenium, rhodium, palladium, osmium, iridium, and platinum. In some embodiments, the at least one catalyst is chosen from ruthenium hydrogenation catalysts, rhodium hydrogenation catalysts, and iridium hydrogenation catalysts.

In some embodiments, the hydrogenation comprises reacting 5,5-dimethyl-3-methylenepyrrolidin-2-one with at least one catalyst and hydrogen gas to produce (R)-3,5,5-trimethyl-pyrrolidin-2-one. In some embodiments, the at least one catalyst is chosen from ruthenium hydrogenation catalysts, rhodium hydrogenation catalysts, and iridium hydrogenation catalysts.

The at least one catalyst may be heterogeneous or homogeneous. In some embodiments, the at least one catalyst is heterogeneous. In some embodiments, the at least one catalyst is homogenous. In some embodiments, the at least one catalyst comprises platinum. In some embodiments, the at least one catalyst comprises rhodium, ruthenium, or iridium. In some embodiments, the at least one catalyst employs at least one ligand. In some embodiments, the at least one ligand is chiral. In some embodiments, the at least one catalyst employs at least one phosphorus-containing ligand.

In some embodiments, the hydrogenation is enantioselective. Enantioselective hydrogenation can be done using a chiral ligand. In some embodiments, the at least one catalyst employs at least one chiral phosphorus-containing ligand. In some embodiments, the at least one chiral phosphorus-containing ligand is a chiral tertiary diphosphine. In some embodiments, the at least one catalyst employs at least one atropisomeric ligand, such as BINAP, Tol-BINAP, T-BINAP, H8-BINAP, Xyl-BINAP, DM-BINAP, or MeOBiphep. In some embodiments, the at least one catalyst employs at least one segphos-based ligand, such as segphos, dm-segphos, or dtbm-segphos. In some embodiments, the at least one catalyst employs at least one chiral ferrocenyl-based ligand, such as Josiphos, Walphos, Mandyphos, or Taniaphos. Non-limiting examples of BINAP include (R)-(+)-(1,1'-Binaphthalene-2,2'-diyl)bis(diphenylphosphine), (R)-(+)-2,2'-Bis(diphenylphosphino)-1,1'-binaphthalene ((R)-(+)-BINAP), (S)-(−)-(1,1'-Binaphthalene-2,2'-diyl)bis(diphenylphosphine), and (S)-(−)-2,2'-Bis(diphenylphosphino)-1,1'-binaphthalene ((S)-(−)-BINAP)). A non-limiting example of Tol-BINAP is (R)-(+)-2,2'-Bis(di-p-tolylphosphino)-1,1'-binaphthyl. Non-limiting examples of T-BINAP include (S)-(−)-2,2'-p-tolyl-phosphino)-1,1'-binaphthyl, (S)-Tol-BINAP. Examples of H8-BINAP include (R)-(+)-2,2'-Bis(diphenylphospino)-5,5',6,6',7,7',8,8'-octahydro-1,1'-binaphthyl, [(1R)-5,5',6,6',7,7',8,8'-octahydro-[1,1'-binaphthalene]-2,2'-diyl]bis[diphenylphosphine], and (S)-(−)-2,2'-Bis(diphenylphospino)-5,5',6,6',7,7',8,8'-octahydro-1,1'-binaphthyl, [(S)-5,5',6,6',7,7',8,8'-octahydro-[1,1'-binaphthalene]-2,2'-diyl]bis[diphenylphosphine]. Non-limiting examples of DM-BINAP include (R)-(+)-1,1'-Binaphthalene-2,2'-diyl)bis[bis(3,5-dimethylphenyl)phosphine] and (R)-(+)-2,2'-Bis[di(3,5-xylyl)phosphino]-1,1'-binaphthyl. A non-limiting example of Xyl-BINAP is (R)-(+)-XyBINAP and (S)-(+)-XyBINAP available from Takasago International Corp. Non-limiting examples of MeOBiphep include (R)-(6,6'-Dimethoxybiphenyl-2,2'-diyl)bis[bis(3,5-di-tert-butyl-4-methoxyphenyl)phosphine, (S)-(6,6'-Dimethoxybiphenyl-2,2'-diyl)bis[bis(3,5-di-tert-butyl-4-methoxyphenyl)phosphine, (R)-(6,6'-Dimethoxybiphenyl-2,2'-diyl)bis[bis(3,5-di-tert-butylphenyl)phosphine], (S)-(6,6'-Dimethoxybiphenyl-2,2'-diyl)bis[bis(3,5-di-tert-butylphenyl)phosphine], (R)-(6,6'-Dimethoxybiphenyl-2,2'-diyl)bis{bis[3,5-diisopropyl-4-(dimethylamino)phenyl]phosphine}, (S)-(6,6'-Dimethoxybiphenyl-2,2'-diyl)bis{bis[3,5-diisopropyl-4-(dimethylamino)phenyl]phosphine}, (R)-(6,6'-Dimethoxybiphenyl-2,2'-diyl)bis[bis(3,5-dimethylphenyl)phosphine], (S)-(6,6'-Dimethoxybiphenyl-2,2'-diyl)bis[bis(3,5-dimethylphenyl)phosphine], (R)-(6,6'-Dimethoxybiphenyl-2,2'-diyl)bis[bis(4-methylphenyl)phosphine], (S)-(6,6'-Dimethoxybiphenyl-2,2'-diyl)bis[bis(4-methylphenyl)phosphine], (R)-(6,6'-Dimethoxybiphenyl-2,2'-diyl)bis[bis(3,4,5-trimethoxyphenyl)phosphine], (S)-(6,6'-Dimethoxybiphenyl-2,2'-diyl)bis[bis(3,4,5-trimethoxyphenyl)phosphine], (R)-(6,6'-Dimethoxybiphenyl-2,2'-diyl)bis(di-2-furylphosphine), (S)-(6,6'-Dimethoxybiphenyl-2,2'-diyl)bis(di-2-furylphosphine), (R)-(6,6'-Dimethoxybiphenyl-2,2'-diyl)bis(diisopropylphosphine), (S)-(6,6'-Dimethoxybiphenyl-2,2'-diyl)bis(diisopropylphosphine), (R)-(+)-(6,6'-Dimethoxybiphenyl-2,2'-diyl)bis(diphenylphosphine), and (S)-(−)-(6,6'-Dimethoxybiphenyl-2,2'-diyl)bis(diphenylphosphine). Non-limiting examples of segphos include (R)-(+)-5,5'-Bis(diphenylphosphino)-4,4'-bi-1,3-benzodioxole (or [4(R)-(4,4'-bi-1,3-benzodioxole)-5,5'-diyl]bis[diphenylphosphine]) and (S)-(−)-5,5'-Bis(diphenylphosphino)-4,4'-bi-1,3-benzodioxole. Non-limiting examples of dtbm-segphos include (R)-(−)-5,5'-Bis[di(3,5-di-tert-butyl-4-methoxyphenyl)phosphino]-4,4'-bi-1,3-benzodioxole (or [(4R)-(4,4'-bi-1,3-benzodioxole)-5,5'-diyl]bis[bis(3,5-di-tert-butyl-4-methoxyphenyl)phosphine]) and (S)-(+)-5,5'-Bis[di(3,5-di-tert-butyl-4-methoxyphenyl)phosphino]-4,4'-bi-1,3-benzodioxole. Examples of dm-segphos include (S)-(+)-5,5'-Bis[di(3,5-di-tert-butyl-4-methoxyphenyl)phosphino]-4,4'-bi-1,3-benzodioxole and (R)-(+)-5,5'-Bis[di(3,5-xylyl)phosphino]-4,4'-bi-1,3-benzodioxole (or [(4R)-(4,4'-bi-1,3-benzodioxole)-5,5'-diyl]bis[bis(3,5-dimethylphenyl)phosphine]). Non-limiting examples of chiral ferrocenyl-based ligands can be found in US 2015/0045556 (the chiral ligand descriptions of which are incorporated herein by reference). Non-limiting examples chiral ferrocenyl-based ligands include:

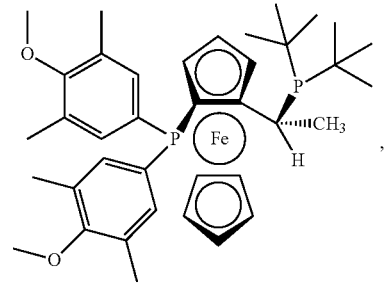

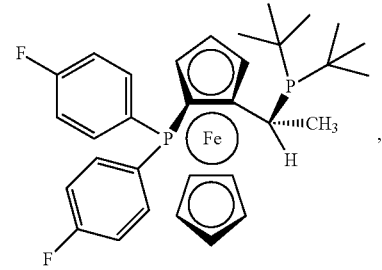

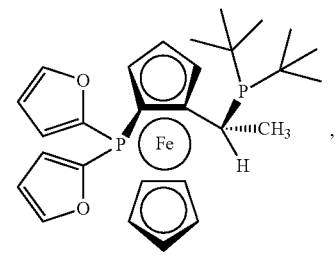

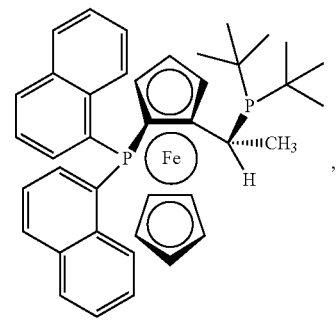

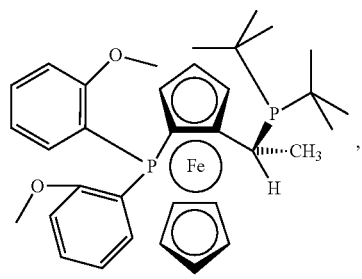

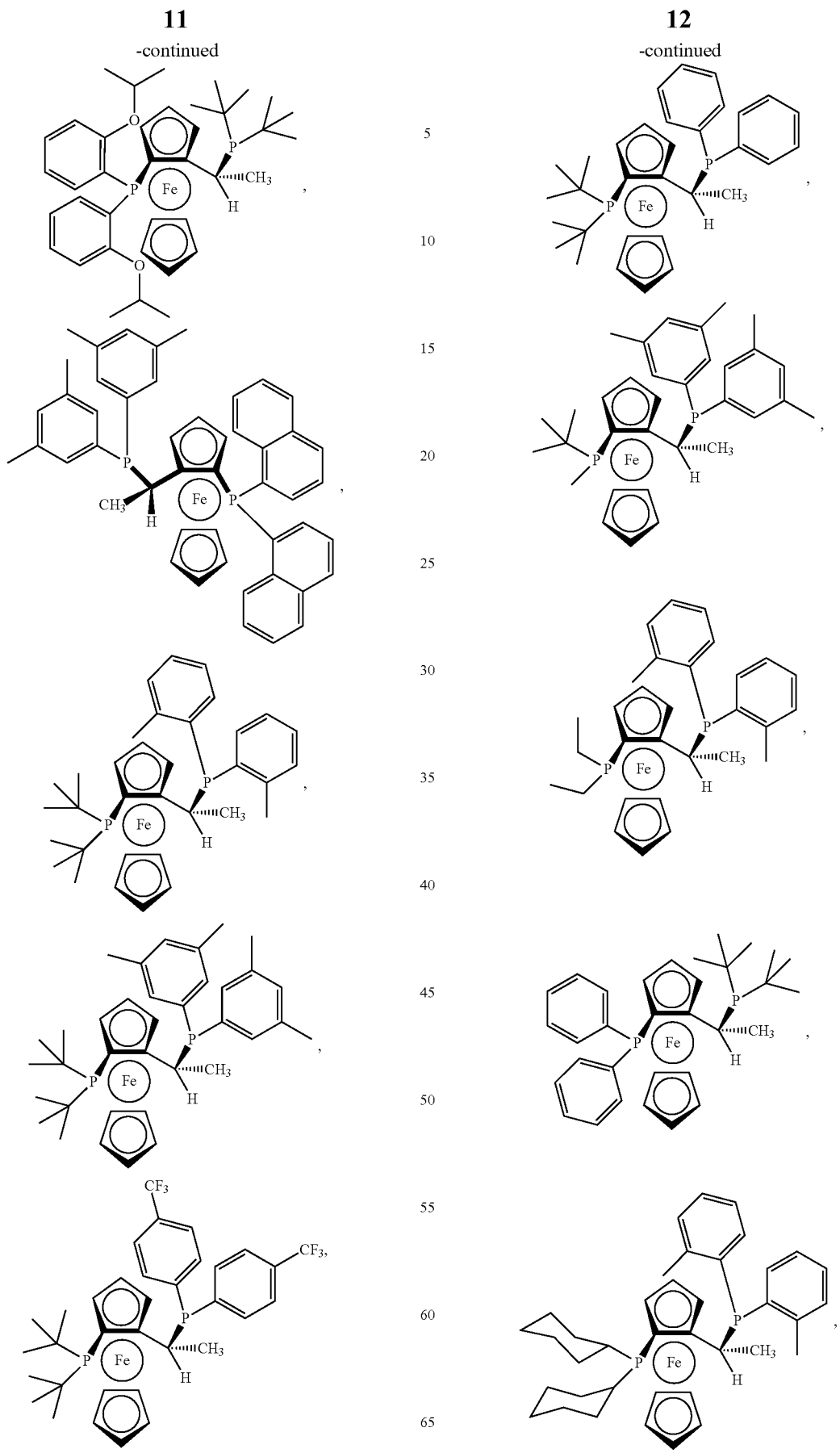

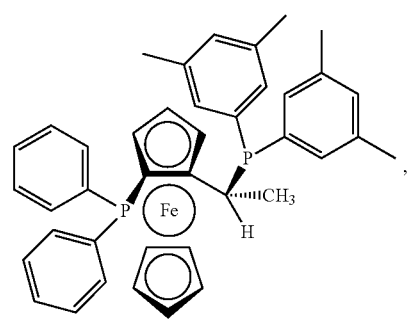
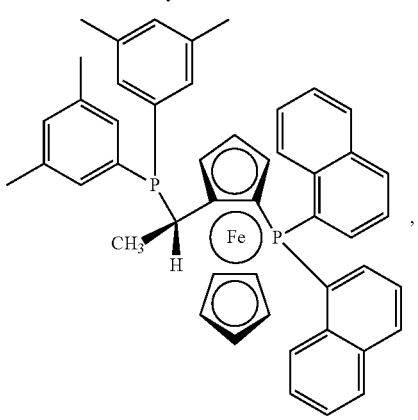
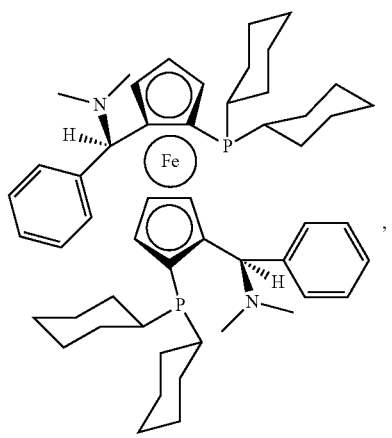
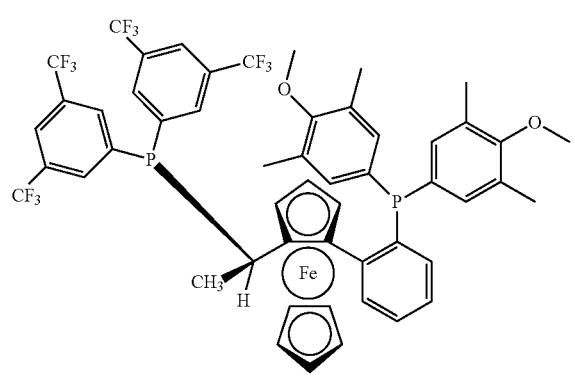
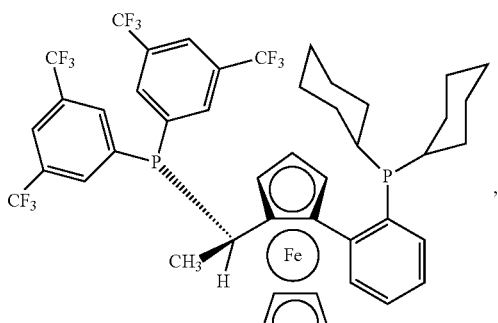
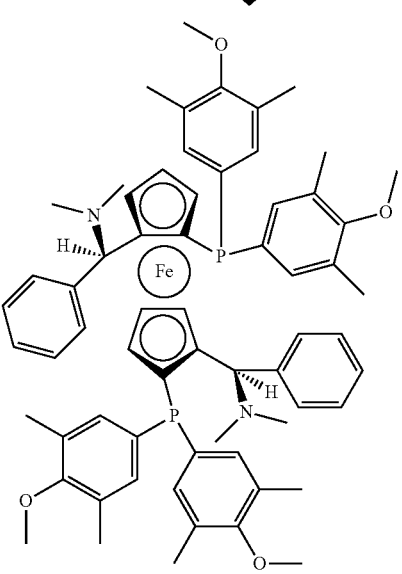
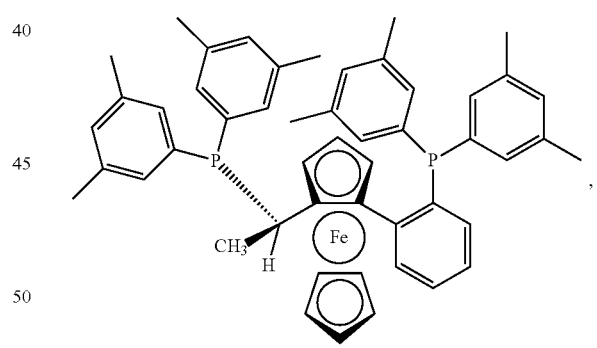
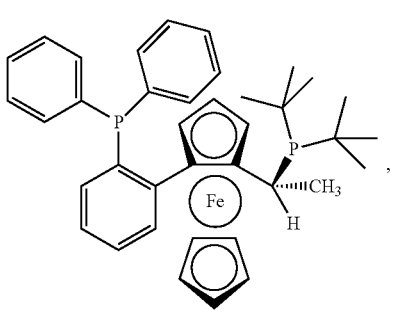

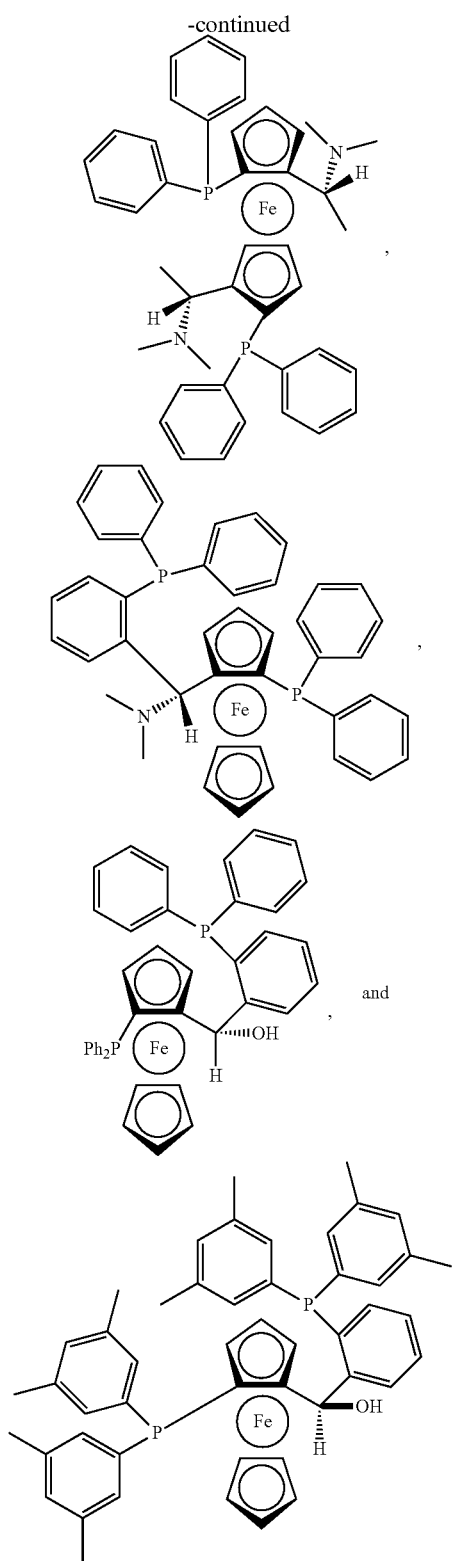

In some embodiments, the hydrogenation is carried out in the presence of at least one chiral ligand. In some embodiments, the at least one chiral ligand is chosen from phosphine ligands, BINOL, TADDOL, BOX, DuPhos, DiPAMP, BINAP, Tol-BINAP, T-BINAP, H8-BINAP, DM-BINAP, Xyl-BINAP, MeOBiphep, DIOP, PHOX, PyBox, SALENs, SEGPHOS, DM-SEGPHOS, DTBM-SEGPHOS, JOSI-PHOS, MANDYPHOS, WALPHOS, TANIAPHOS, sPHOS, xPHOS, SPANphos, Triphos, Xantphos, and Chiraphos ligands. In some embodiments, the at least one chiral ligand is a SEGPHOS ligand. In some embodiments, the at least one chiral ligand is a MANDYPHOS ligand. In some embodiments, the at least one chiral ligand is a MANDYPHOS SL-M004-1 available from, for example, Solvias. In some embodiments, the at least one chiral ligand is chosen from the following:

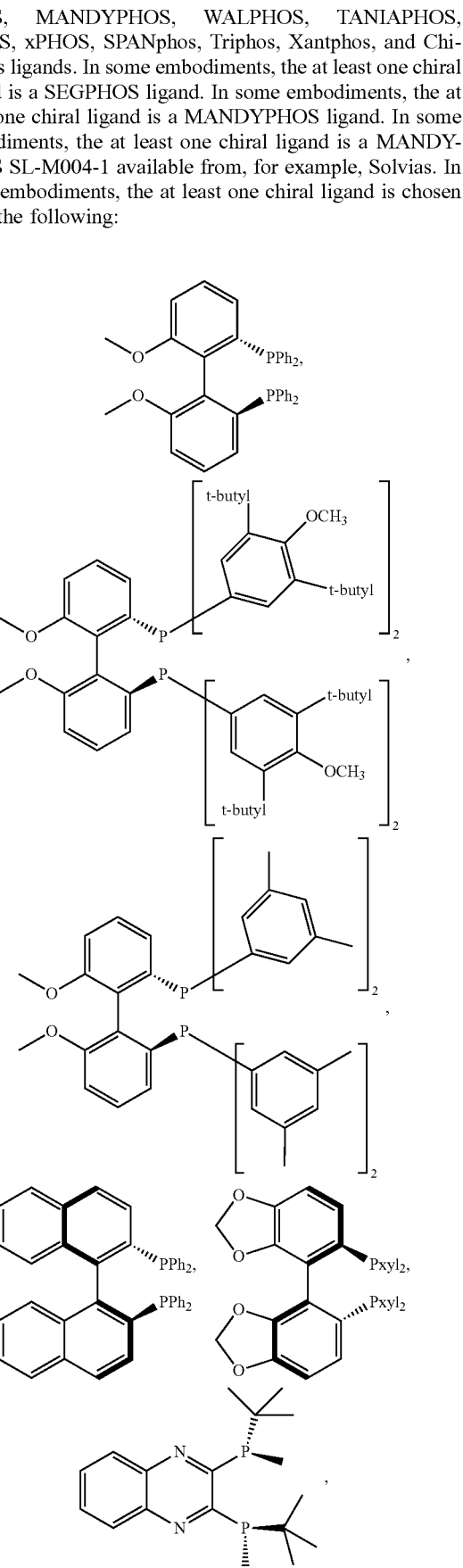

-continued
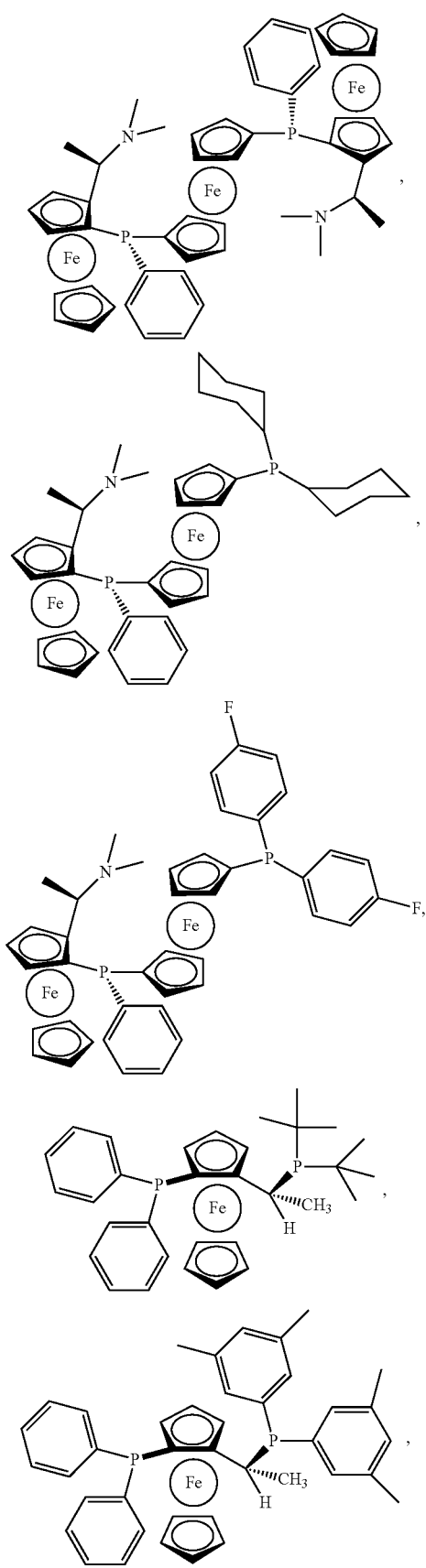
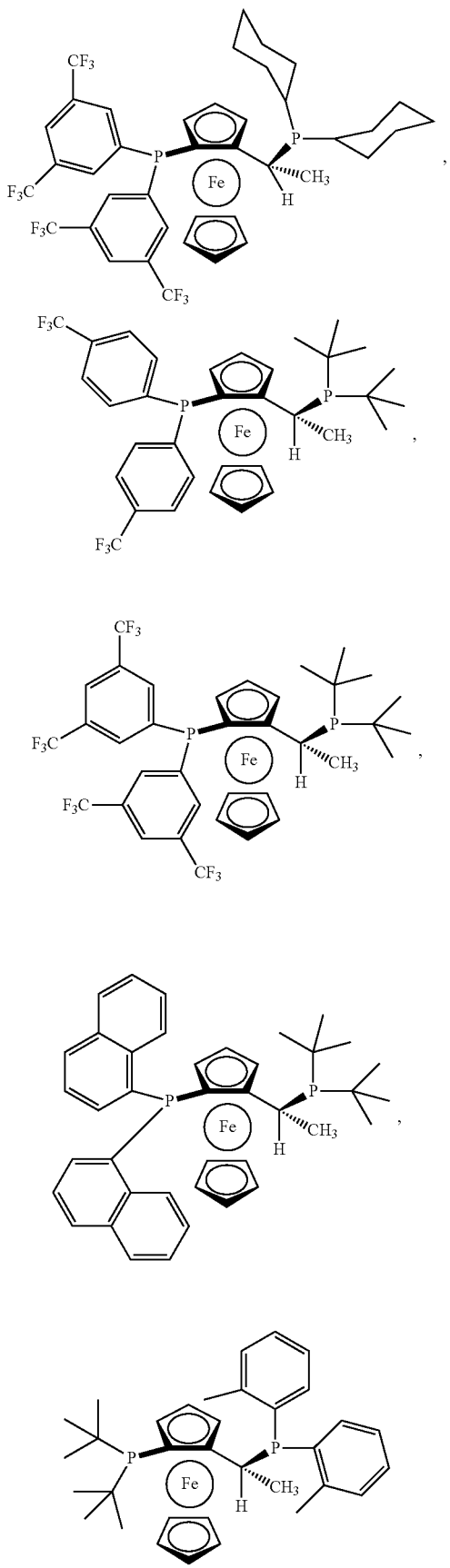

-continued
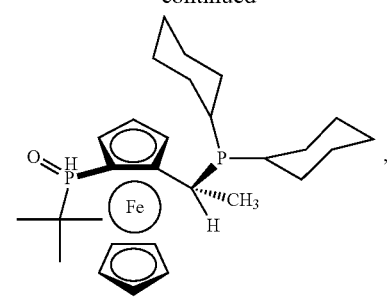
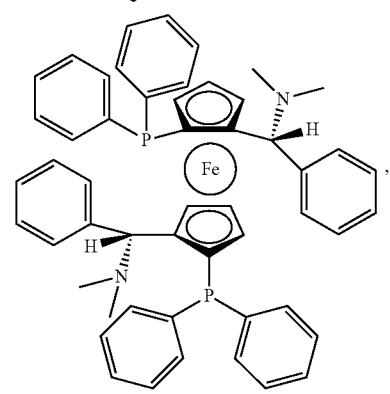
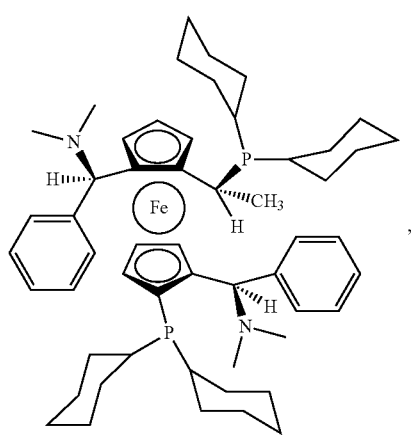
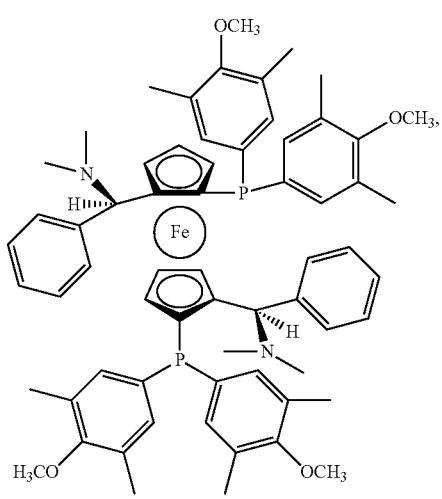
-continued
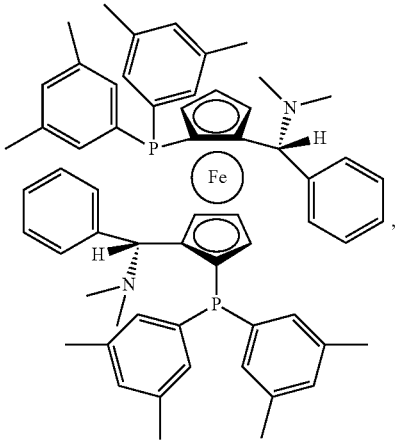
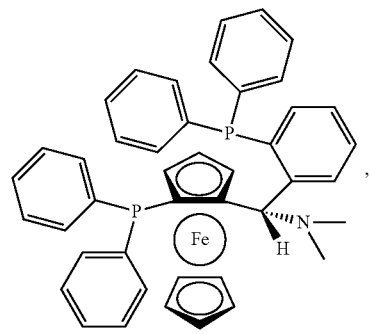
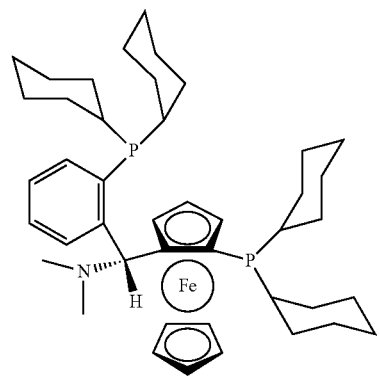
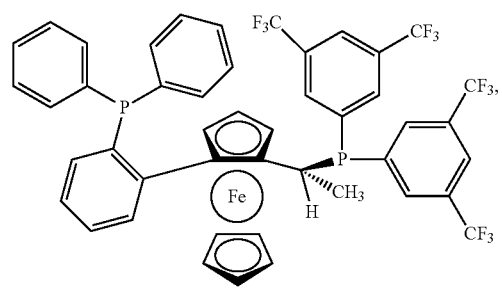

-continued

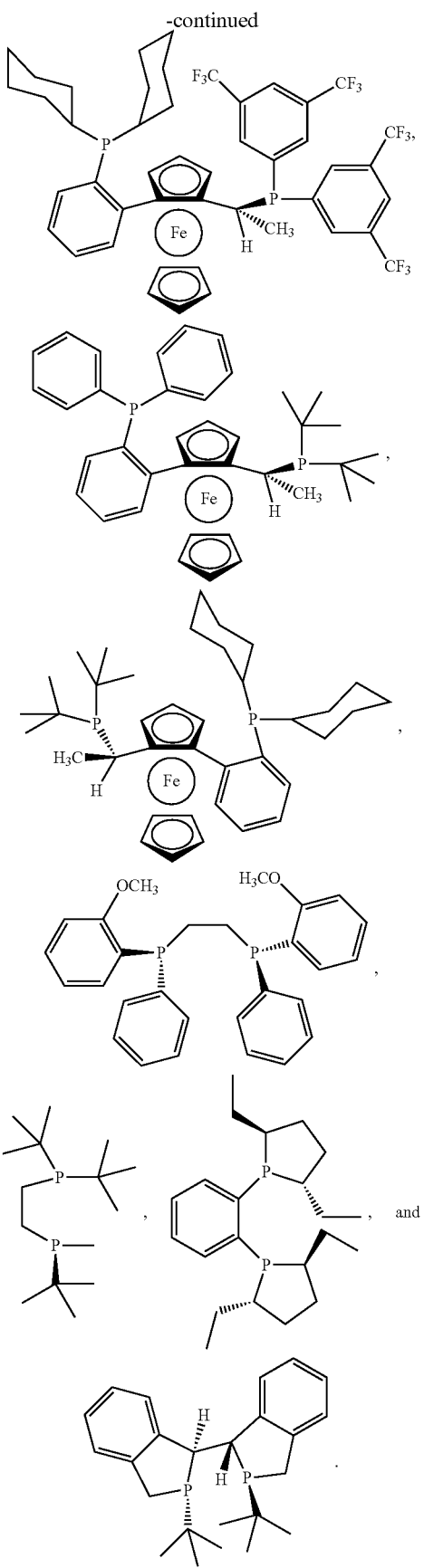

In some embodiments, the hydrogenation is carried out in the presence of at least one transition metal. In some embodiments, the at least one transition metal is chosen from the platinum group metals. In some embodiments, the at least one transition metal is chosen from rhodium, ruthenium, rhenium, and palladium. In some embodiments, the at least one transition metal is ruthenium. In some embodiments, the at least one transition metal is rhodium.

In some embodiments, hydrogenation is carried out in the presence of at least one catalyst chosen from: [Rh(nbd)Cl]$_2$; [Rh(COD)$_2$OC(O)CF$_3$]; [Rh(COD)(Ligand A)BF$_4$; [Rh(COD)(Ligand B)BF$_4$; [Rh(COD)(Ligand C)BF$_4$; and [Rh(COD)(Ligand D)BF, wherein COD is 1,5-cyclooctadiene; Ligand A is

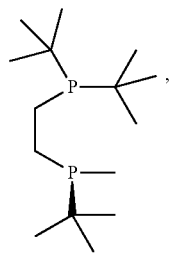 [SMILES: C[P@](CCP(C(C)(C)C)C(C)(C)C)C(C)(C)C]

Ligand B is:

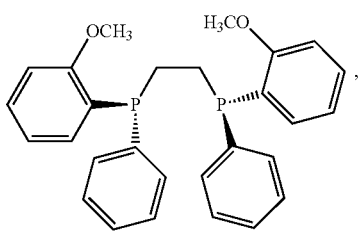

Ligand C is

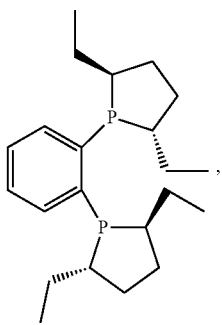 [SMILES: CC[C@H]1CC[C@H](CC)P1c1ccccc1P1[C@@H](CC)CC[C@@H]1CC]

and Ligand D is

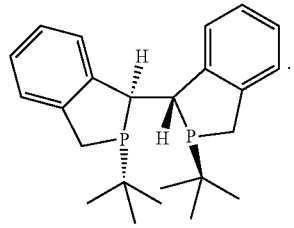

In some embodiments, hydrogenation is carried out in the presence of at least one catalyst chosen from: [Ru(COD)₂Me-allyl)₂]BF₄, [RuC(p-cymene){(R)-segphos}]Cl; [RuCl(p-cymene){(R)-binap}]Cl; Ru(OAc)₂[(R)-binap]; [NH₂Me₂][{RuCl[(R)-binap]}₂(μ-Cl)₃]; [RuCl(p-cymene){(R)-Xyl-binap}]Cl; [NH₂Me₂][{RuCl[(R)-Xyl-binap]}₂(μ-Cl)₃]; [RuCl(p-cymene){(R)—H8-binap}]Cl; [NH₂Me₂][{RuCl[(R)—H8-binap]}₂(μ-Cl)₃]; [NH₂Me₂][{RuCl[(R)-segphos]}₂(μ-Cl)₃]; [NH₂Me₂][{RuCl[(R)-dm-segphos]}₂(μ-Cl)₃]; [RuCl(p-cymene){(R)-dtbm-segphos}]Cl, wherein p-cymene is 1-methyl-4-(propan-2-yl)benzene, Me-allyl is 2-methylallyl, and OAC is acetate. In some embodiments, hydrogenation is carried out in the presence of [RuCl(p-cymene){(R)-segphos}]Cl. In some embodiments, hydrogenation is carried out in the presence of [Ru(COD)₂Me-allyl)₂]BF₄. In some embodiments, hydrogenation is carried out in the presence of [RuC(p-cymene){(R)-segphos}]Cl; [RuC(p-cymene){(R)-binap}]Cl; and/or [NH₂Me₂][{RuCl[(R)-segphos]}2(μ-Cl)₃].

In some embodiments, the hydrogenation is carried out in the presence of at least one catalyst prepared in situ with a metal precursor and a ligand. In some embodiments, the at least one ligand is chosen from chiral ligands set forth above. In some embodiments, the at least one ligand is chosen from:

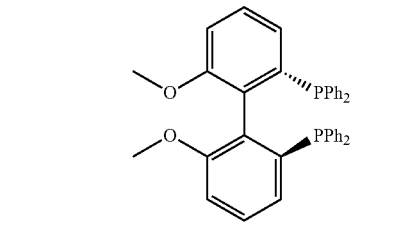

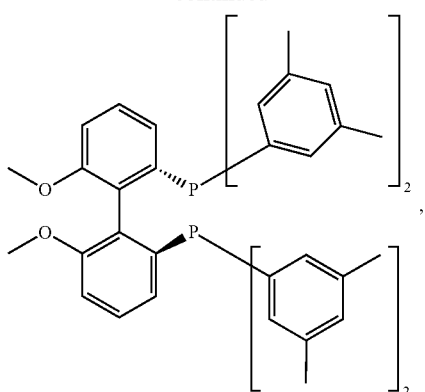

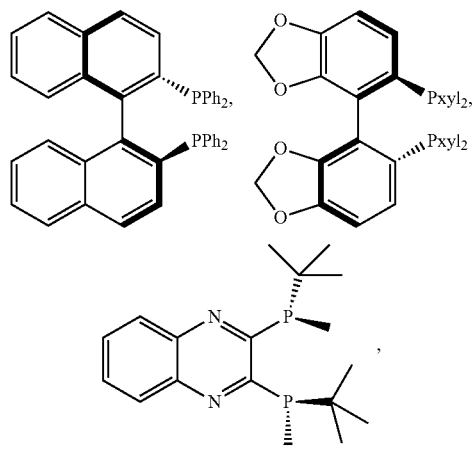

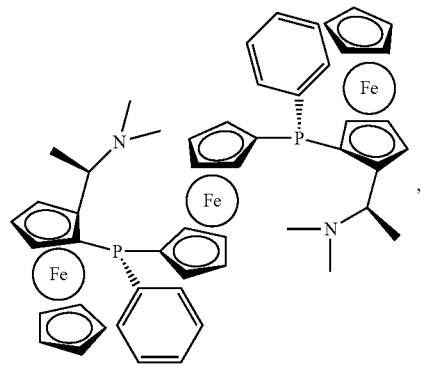

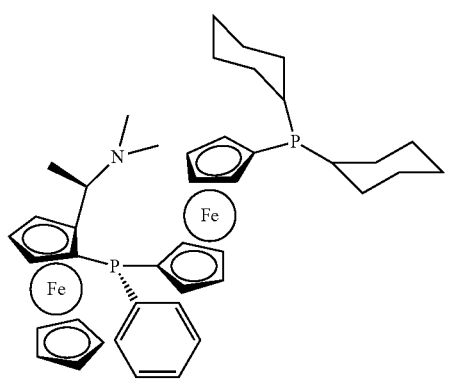

-continued
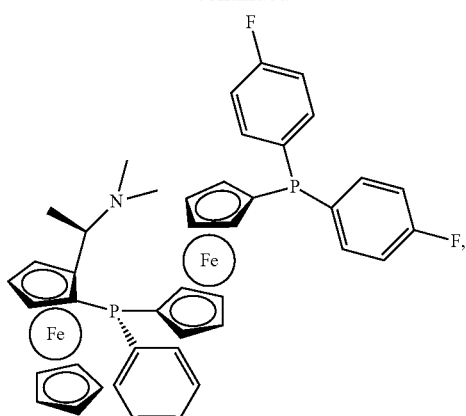
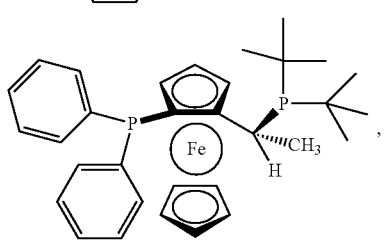
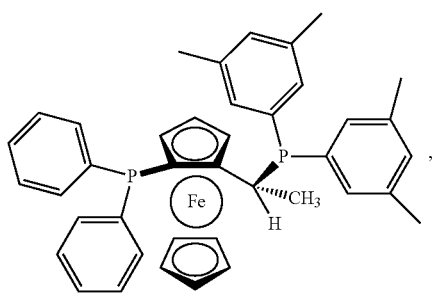
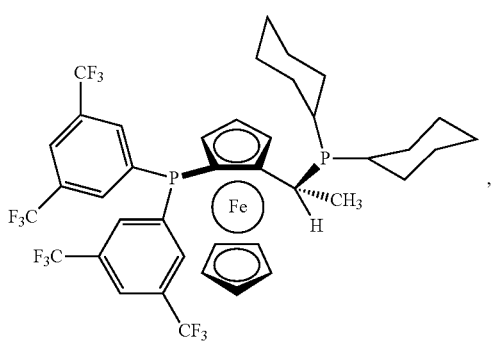
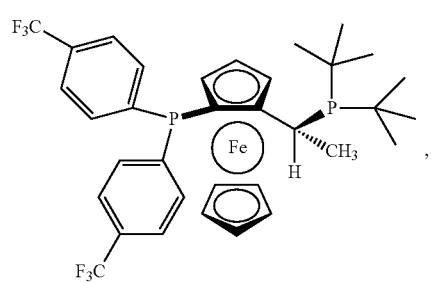
-continued
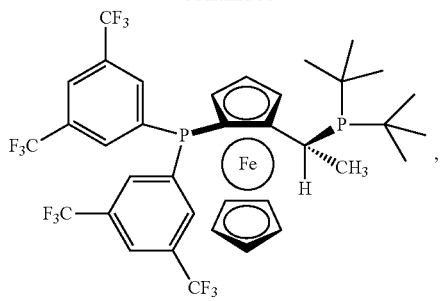
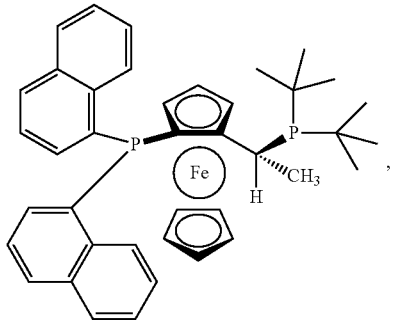
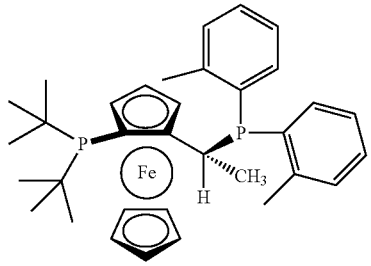
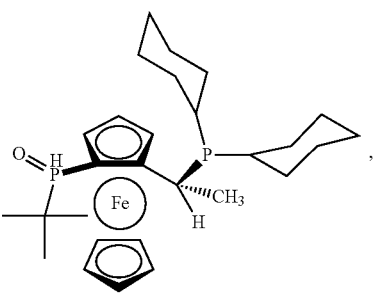
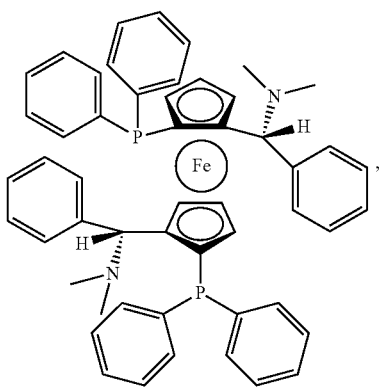

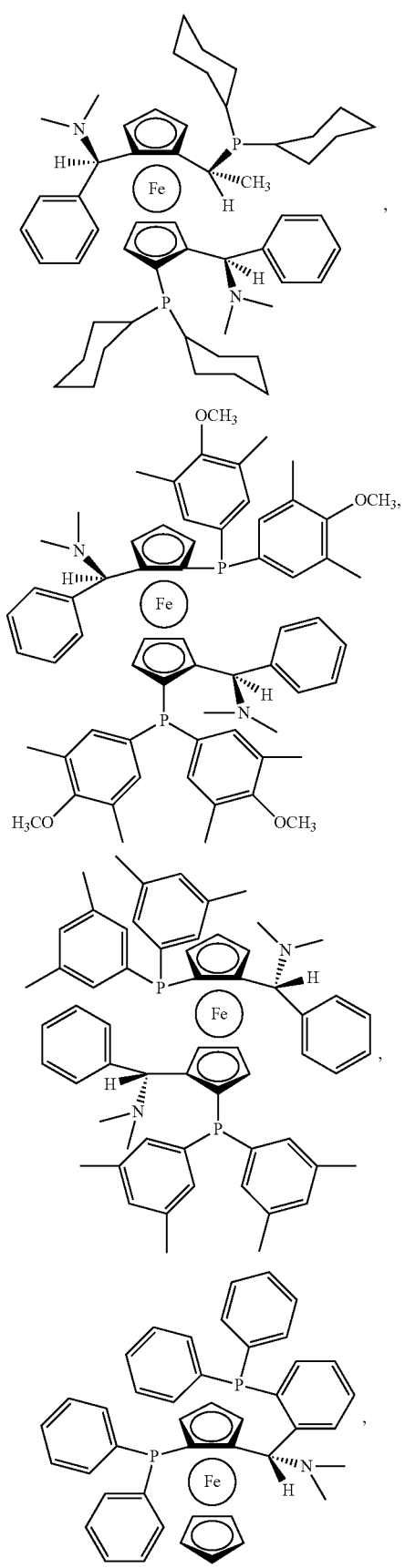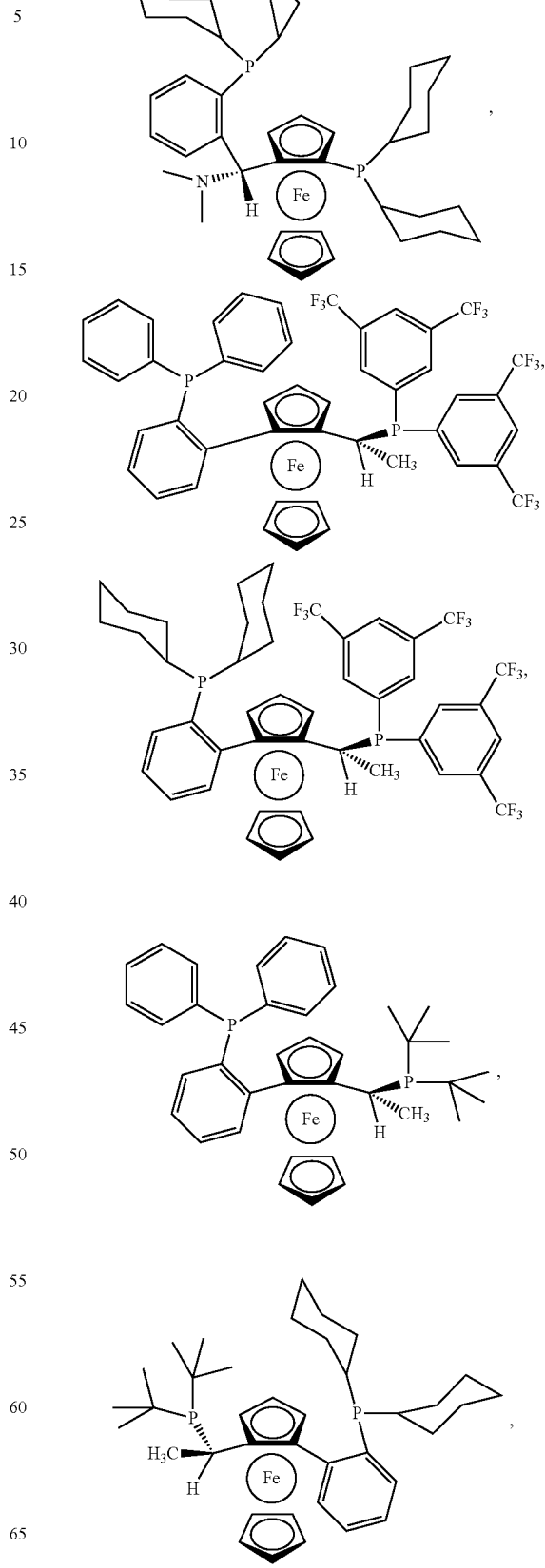

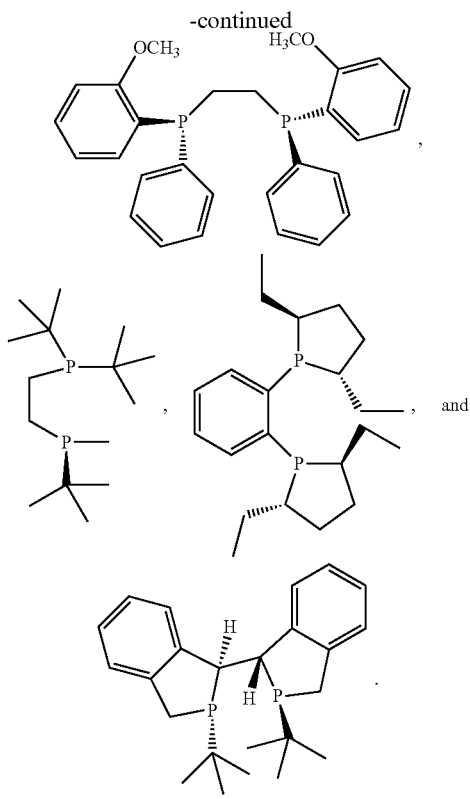

In some embodiments, at least one metal precursor is chosen from [Rh(nbd)Cl]$_2$; [Rh(COD)$_{20}$C(O)CF$_3$]; [Rh(COD)(Ligand A)BF$_4$; [Rh(COD)(Ligand B)BF$_4$; [Rh(COD)(Ligand C)BF$_4$; [Rh(COD)(Ligand D)BF$_4$, [Ru(COD)(OC(O)CF$_3$)$_2$], [Ru(COD)Me-allyl)$_2$], [Rh(COD)(Ligand A)BF$_4$; [Rh(COD)(Ligand B)BF$_4$; [Rh(COD)(Ligand C)BF$_4$, and [Rh(COD)(Ligand D)BF.

In some embodiments, the hydrogenation is carried out at a temperature of 10° C. to 70° C. In some embodiments, hydrogenation is carried out at a temperature of 30° C. to 50° C. In some embodiments, hydrogenation is carried out at 45° C. In some embodiments, hydrogenation is carried out at 30° C.

Reaction (d)—Reducing (S)- or (R)-3,5,5-trimethyl-pyrrolidin-2-one to Produce Free Base or Salts of (S)- or (R)-2,2,4-trimethylpyrrolidine, Respectively In some embodiments, the disclosed process comprises reducing (S)- or (R)-3,5,5-trimethyl-pyrrolidin-2-one to produce (S)- or (R)-2,2,4-trimethylpyrrolidine, respectively. In some embodiments, the reduction is performed in the presence of at least one reducing agent. In some embodiments, the at least one reducing agent is a hydride. In some embodiments, the hydride is chosen from lithium aluminum hydride, lithium aluminum deuteride, sodium bis(2-methoxyethoxy)aluminumhydride, and borane. In some embodiments, 1-2 equivalents of hydride are added. In some embodiments, the reducing agent is lithium aluminum hydride.

In some embodiments, the reduction is carried out at 40° C. to 100° C. In some embodiments, the reduction is carried out at 40° C. to 80° C. In some embodiments, the reduction is carried out at 50° C. to 70° C. In some embodiments, the reduction is carried out at 68° C.

In some embodiments, the reducing agent is hydrogen gas. In some embodiments, the reduction is carried out in the presence of one or more catalysts and hydrogen gas. In some embodiments, the reduction is carried out in the presence of one or more metallic catalysts and hydrogen gas. In some embodiments, the reduction is carried out under a catalytic hydrogenation condition in the presence of one or more catalysts and hydrogen gas. In some embodiments, the catalyst is chosen from Pt, Co, Sn, Rh, Re, and Pd. In some embodiments, the reduction is carried out in the presence of hydrogen gas and one or more catalysts chosen from Pt, Co, Sn, Rh, Re, and Pd. In some embodiments, the reduction is carried out in the presence of hydrogen gas and one or more monometallic or bimetallic catalysts chosen from Pt, Pd, Pt—Re, Pt—Co, Pt—Sn, Pd—Re, and Rh—Re. Any suitable amounts of such catalysts can be used for the reduction. In some embodiments, 0.1 wt %-5 wt % of such catalysts can be used. In some embodiments, such catalysts are used in one or more support materials selected from TiO$_2$, SiO$_2$, Al$_2$O$_3$(e.g., theta-Al$_2$O$_3$ or gamma-Al$_2$O$_3$), and zeolite. In some embodiments, the reduction is carried out in the presence of hydrogen gas and one or more monometallic or bimetallic catalysts chosen from Pt—Sn in TiO$_2$ (or Pt—Sn/TiO$_2$), Pt—Re in TiO$_2$ (or Pt—Re/TiO$_2$), Pt in TiO$_2$ (or Pt/TiO$_2$), Rh in TiO$_2$ (or Rh/TiO$_2$), Rh—Re in TiO$_2$ (or Rh—Re/TiO$_2$), Pt—Sn in theta-Al$_2$O$_3$ (or Pt—Sn/theta-Al$_2$O$_3$), Pt—Sn in SiO$_2$ (or Pt—Sn/SiO$_2$), and Pt—Sn in TiO$_2$ (or Pt—Sn/TiO$_2$). In some embodiments, the reduction is carried out in the presence of hydrogen gas and one or more monometallic or bimetallic catalysts chosen from 4 wt % Pt-2 wt % Sn in TiO$_2$ (or 4 wt % Pt-2 wt % Sn/TiO$_2$), 4 wt % Pt-2 wt % Re in TiO$_2$ (or 4 wt % Pt-2 wt % Re/TiO$_2$), 4 wt % Pt in TiO$_2$ (or 4 wt % Pt/TiO$_2$), 4 wt % Rh in TiO$_2$ (or 4 wt % Rh/TiO$_2$), 4 wt % Rh-2% Re in TiO$_2$ (or 4 wt % Rh-2 wt % Re/TiO$_2$), 4 wt % Pt-2 wt % Sn in theta-Al$_2$O$_3$ (or 4 wt % Pt-2 wt % Sn/theta-Al$_2$O$_3$), 4 wt % Pt-2 wt % Sn in SiO$_2$ (or 4 wt % Pt-2 wt % Sn/SiO$_2$), 2 wt % Pt-0.5 wt % Sn in SiO$_2$ (or 2 wt % Pt-0.5 wt % Sn/SiO$_2$), 2 wt % Pt-0.5 wt % Sn in TiO$_2$ (or 2 wt % Pt-0.5 wt % Sn/TiO$_2$), and 2 wt % Pt-8 wt % Sn in TiO$_2$ (or 2 wt % Pt-8 wt % Sn/TiO$_2$).

In some embodiments, the reducing agent is quenched after reaction. In some embodiments, the reducing agent is quenched by sodium sulfate. In some embodiments, the reducing agent is quenched by water and then 15 wt % KOH in water.

In some embodiments, the product from the reduction step with a hydride is further treated with acid to produce a salt.

In some embodiments, the acid is chosen from hydrochloric acid, hydrobromic acid, phosphoric acid, sulfuric acid, oxalic acid, citric acid, a tartaric acid (e.g., L- or D-tartaric acid or dibenzoyl tartaric acid), a malic acid (e.g., L- or D-malic acid), a maleic acid (e.g., L- or D-maleic acid, 4-bromo-mandelic acid or 4-bromo-mandelic acid), a tartranilic acid (e.g., L- or D-tartranilic acid, (2,3)-2'-methoxy-tartranilic acid), a mandelic acid (e.g., L- or D-mandelic acid, 4-methyl-mandelic acid. O-acetyl mandelic acid or 2-chloromandelic acid), a tartaric acid (e.g., L- or D-mandelic acid, di-p-toluoyltartaric acid, di-p-anisoyltartaric acid), acetic acid, alpha-methoxy-phenyl acetic acid, a lactic acid (e.g., L- or D-lactic acid, 3-phenyllactic acid), a phenylalanine (e.g., N-acetyl-phenylalanine, Boc-homophenyl-alanine, or Boc-phenylalanine), a glutamic acid (e.g., L- or D-glutamic acid or pyroglutamic acid), phencyphos hydrate, chlocyphos, camphor sulfonic acid, camphoric acid, anisy-phos, 2-phenylpropionic acid, N-acetyl-leucine, BINAP phosphate, N-acetyl-proline, α-hydroxyisovaleric acid, phenylsuccinic acid, and/or naproxen.

In some embodiments, the reduction and acid treatment reactions are performed without isolation of the reduction product. In some embodiments, (R)-3,5,5-trimethyl-pyrrolidin-2-one is reacted with a hydride and then with an acid to produce an (R)-2,2,4-trimethylpyrrolidine salt. In some embodiments, (S)-3,5,5-trimethyl-pyrrolidin-2-one is reacted with a hydride and then with an acid to produce an (S)-2,2,4-trimethylpyrrolidine salt.

In some embodiments, the reduction step product (e.g. (S)- or (R)-2,2,4-trimethylpyrrolidine) is isolated before the acid treatment step. In some embodiments, (S)-2,2,4-trimethylpyrrolidine is treated with an acid to produce a salt of (S)-2,2,4-trimethylpyrrolidine. In some embodiments, (R)-2,2,4-trimethylpyrrolidine is treated with an acid to produce a salt of (R)-2,2,4-trimethylpyrrolidine.

In Scheme 1 above, the piperidone ring of Compound 2 is contracted and acid is added to promote formation of predominantly Compound 3. The olefin group of Compound 3 is hydrogenated in the presence of chiral ligands to produce Compound 4S in (S) configuration. The carbonyl group of Compound 4S is reduced to form Compound 1S. The (S) configuration of Compound 4S is retained in Compound 1S. In Scheme 2 above, the piperidone ring of Compound 2 is contracted and acid is added to promote formation of predominantly Compound 3. The olefin group of Compound 3 is hydrogenated in the presence of chiral ligands to produce Compound 4R in (R) configuration. The carbonyl group of Compound 4R is reduced to form Compound 1R. The (R) configuration of Compound 4R is retained in Compound 1R.

In some embodiments, Compound 2 is commercially available. In some embodiments, contraction of piperidone ring of Compound 2 to yield pyrrolidine of Compound 3 is carried out in the presence of NaOH and tri-butyl methyl ammonium chloride. In some embodiments, the reaction is further treated with hydrochloric acid to promote predominantly Compound 3.

In some embodiments, Compound 3 undergoes enantioselective hydrogenation in the presence of chiral ruthenium catalysts with phosphine ligands.

In some embodiments, Compound 4S or 4R is reduced with lithium aluminum hydride. In some embodiments, Compound 4S or 4R is reduced with lithium aluminum deuteride.

Unless otherwise indicated, structures depicted herein are also meant to include compounds that differ only in the presence of one or more isotopically enriched atoms. For example, Compounds 1S, 1R, 3, 4S, and 4R, wherein one or more hydrogen atoms are replaced with deuterium or tritium, or one or more carbon atoms are replaced by a $^{13}$C- or $^{14}$C-enriched carbon are within the scope of this invention. In some embodiments, Compounds 1S, 1R, 3, 4S, and 4R, wherein one or more hydrogen atoms are replaced with deuterium are prepared by the methods described herein. Such compounds are useful, for example, as analytical tools, probes in biological assays, or compounds with improved therapeutic profile.

A listing of exemplary embodiments includes:
1. A process for preparing (S)-2,2,4-trimethylpyrrolidine or a salt thereof comprising:
(a) reacting 2,2,6,6-tetramethyl-piperidin-4-one or a salt thereof with chloroform and at least one base;
(b) reacting the products of the reaction in (a) with an acid to produce 5,5-dimethyl-3-methylenepyrrolidin-2-one;
(c) hydrogenating 5,5-dimethyl-3-methylenepyrrolidin-2-one to produce (S)-3,5,5-trimethyl-pyrrolidin-2-one;
(d) reducing (S)-3,5,5-trimethyl-pyrrolidin-2-one to produce (S)-2,2,4-trimethylpyrrolidine; and
(e) optionally treating (S)-2,2,4-trimethylpyrrolidine with acid to produce a salt of (S)-2,2,4-trimethylpyrrolidine.
2. The process according to embodiment 1, further comprising treating (S)-2,2,4-trimethylpyrrolidine with HCl to generate (S)-2,2,4-trimethylpyrrolidine hydrochloride.
3. The process according to embodiment 1 or 2, wherein said at least one base is chosen from potassium t-butoxide, potassium hydroxide, and sodium hydroxide.
4. The process according to embodiment 1 or 2, wherein said at least one base is sodium hydroxide.
5. The process according to embodiment 1 or 2, wherein from 3 to 15 molar equivalents of said at least one base relative to the mole of 2,2,6,6-tetramethylpiperidin-4-one are added for the reaction in (a).
6. The process according to embodiment 5, wherein from 5 to 12 molar equivalents of said at least one base are added.
7. The process according to embodiment 5, wherein 7.5 molar equivalents of said at least one base are added.
8. The process according to embodiment 5, wherein 10 molar equivalents of said at least one base are added.
9. The process according to embodiment 5, wherein 8 molar equivalents of sodium hydroxide are added.
10. The process according to embodiment 1 or 2, wherein said at least one base added for the reaction in (a) is in the form of an aqueous solution having a concentration ranging from 20 wt % to 80 wt % relative to the total weight of said aqueous solution.
11. The process according to embodiment 1 or 2, wherein said at least one base is 20 wt % aqueous NaOH.
12. The process according to embodiment 1 or 2, wherein said at least one base is 40 wt % aqueous NaOH.
13. The process according to embodiment 1 or 2, wherein said at least one base is 50 wt % aqueous NaOH.
14. The process according to any one of embodiments 1-13, wherein said chloroform is present in an amount ranging from 1 to 4 molar equivalents relative to the mole of 2,2,6,6-tetramethylpiperidin-4-one.
15. The process according to embodiment 14, wherein said chloroform is present in an amount ranging from 1.5 to 3.5 molar equivalents relative to the mole of 2,2,6,6-tetramethylpiperidin-4-one.
16. The process according to embodiment 14, wherein said chloroform is present in an amount of 1.75 molar equivalents relative to the mole of 2,2,6,6-tetramethylpiperidin-4-one.
17. The process according to any one of embodiments 1-16, wherein said 2,2,6,6-tetramethyl-piperidin-4-one or a salt thereof is reacted with chloroform, at least one base, and at least one phase transfer catalyst.
18. The process according to any one of embodiments 1-17, wherein at least one phase transfer catalyst is chosen from tetraalkylammonium salts and crown ethers.
19. The process according to embodiment 18, wherein said at least one phase transfer catalyst is chosen from tetraalkylammonium salts.
20. The process according to embodiment 18, wherein said at least one phase transfer catalyst is chosen from tetraalkylammonium halides.
21. The process according to embodiment 18, wherein said at least one phase transfer catalyst is chosen from tributylmethylammonium chloride, tributylmethylammonium bromide, tetrabutylammonium bromide (TBAB), tetrabutylammonium chloride (TBAC), tetrabutylammonium iodide (TBAI), tetrabutylammonium hydroxide (TBAH), benzyltrimethylammonium chloride, tetraoctylammonium bromide (TAOB), tetraoctylammonium chloride (TAOC), tetraoctylammonium iodide (TAOI), trioctylmethylammonium chloride, and trioctylmethylammonium bromide.

22. The process according to any one of embodiments 17-21, wherein from 0.01 molar equivalents to 0.2 molar equivalents of said at least one phase transfer catalyst relative to the mole of 2,2,6,6-tetramethylpiperidin-4-one is added to the reaction in (a).

23. The process according to embodiment 22, wherein from 0.02 molar equivalents to 0.1 molar equivalents of said at least one phase transfer catalyst relative to the mole of 2,2,6,6-tetramethylpiperidin-4-one is added.

24. The process according to embodiment 23, wherein from 0.03 molar equivalents to 0.06 molar equivalents of said at least one phase transfer catalyst relative to the mole of 2,2,6,6-tetramethylpiperidin-4-one is added.

25. The process according to any one of embodiments 1-24, wherein said acid of the reaction in (b) is chosen from aqueous solutions of protic acids.

26. The process according to embodiment 25, wherein said protic acids are chosen from hydrochloric acid, methane sulfonic acid, triflic acid, and sulfuric acid.

27. The process according to embodiment 25, wherein the concentration of said aqueous solutions of protic acids range from 1M to 18M.

28. The process according to embodiment 27, wherein the concentration of said aqueous solutions of protic acids range from 2M to 10M.

29. The process according to embodiment 28, wherein said acid of the reaction in (b) is chosen from HCl having a concentration ranging from 2M to 3M.

30. The process according to embodiment 29, wherein said acid of the reaction in (b) is chosen from 2M HCl.

31. The process according to embodiment 29, wherein said acid of the reaction in (b) is chosen from 2.5M HCl.

32. The process according to embodiment 29, wherein said acid of the reaction in (b) is chosen from 3M HCl.

33. The process according to any one of embodiments 1-32, wherein 0.5 to 10 molar equivalents of said acid relative to the mole of 2,2,6,6-tetramethylpiperidin-4-one are added to the reaction in (b).

34. The process according to embodiment 33, wherein 1 to 4 molar equivalents of said acid relative to the mole of 2,2,6,6-tetramethylpiperidin-4-one are added to the reaction in (b).

35. The process according to embodiment 33, wherein 1.5 molar equivalents of said acid relative to the mole of 2,2,6,6-tetramethylpiperidin-4-one are added to the reaction in (b).

36. The process according to embodiment 1 or 2, wherein a yield of 5,5-dimethyl-3-methylenepyrrolidin-2-one produced from the reactions in (a) and (b) ranges from 40% to 70% relative to the mole of 2,2,6,6-tetramethylpiperidin-4-one.

37. The process according to any one of embodiments 1-36, wherein said hydrogenating reaction in (c) comprises reacting 5,5-dimethyl-3-methylenepyrrolidin-2-one with at least one catalyst and hydrogen gas to produce (S)-3,5,5-trimethyl-pyrrolidin-2-one.

38. The process according to embodiment 37, wherein said catalyst is chosen from ruthenium hydrogenation catalysts, rhodium hydrogenation catalysts, and iridium hydrogenation catalysts.

39. The process according to any one of embodiments 1-38, wherein said reducing reaction in (d) comprises reacting (S)-3,5,5-trimethyl-pyrrolidin-2-one with a hydride to produce (S)-2,2,4-trimethylpyrrolidine.

40. The process according to any one of embodiments 1-38, wherein said reducing reaction in (d) comprises reacting (S)-3,5,5-trimethyl-pyrrolidin-2-one with a catalyst and hydrogen to produce (S)-2,2,4-trimethylpyrrolidine.

41. The process of embodiment 40, wherein the catalyst is Pt—Sn/TiO$_2$, Pt—Re/TiO$_2$, Pt/TiO$_2$, Rh/TiO$_2$, Rh—Re/TiO$_2$, Pt—Sn/theta-Al$_2$O$_3$, Pt—Sn/SiO$_2$, or Pt—Sn/TiO$_2$.

42. The process according to embodiment 39, wherein said reducing reaction comprises reacting 1-2 molar equivalents of hydride relative to the mole of (S)-3,5,5-trimethyl-pyrrolidin-2-one.

43. The process according to embodiment 39 or 40, wherein said hydride is chosen from lithium aluminum hydride, sodium bis(2-methoxyethoxy)aluminumhydride, and borane.

44. A process for preparing 5,5-dimethyl-3-methylenepyrrolidin-2-one comprising:
(a) reacting 2,2,6,6-tetramethyl-piperidin-4-one or a salt thereof with chloroform and at least one base; and
(b) reacting the products of the reaction in (a) with an acid to produce 5,5-dimethyl-3-methylenepyrrolidin-2-one.

45. The process according to embodiment 42, wherein said at least one base is chosen from potassium t-butoxide, potassium hydroxide, and sodium hydroxide.

46. The process according to embodiment 42, wherein said at least one base is sodium hydroxide.

47. The process according to embodiment 42, wherein from 3 to 15 molar equivalents of said at least one base relative to the mole of 2,2,6,6-tetramethylpiperidin-4-one are added for the reaction in (a).

48. The process according to embodiment 45, wherein from 5 to 12 molar equivalents of said at least one base are added.

49. The process according to embodiment 45, wherein 7.5 molar equivalents of said at least one base are added.

50. The process according to embodiment 45, wherein 10 molar equivalents of said at least one base are added.

51. The process according to embodiment 45, wherein 8 molar equivalents of sodium hydroxide are added.

52. The process according to embodiment 42, wherein said at least one base added for the reaction in (a) is in the form of an aqueous solution having a concentration ranging from 20 wt % to 80 wt % relative to the total weight of said aqueous solution.

53. The process according to embodiment 42, wherein said at least one base is 20 wt % aqueous NaOH.

54. The process according to embodiment 42, wherein said at least one base is 40 wt % aqueous NaOH.

55. The process according to embodiment 42, wherein said at least one base is 50 wt % aqueous NaOH.

56. The process according to any one of embodiments 42-53, wherein said chloroform is present in an amount ranging from 1 to 4 molar equivalents relative to the mole of 2,2,6,6-tetramethylpiperidin-4-one.

57. The process according to embodiment 54, wherein said chloroform is present in an amount ranging from 1.5 to 3.5 molar equivalents relative to the mole of 2,2,6,6-tetramethylpiperidin-4-one.

58. The process according to embodiment 54, wherein said chloroform is present in an amount of 1.75 molar equivalents relative to the mole of 2,2,6,6-tetramethylpiperidin-4-one.

59. The process according to any one of embodiments 42-56 and 189, wherein said at least one phase transfer catalyst is chosen from tetraalkylammonium salts and crown ethers.

60. The process according to embodiment 57, wherein said at least one phase transfer catalyst is chosen from tetraalkylammonium salts.

61. The process according to embodiment 57, wherein said at least one phase transfer catalyst is chosen from tetraalkylammonium halides.

62. The process according to embodiment 57, wherein said at least one phase transfer catalyst in the reaction in (a) is chosen from tributylmethylammonium chloride, tributylmethylammonium bromide, tetrabutylammonium bromide (TBAB), tetrabutylammonium chloride (TBAC), tetrabutylammonium iodide (TBAI), tetrabutylammonium hydroxide (TBAH), benzyltrimethylammonium chloride, tetraoctylammonium bromide (TOAB), tetraoctylammonium chloride (TOAC), tetraoctylammonium iodide (TOAI), trioctylmethylammonium chloride, and trioctylmethylammonium bromide.

63. The process according to any one of embodiments 57-60, wherein from 0.01 molar equivalents to 0.2 molar equivalents of said at least one phase transfer catalyst relative to the mole of 2,2,6,6-tetramethylpiperidin-4-one is added to the reaction in (a).

64. The process according to embodiment 61, wherein from 0.02 molar equivalents to 0.1 molar equivalents of said at least one phase transfer catalyst relative to the mole of 2,2,6,6-tetramethylpiperidin-4-one is added.

65. The process according to embodiment 61, wherein from 0.03 molar equivalents to 0.06 molar equivalents of said at least one phase transfer catalyst relative to the mole of 2,2,6,6-tetramethylpiperidin-4-one is added.

66. The process according to any one of embodiments 42-63, wherein said acid of the reaction in (b) is chosen from aqueous solutions of protic acids.

67. The process according to embodiment 64, wherein said protic acids are chosen from hydrochloric acid, methane sulfonic acid, triflic acid, and sulfuric acid.

68. The process according to embodiment 64, wherein the concentration of said aqueous solutions of protic acids range from 1M to 18M.

69. The process according to embodiment 66, wherein the concentration of said aqueous solutions of protic acids range from 2M to 10M.

70. The process according to embodiment 67, wherein said acid of the reaction in (b) is chosen from HCl having a concentration ranging from 2M to 3M.

71. The process according to embodiment 68, wherein said acid of the reaction in (b) is chosen from 2M HCl.

72. The process according to embodiment 68, wherein said acid of the reaction in (b) is chosen from 2.5M HCl.

73. The process according to embodiment 68, wherein said acid of the reaction in (b) is chosen from 3M HCl.

74. The process according to any one of embodiments 42-71, wherein 0.5 to 10 molar equivalents of said acid relative to the mole of 2,2,6,6-tetramethylpiperidin-4-one are added to the reaction in (b).

75. The process according to embodiment 72, wherein 1 to 4 molar equivalents of said acid relative to the mole of 2,2,6,6-tetramethylpiperidin-4-one are added to the reaction in (b).

76. The process according to embodiment 72, wherein 1.5 molar equivalents of said acid relative to the mole of 2,2,6,6-tetramethylpiperidin-4-one are added to the reaction in (b).

77. The process according to embodiment 42, wherein a yield of 5,5-dimethyl-3-methylenepyrrolidin-2-one produced from the reactions in (a) and (b) ranges from 40% to 70% relative to the mole of 2,2,6,6-tetramethylpiperidin-4-one.

78. A process for preparing (R)-2,2,4-trimethylpyrrolidine or a salt thereof comprising:
(a) reacting 2,2,6,6-tetramethyl-piperidin-4-one or a salt thereof with chloroform and at least one base;
(b) reacting the products of the reaction in (a) with an acid to produce 5,5-dimethyl-3-methylenepyrrolidin-2-one;
(c) hydrogenating 5,5-dimethyl-3-methylenepyrrolidin-2-one to produce (R)-3,5,5-trimethyl-pyrrolidin-2-one;
(d) reducing (R)-3,5,5-trimethyl-pyrrolidin-2-one to produce (R)-2,2,4-trimethylpyrrolidine; and
(e) optionally treating (R)-2,2,4-trimethylpyrrolidine with acid to produce a salt of (R)-2,2,4-trimethylpyrrolidine.

79. The process according to embodiment 76, further comprising treating (R)-2,2,4-trimethylpyrrolidine with HCl to generate (R)-2,2,4-trimethylpyrrolidine hydrochloride.

80. The process according to embodiment 76 or 77, wherein said at least one base is chosen from potassium t-butoxide, potassium hydroxide, and sodium hydroxide.

81. The process according to embodiment 76 or 77, wherein said at least one base is sodium hydroxide.

82. The process according to embodiment 76 or 77, wherein from 3 to 15 molar equivalents of said at least one base relative to the mole of 2,2,6,6-tetramethylpiperidin-4-one are added for the reaction in (a).

83. The process according to embodiment 80, wherein from 5 to 12 molar equivalents of said at least one base are added.

84. The process according to embodiment 80, wherein 7.5 molar equivalents of said at least one base are added.

85. The process according to embodiment 80, wherein 10 molar equivalents of said at least one base are added.

86. The process according to embodiment 80, wherein 8 molar equivalents of sodium hydroxide are added.

87. The process according to embodiment 76 or 77, wherein said at least one base added for the reaction in (a) is in the form of an aqueous solution having a concentration ranging from 20 wt % to 80 wt % relative to the total weight of said aqueous solution.

88. The process according to embodiment 76 or 77, wherein said at least one base is 20 wt % aqueous NaOH.

89. The process according to embodiment 76 or 77, wherein said at least one base is 40 wt % aqueous NaOH.

90. The process according to embodiment 76 or 77, wherein said at least one base is 50 wt % aqueous NaOH.

91. The process according to any one of embodiments 76-88, wherein said chloroform is present in an amount ranging from 1 to 4 molar equivalents relative to the mole of 2,2,6,6-tetramethylpiperidin-4-one.

92. The process according to embodiment 89, wherein said chloroform is present in an amount ranging from 1.5 to 3.5 molar equivalents relative to the mole of 2,2,6,6-tetramethylpiperidin-4-one.

93. The process according to embodiment 89, wherein said chloroform is present in an amount of 1.75 molar equivalents relative to the mole of 2,2,6,6-tetramethylpiperidin-4-one.

94. The process according to any one of embodiments 76-91, wherein said 2,2,6,6-tetramethyl-piperidin-4-one or a salt thereof is reacted with chloroform, at least one base, and at least one phase transfer catalyst.

95. The process according to any one of embodiments 76-92, wherein said at least one phase transfer catalyst is chosen from tetraalkylammonium salts and crown ethers.

96. The process according to embodiment 93 wherein said at least one phase transfer catalyst is chosen from tetraalkylammonium salts.

97. The process according to embodiment 94, wherein said at least one phase transfer catalyst is chosen from tetraalkylammonium halides.

98. The process according to embodiment 95, wherein said at least one phase transfer catalyst is chosen from tributylmethylammonium chloride, tributylmethylammonium bromide, tetrabutylammonium bromide (TBAB), tetrabutylammonium chloride (TBAC), tetrabutylammonium iodide (TBAI), tetrabutylammonium hydroxide (TBAH), benzyltrimethylammonium chloride, tetraoctylammonium bromide (TOAB), tetraoctylammonium chloride (TOAC), tetraoctylammonium iodide (TOAI), trioctylmethylammonium chloride, and trioctylmethylammonium bromide.

99. The process according to any one of embodiments 76-96, wherein from 0.01 molar equivalents to 0.2 molar equivalents of said at least one phase transfer catalyst relative to the mole of 2,2,6,6-tetramethylpiperidin-4-one is added to the reaction in (a).

100. The process according to embodiment 97, wherein from 0.02 molar equivalents to 0.1 molar equivalents of said at least one phase transfer catalyst relative to the mole of 2,2,6,6-tetramethylpiperidin-4-one is added.

101. The process according to embodiment 98, wherein from 0.03 molar equivalents to 0.06 molar equivalents of said at least one phase transfer catalyst relative to the mole of 2,2,6,6-tetramethylpiperidin-4-one is added.

102. The process according to any one of embodiments 76-99, wherein said acid of the reaction in (b) is chosen from aqueous solutions of protic acids.

103. The process according to embodiment 100, wherein said protic acids are chosen from hydrochloric acid, methane sulfonic acid, triflic acid, and sulfuric acid.

104. The process according to embodiment 100, wherein the concentration of said aqueous solutions of protic acids range from 1M to 18M.

105. The process according to embodiment 102, wherein the concentration of said aqueous solutions of protic acids range from 2M to 10M.

106. The process according to embodiment 103, wherein said acid of the reaction in (b) is chosen from HCl having a concentration ranging from 2M to 3M.

107. The process according to embodiment 103, wherein said acid of the reaction in (b) is chosen from 2M HCl.

108. The process according to embodiment 103, wherein said acid of the reaction in (b) is chosen from 2.5M HCl.

109. The process according to embodiment 103, wherein said acid of the reaction in (b) is chosen from 3M HCl.

110. The process according to any one of embodiments 76-107, wherein 0.5 to 10 molar equivalents of said acid relative to the mole of 2,2,6,6-tetramethylpiperidin-4-one are added to the reaction in (b).

111. The process according to embodiment 108, wherein 1 to 4 molar equivalents of said acid relative to the mole of 2,2,6,6-tetramethylpiperidin-4-one are added to the reaction in (b).

112. The process according to embodiment 109, wherein 1.5 molar equivalents of said acid relative to the mole of 2,2,6,6-tetramethylpiperidin-4-one are added to the reaction in (b).

113. The process according to embodiment 76 or 77, wherein a yield of 5,5-dimethyl-3-methylenepyrrolidin-2-one produced from the reactions in (a) and (b) ranges from 40% to 70% relative to the mole of 2,2,6,6-tetramethylpiperidin-4-one.

114. The process according to any one of embodiments 76-111, wherein said hydrogenating reaction in (c) comprises reacting 5,5-dimethyl-3-methylenepyrrolidin-2-one with at least one catalyst and hydrogen gas to produce (R)-3,5,5-trimethyl-pyrrolidin-2-one.

115. The process according to embodiment 112, wherein said catalyst is chosen from ruthenium hydrogenation catalysts, rhodium hydrogenation catalysts, and iridium hydrogenation catalysts.

116. The process according to any one of embodiments 76-113, wherein said reducing reaction in (d) comprises reacting (R)-3,5,5-trimethyl-pyrrolidin-2-one with a hydride to produce (R)-2,2,4-trimethylpyrrolidine.

117. The process according to embodiment 114, wherein said reducing reaction comprises reacting 1-2 molar equivalents of hydride relative to the mole of (R)-3,5,5-trimethyl-pyrrolidin-2-one.

118. The process according to embodiment 114 or 115, wherein said hydride is chosen from lithium aluminum hydride, sodium bis(2-methoxyethoxy)aluminumhydride, and borane.

119. A process for preparing (S)-3,5,5-trimethylpyrrolidin-2-one comprising:
(a) reacting 2,2,6,6-tetramethyl-piperidin-4-one or a salt thereof with chloroform and at least one base;
(b) reacting the products of the reaction in (a) with an acid to produce 5,5-dimethyl-3-methylenepyrrolidin-2-one; and
(c) hydrogenating 5,5-dimethyl-3-methylenepyrrolidin-2-one to produce (S)-3,5,5-trimethyl-pyrrolidin-2-one.

120. The process according to embodiment 117, wherein said at least one base is chosen from potassium t-butoxide, potassium hydroxide, and sodium hydroxide.

121. The process according to embodiment 117, wherein said at least one base is sodium hydroxide.

122. The process according to embodiment 117, wherein from 3 to 15 molar equivalents of said at least one base relative to the mole of 2,2,6,6-tetramethylpiperidin-4-one are added for the reaction in (a).

123. The process according to embodiment 120, wherein from 5 to 12 molar equivalents of said at least one base are added.

124. The process according to embodiment 120, wherein 7.5 molar equivalents of said at least one base are added.

125. The process according to embodiment 120, wherein 10 molar equivalents of said at least one base are added.

126. The process according to embodiment 120, wherein 8 molar equivalents of sodium hydroxide are added.

127. The process according to embodiment 120, wherein said at least one base added for the reaction in (a) is in the form of an aqueous solution having a concentration ranging from 20 wt % to 80 wt % relative to the total weight of said aqueous solution.

128. The process according to embodiment 117, wherein said at least one base is 20 wt % aqueous NaOH.

129. The process according to embodiment 117, wherein said at least one base is 40 wt % aqueous NaOH.

130. The process according to embodiment 117, wherein said at least one base is 50 wt % aqueous NaOH.

131. The process according to any one of embodiments 117-128, wherein said chloroform is present in an amount ranging from 1 to 4 molar equivalents relative to the mole of 2,2,6,6-tetramethylpiperidin-4-one.

132. The process according to embodiment 129, wherein said chloroform is present in an amount ranging from 1.5 to 3.5 molar equivalents relative to the mole of 2,2,6,6-tetramethylpiperidin-4-one.

133. The process according to embodiment 129, wherein said chloroform is present in an amount of 1.75 molar equivalents relative to the mole of 2,2,6,6-tetramethylpiperidin-4-one.

134. The process according to any one of embodiments 117-131 and 190, wherein said at least one phase transfer catalyst is chosen from tetraalkylammonium salts and crown ethers.

135. The process according to embodiment 132, wherein said at least one phase transfer catalyst is chosen from tetraalkylammonium salts.

136. The process according to embodiment 132, wherein said at least one phase transfer catalyst is chosen from tetraalkylammonium halides.

137. The process according to embodiment 132, wherein said at least one phase transfer catalyst in the reaction in (a) is chosen from tributylmethylammonium chloride, tributylmethylammonium bromide, tetrabutylammonium bromide (TBAB), tetrabutylammonium chloride (TBAC), tetrabutylammonium iodide (TBAI), tetrabutylammonium hydroxide (TBAH), benzyltrimethylammonium chloride, tetraoctylammonium bromide (TOAB), tetraoctylammonium chloride (TOAC), tetraoctylammonium iodide (TOAI), trioctylmethylammonium chloride, and trioctylmethylammonium bromide.

138. The process according to any one of embodiments 117-135, wherein from 0.01 molar equivalents to 0.2 molar equivalents of said at least one phase transfer catalyst relative to the mole of 2,2,6,6-tetramethylpiperidin-4-one is added to the reaction in (a).

139. The process according to embodiment 136, wherein from 0.02 molar equivalents to 0.1 molar equivalents of said at least one phase transfer catalyst relative to the mole of 2,2,6,6-tetramethylpiperidin-4-one is added.

140. The process according to embodiment 137, wherein from 0.03 molar equivalents to 0.06 molar equivalents of said at least one phase transfer catalyst relative to the mole of 2,2,6,6-tetramethylpiperidin-4-one is added.

141. The process according to any one of embodiments 117-138, wherein said acid of the reaction in (b) is chosen from aqueous solutions of protic acids.

142. The process according to embodiment 139, wherein said protic acids are chosen from hydrochloric acid, methane sulfonic acid, triflic acid, and sulfuric acid.

143. The process according to embodiment 139, wherein the concentration of said aqueous solutions of protic acids range from 1M to 18M.

144. The process according to embodiment 141 wherein the concentration of said aqueous solutions of protic acids range from 2M to 10M.

145. The process according to embodiment 142, wherein said acid of the reaction in (b) is chosen from HCl having a concentration ranging from 2M to 3M.

146. The process according to embodiment 143, wherein said acid of the reaction in (b) is chosen from 2M HCl.

147. The process according to embodiment 143, wherein said acid of the reaction in (b) is chosen from 2.5M HCl.

148. The process according to embodiment 143, wherein said acid of the reaction in (b) is chosen from 3M HCl.

149. The process according to any one of embodiments 117-146, wherein 0.5 to 10 molar equivalents of said acid relative to the mole of 2,2,6,6-tetramethylpiperidin-4-one are added to the reaction in (b).

150. The process according to embodiment 147, wherein 1 to 4 molar equivalents of said acid relative to the mole of 2,2,6,6-tetramethylpiperidin-4-one are added to the reaction in (b).

151. The process according to embodiment 148, wherein 1.5 molar equivalents of said acid relative to the mole of 2,2,6,6-tetramethylpiperidin-4-one are added to the reaction in (b).

152. The process according to embodiment 117, wherein a yield of 5,5-dimethyl-3-methylenepyrrolidin-2-one produced from the reactions in (a) and (b) ranges from 40% to 70% relative to the mole of 2,2,6,6-tetramethylpiperidin-4-one.

153. The process according to any one of embodiments 117-150, wherein said hydrogenating reaction in (c) comprises reacting 5,5-dimethyl-3-methylenepyrrolidin-2-one with at least one catalyst and hydrogen gas to produce (S)-3,5,5-trimethyl-pyrrolidin-2-one.

154. The process according to embodiment 151, wherein said catalyst is chosen from ruthenium hydrogenation catalysts, rhodium hydrogenation catalysts, and iridium hydrogenation catalysts.

155. A process for preparing (R)-3,5,5-trimethylpyrrolidin-2-one comprising:
(a) reacting 2,2,6,6-tetramethyl-piperidin-4-one or a salt thereof with chloroform and at least one base;
(b) reacting the products of the reaction in (a) with an acid to produce 5,5-dimethyl-3-methylenepyrrolidin-2-one; and
(c) hydrogenating 5,5-dimethyl-3-methylenepyrrolidin-2-one to produce (R)-3,5,5-trimethyl-pyrrolidin-2-one.

156. The process according to embodiment 153, wherein said at least one base is chosen from potassium t-butoxide, potassium hydroxide, and sodium hydroxide.

157. The process according to embodiment 153, wherein said at least one base is sodium hydroxide.

158. The process according to any one of embodiments 153-155, wherein from 3 to 15 molar equivalents of said at least one base relative to the mole of 2,2,6,6-tetramethylpiperidin-4-one are added for the reaction in (a).

159. The process according to embodiment 156, wherein from 5 to 12 molar equivalents of said at least one base are added.

160. The process according to embodiment 156, wherein 7.5 molar equivalents of said at least one base are added.

161. The process according to embodiment 156, wherein 10 molar equivalents of said at least one base are added.

162. The process according to embodiment 153, wherein 8 molar equivalents of sodium hydroxide are added.

163. The process according to embodiment 156, wherein said at least one base added for the reaction in (a) is in the form of an aqueous solution having a concentration ranging from 20 wt % to 80 wt % relative to the total weight of said aqueous solution.

164. The process according to embodiment 153, wherein said at least one base is 20 wt % aqueous NaOH.

165. The process according to embodiment 153, wherein said at least one base is 40 wt % aqueous NaOH.

166. The process according to embodiment 153, wherein said at least one base is 50 wt % aqueous NaOH.

167. The process according to any one of embodiments 153-164, wherein said chloroform is present in an amount ranging from 1 to 4 molar equivalents relative to the mole of 2,2,6,6-tetramethylpiperidin-4-one.

168. The process according to embodiment 165, wherein said chloroform is present in an amount ranging from 1.5 to 3.5 molar equivalents relative to the mole of 2,2,6,6-tetramethylpiperidin-4-one.

169. The process according to embodiment 165, wherein said chloroform is present in an amount of 1.75 molar equivalents relative to the mole of 2,2,6,6-tetramethylpiperidin-4-one.

170. The process according to any one of embodiments 153-167 and 191, wherein said at least one phase transfer catalyst is chosen from tetraalkylammonium salts and crown ethers.

171. The process according to embodiment 168, wherein said at least one phase transfer catalyst is chosen from tetraalkylammonium salts.

172. The process according to embodiment 168, wherein said at least one phase transfer catalyst is chosen from tetraalkylammonium halides.

173. The process according to embodiment 168, wherein said at least one phase transfer catalyst in the reaction in (a) is chosen from tributylmethylammonium chloride, tributylmethylammonium bromide, tetrabutylammonium bromide (TBAB), tetrabutylammonium chloride (TBAC), tetrabutylammonium iodide (TBAI), tetrabutylammonium hydroxide (TBAH), benzyltrimethylammonium chloride, tetraoctylammonium bromide (TOAB), tetraoctylammonium chloride (TOAC), tetraoctylammonium iodide (TOAI), trioctylmethylammonium chloride, and trioctylmethylammonium bromide.

174. The process according to any one of embodiments 153-171, wherein from 0.01 molar equivalents to 0.2 molar equivalents of said at least one phase transfer catalyst relative to the mole of 2,2,6,6-tetramethylpiperidin-4-one is added to the reaction in (a).

175. The process according to embodiment 172, wherein from 0.02 molar equivalents to 0.1 molar equivalents of said at least one phase transfer catalyst relative to the mole of 2,2,6,6-tetramethylpiperidin-4-one is added.

176. The process according to embodiment 172, wherein from 0.03 molar equivalents to 0.06 molar equivalents of said at least one phase transfer catalyst relative to the mole of 2,2,6,6-tetramethylpiperidin-4-one is added.

177. The process according to any one of embodiments 153-174, wherein said acid of the reaction in (b) is chosen from aqueous solutions of protic acids.

178. The process according to embodiment 175, wherein said protic acids are chosen from hydrochloric acid, methane sulfonic acid, triflic acid, and sulfuric acid.

179. The process according to embodiment 175, wherein the concentration of said aqueous solutions of protic acids ranges from 1M to 18M.

180. The process according to embodiment 175, wherein the concentration of said aqueous solutions of protic acids ranges from 2M to 10M.

181. The process according to embodiment 178, wherein said acid of the reaction in (b) is chosen from HCl having a concentration ranging from 2M to 3M.

182. The process according to embodiment 179, wherein said acid of the reaction in (b) is chosen from 2M HCl.

183. The process according to embodiment 179, wherein said acid of the reaction in (b) is chosen from 2.5M HCl.

184. The process according to embodiment 179, wherein said acid of the reaction in (b) is chosen from 3M HCl.

185. The process according to any one of embodiments 153-182, wherein 0.5 to 10 molar equivalents of said acid relative to the mole of 2,2,6,6-tetramethylpiperidin-4-one are added to the reaction in (b).

186. The process according to embodiment 183, wherein 1 to 4 molar equivalents of said acid relative to the mole of 2,2,6,6-tetramethylpiperidin-4-one are added to the reaction in (b).

187. The process according to embodiment 183, wherein 1.5 molar equivalents of said acid relative to the mole of 2,2,6,6-tetramethylpiperidin-4-one are added to the reaction in (b).

188. The process according to embodiment 153, wherein a yield of 5,5-dimethyl-3-methylenepyrrolidin-2-one produced from the reactions in (a) and (b) ranges from 40% to 70% relative to the mole of 2,2,6,6-tetramethylpiperidin-4-one.

189. The process according to any one of embodiments 153-186, wherein said hydrogenating reaction in (c) comprises reacting 5,5-dimethyl-3-methylenepyrrolidin-2-one with at least one catalyst and hydrogen gas to produce (S)-3,5,5-trimethyl-pyrrolidin-2-one.

190. The process according to embodiment 187, wherein said catalyst is chosen from ruthenium hydrogenation catalysts, rhodium hydrogenation catalysts, and iridium hydrogenation catalysts.

191. The process according to any one of embodiments 42-56, wherein said 2,2,6,6-tetramethyl-piperidin-4-one or a salt thereof is reacted with chloroform, at least one base, and at least one phase transfer catalyst.

192. The process according to any one of embodiments 117-131, wherein said 2,2,6,6-tetramethyl-piperidin-4-one or a salt thereof is reacted with chloroform, at least one base, and at least one phase transfer catalyst.

193. The process according to any one of embodiments 153-167, wherein said 2,2,6,6-tetramethyl-piperidin-4-one or a salt thereof is reacted with chloroform, at least one base, and at least one phase transfer catalyst.

194. The process according to any one of embodiments 1-24, wherein 2,2,6,6-tetramethyl-piperidin-4-one or a salt thereof is reacted with chloroform, at least one base, and at least one solvent.

195. The process according to embodiment 192, wherein the at least one solvent is chosen from organic solvents.

196. The process according to embodiment 193, wherein the at least one solvent is chosen from dichloromethane, heptane, chloroform, trifluorotoluene, tetrahydrofuran (THF), and N-methylpyrrolidone (NMP).

197. The process according to any one of embodiments 42-63 and 189, wherein 2,2,6,6-tetramethyl-piperidin-4-one or a salt thereof is reacted with chloroform, at least one base, and at least one solvent.

198. The process according to embodiment 195, wherein the at least one solvent is chosen from organic solvents.

199. The process according to embodiment 196, wherein the at least one solvent is chosen from dichloromethane, heptane, chloroform, trifluorotoluene, tetrahydrofuran (THF), and N-methylpyrrolidone (NMP).

200. The process according to any one of embodiments 76-99, wherein 2,2,6,6-tetramethyl-piperidin-4-one or a salt thereof is reacted with chloroform, at least one base, and at least one solvent.

201. The process according to embodiment 198, wherein the at least one solvent is chosen from organic solvents.

202. The process according to embodiment 199, wherein the at least one solvent is chosen from dichloromethane, heptane, chloroform, trifluorotoluene, tetrahydrofuran (THF), and N-methylpyrrolidone (NMP).

203. The process according to any one of embodiments 117-38 and 190, wherein 2,2,6,6-tetramethyl-piperidin-4-one or a salt thereof is reacted with chloroform, at least one base, and at least one solvent.

204. The process according to embodiment 201, wherein the at least one solvent is chosen from organic solvents.

205. The process according to embodiment 202, wherein the at least one solvent is chosen from dichloromethane, heptane, chloroform, trifluorotoluene, tetrahydrofuran (THF), and N-methylpyrrolidone (NMP).

206. The process according to any one of embodiments 153-174 and 191, wherein 2,2,6,6-tetramethyl-piperidin-4-one or a salt thereof is reacted with chloroform, at least one base, and at least one solvent.

207. The process according to embodiment 204, wherein the at least one solvent is chosen from organic solvents.

208. The process according to embodiment 205, wherein the at least one solvent is chosen from dichloromethane, heptane, chloroform, trifluorotoluene, tetrahydrofuran (THF), and N-methylpyrrolidone (NMP).

EXAMPLES

Example 1. Reaction (a) and (b): Synthesis of 5,5-dimethyl-3-methylenepyrrolidin-2-one

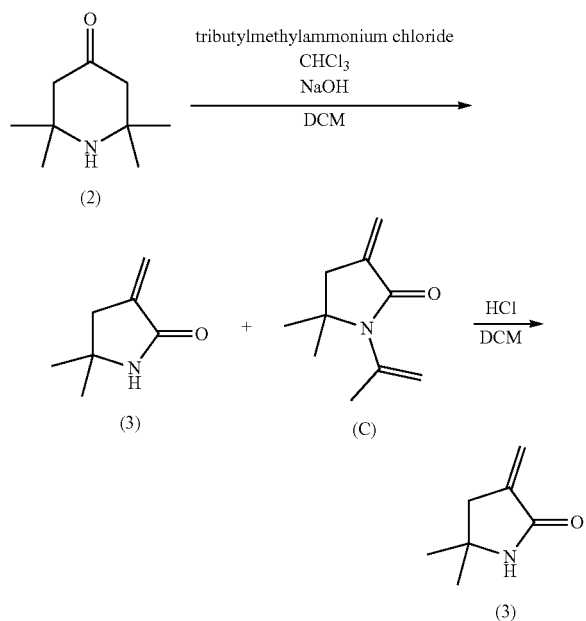

Example 1A 2,2,6,6-tetramethylpiperidin-4-one (50.00 g, 305.983 mmol, 1.000 equiv), tributylmethylammonium chloride (2.89 g, 3.0 mL, 9.179 mmol, 0.030 equiv), chloroform (63.92 g, 43.2 mL, 535.470 mmol, 1.750 equiv), and DCM (dichloromethane) (100.0 mL, 2.00 vol) were charged to a 1000 mL three-neck round bottom flask equipped with an overhead stirrer. The reaction mixture was stirred at 300 rpm, and 50 wt % NaOH (195.81 g, 133.2 mL, 2,447.863 mmol, 8.000 equiv) was added dropwise (via addition funnel) over 1.5 h while maintaining the temperature below 25° C. with intermittent ice/acetone bath. The reaction mixture was stirred at 500 rpm for 18 h, and monitored by GC (3% unreacted piperidinone after 18 h). The suspension was diluted with DCM (100.0 mL, 2.00 vol) and H$_2$O (300.0 mL, 6.00 vol), and the phases were separated. The aqueous phase was extracted with DCM (100.0 mL, 2.00 vol). The organic phases were combined and 3 M hydrochloric acid (16.73 g, 153.0 mL, 458.974 mmol, 1.500 equiv) was added. The mixture was stirred at 500 rpm for 2 h. The conversion was complete after approximately 1 h. The aqueous phase was saturated with NaCl, H$_2$O (100.0 mL, 2.00 vol) was added to help reduce the emulsion, and the phases were separated. The aqueous phase was extracted with DCM (100.0 mL, 2.00 vol) twice. H$_2$O (100.0 mL, 2.00 vol) was added to help with emulsion separation. The organic phases were combined, dried (MgSO$_4$), and concentrated to afford 32.6 g (85%) of crude Compound (3) as a pale orange clumpy solid. The crude was recrystallized from hot (90° C.) iPrOAc (isopropyl acetate) (71.7 mL, 2.2 vol. of crude), cooled to 80° C., and ~50 mg of crystalline Compound (3) was added for seeding. Crystallization started at 77° C., the mixture was slowly cooled to ambient temperature, and aged for 2 h. The solid was collected by filtration, washed with 50/50 iPrOAc/heptane (20.0 mL, 0.40 vol) twice, and dried overnight in the vacuum oven at 40° C. to afford the desired product (23.70 g, 189.345 mmol, 62% yield) as a white sand colored crystalline solid. $^1$H NMR (400 MHz, CDCl$_3$, 7.26 ppm) δ 7.33 (bs, 1H), 5.96-5.95 (m, 1H), 5.31-5.30 (m, 1H), 2.6 (t, J=2.5 Hz, 2H), 1.29 (s, 6H).

Synthesis 1B i. Under a nitrogen atmosphere, 2,2,6,6-tetramethylpiperidin-4-one (257.4 kg, 1658.0 mol, 1.00 eq.), tri-butyl methyl ammonium chloride (14.86 kg, 63.0 mol, 0.038 eq.), chloroform (346.5 kg, 2901.5 mol, 1.75 eq.) and DCM (683.3 kg) were added to a 500 L enamel reactor. The reaction was stirred at 85 rpm and cooled to 15-17° C. The solution of 50 wt % sodium hydroxide (1061.4 kg, 13264.0 mol, 8.00 eq.) was added dropwise over 40 h while maintaining the temperature between 15-25° C. The reaction mixture was stirred and monitored by GC.

ii. The suspension was diluted with DCM (683.3 kg) and water (1544.4 kg). The organic phase was separated. The aqueous phase was extracted with DCM (683.3 kg). The organic phases were combined, cooled to 10° C. and then 3 M hydrochloric acid (867.8 kg, 2559.0 mol, 1.5 eq.) was added. The mixture was stirred at 10-15° C. for 2 h. The organic phase was separated. The aqueous phase was extracted with DCM (683.3 kg×2). The organic phases were combined, dried over Na$_2$SO$_4$ (145.0 kg) for 6 h. The solid was filtered off and washed with DCM (120.0 kg). The filtrate was stirred with active charcoal (55 kg) for 6 h. The resulting mixture was filtered and the filtrate was concentrated under reduced pressure (30~40° C., -0.1 MPa). Then isopropyl acetate (338 kg) was added and the mixture was heated to 87~91° C., stirred for 1 h. Then the solution was cooled to 15° C. in 18 h and stirred for 1 h at 15° C. The solid was collected by filtration, washed with 50% isopropyl acetate/hexane (80.0 kg×2) and dried overnight in the vacuum oven at 50° C. to afford 5,5-dimethyl-3-methylenepyrrolidin-2-one as an off white solid, 55% yield.

Example 2. Reaction (c): Synthesis of (S)-3,5,5-trimethyl-pyrrolidin-2-one from 5,5-dimethyl-3-methylenepyrrolidin-2-one

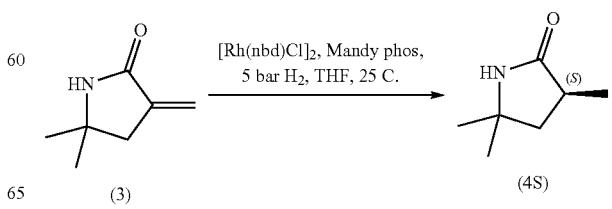

Example 2A: Use of Rh Catalyst

Step 1: Preparation of Rh Catalyst Formation: In a 3 L Schlenk flask, 1.0 L of tetrahydrofuran (THF) was degassed with an argon stream. Mandyphos Ligand SL-M004-1 (1.89 g) and [Rh(nbd)Cl]$_2$ (98%, 0.35 g) (chloronorbornadiene rhodium(I) dimer) were added. The resulting orange catalyst solution was stirred for 30 min at room temperature to form a catalyst solution.

Step 2:

A 50 L stainless steel autoclave was charged with 5,5-dimethyl-3-methylenepyrrolidin-2-one (6.0 kg, Compound (3)) and THF (29 L). The autoclave was sealed and the resulting suspension was flushed with nitrogen (3 cycles at 10 bar), and then released of pressure. Next the catalyst solution from Step 1 was added. The autoclave was flushed with nitrogen without stirring (3 cycles at 5 bar) and hydrogen (3 cycles at 5 bar). The pressure was set to 5 bar and a 50 L reservoir was connected. After 1.5 h with stirring at 1000 rpm and no hydrogen uptake the reactor was flushed again with nitrogen (3 cycles at 10 bar) with stirring and additional catalyst solution was added. The autoclave was again flushed to hydrogen with the above described procedure (3×5 bar N2, 3×5 bar H2) and adjusted to 5 bar. After 2 h, the pressure was released, the autoclave was flushed with nitrogen (3 cycles at 5 bar) and the product solution was discharged into a 60 L inline barrel. The autoclave was charged again with THF (5 L) and stirred with 1200 rpm for 5 min. The wash solution was added to the reaction mixture.

Step 3: The combined solutions were transferred into a 60 L reactor. The inline barrel was washed with 1 L THF which was also added into the reactor. 20 L THF were removed by evaporation at 170 mbar and 40° C. 15 L heptane were added. The distillation was continued and the removed solvent was continuously replaced by heptane until the THF content in the residue was 1% w/w (determined by NMR). The reaction mixture was heated to 89° C. (turbid solution) and slowly cooled down again (ramp: 14° C./h). Several heating and cooling cycles around 55 to 65° C. were made. The off-white suspension was transferred to a stirred pressure filter and filtered (ECTFEFpad, d=414 mm, 60 my, Filtration time=5 min). 10 L of the mother liquor was transferred back into the reactor to wash the crystals from the reactor walls and the obtained slurry was also added to the filter. The collected solid was washed with 2×2.5 1 heptane, discharged and let dry on the rotovap at 40° C. and 4 mbar to obtain the product, (S)-3,5,5-trimethyl-pyrrolidin-2-one; 5.48 Kg (91%), 98.0% ee.

Synthesis 2B: Use of Ru Catalyst.

The reaction was performed in a similar manner as described above in Example 2A except the use of a Ru catalyst instead of a Rh catalyst.

Compound (3) (300 g) was dissolved in THF (2640 g, 10 Vol) in a vessel. In a separate vessel, a solution of [RuCl(p-cymene){(R)-segphos}]Cl (0.439 g, 0.0002 eq) in THF (660 g, 2.5 Vol) was prepared. The solutions were premixed in situ and passed through a Plug-flow reactor (PFR). The flow rate for the Compound (3) solution was at 1.555 mL/min and the Ru catalyst solution was at 0.287 mL/min. Residence time in the PFR was 4 hours at 30° C., with hydrogen pressure of 4.5 MPa. After completion of reaction, the THF solvent was distilled off to give a crude residue. Heptane (1026 g, 5 vol) was added and the resulting mixture was heated to 90° C. The mixture was seeded with 0.001 eq. of Compound 4S seeds. The mixture was cooled to −15° C. at 20° C./h. After cooling, heptane (410 g, 2 vol) was added and the solid product was recovered by filtration. The resulting product was dried in a vacuum oven at 35° C. to give (S)-3,5,5-trimethyl-pyrrolidin-2-one (281.77 g, 98.2% ee, 92% yield).

Example 2C: Analytical Measurements

Analytical chiral HPLC method for the determination of the conversion, chemoselectivity and enantiomeric excess of the products form Example 2A and 2B was made under the following conditions: Instrument: Agilent Chemstation 1100; Column: Phenomenex Lux 5u Cellulose—2, 4.6 mm×250 mm×5 um, LHS6247; Solvent: Heptane/iPrOH (90:10); Flow: 1.0 ml/min; Detection: UV (210 nm); Temperature: 25° C.; Sample concentration: 30 of reaction solution evaporated, dissolved in 1 mL; heptane/iPrOH (80/20); Injection volume: 10.0 μL, Run time 20 min; Retention times: 5,5-dimethyl-3-methylenepyrrolidin-2-one: 13.8 min, (S)-3,5,5-trimethyl-pyrrolidin-2-one: 10.6 min, and (R)-3,5,5-trimethyl-pyrrolidin-2-one: 12.4 min.

Example 3: Alternate Synthesis of (S)-3,5,5-trimethyl-pyrrolidin-2-one from 5,5-dimethyl-3-methylenepyrrolidin-2-one

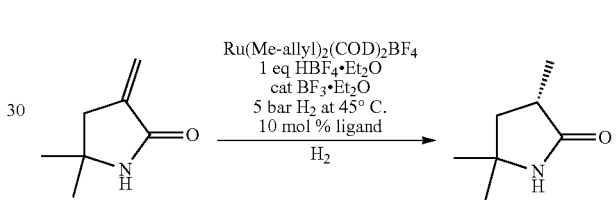

Mandyphos (0.00479 mmol, 0.12 eq) was weighed into a GC vial. In a separate vial, Ru(Me-allyl)$_2$(COD) (16.87 mg, 0.0528 mmol) was weighed and dissolved in DCM (1328 μL). In another vial HBF$_4$.Et$_2$O (6.6 μL) and BF$_3$.Et$_2$O (2.0 μL) were dissolved in DCM (240 μL). To the GC vial containing the ligand was added, under a flow of argon, the Ru(Me-allyl)$_2$(COD) solution (100 μL; 0.00399 mmol, 0.1 eq) and the HBF$_4$.Et$_2$O/BF$_3$.Et$_2$O solution (20 μL; 1 eq HBF$_4$.Et$_2$O and catalytic BF$_3$.Et$_2$O). The resulting mixtures were stirred under a flow of argon for 30 minutes. 5,5-dimethyl-3-methylenepyrrolidin-2-one (5 mg, 0.0399 mmol) in EtOH (1 mL) was added. The vials were placed in the hydrogenation apparatus. The apparatus was flushed with H$_2$ (3×) and charged with 5 bar H$_2$. After standing for 45 minutes, the apparatus was placed in an oil bath at temperature of 45° C. The reaction mixtures were stirred overnight under H$_2$. 200 μL of the reaction mixture was diluted with MeOH (800 μL) and analyzed for conversion and ee. $^1$H NMR (400 MHz, Chloroform-d) δ 6.39 (s, 1H), 2.62 (ddq, J=9.9, 8.6, 7.1 Hz, 1H), 2.17 (ddd, J=12.4, 8.6, 0.8 Hz, 1H), 1.56 (dd, J=12.5, 9.9 Hz, 1H), 1.31 (s, 3H), 1.25 (s, 3H), 1.20 (d, J=7.1 Hz, 3H).

IPC Analytical Method for Asymmetric Hydrogenation

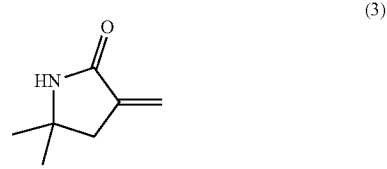

(3)

-continued

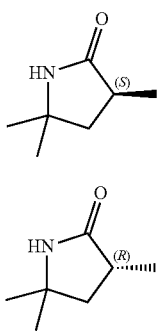

(4S)

(4R)

| Column | Lux Cellulose-2, 4.6 × 250 mm |
|---|---|
| Isocratic | 90% Heptane/10% IPA |
| Flow rate | 1.0 mL/min |
| Column Temperature | 30° C. |
| UV detector wavelength | 210 nm, bw = 4; Ref = off |
| Injection volume | 10 μL |
| Run time | 15 minutes |
| Nominal concentration | 0.4 mg/mL |
| Diluent | Heptane/IPA (8/2) |
| Retention times | Compound (4S) = 10.6 min |
| | Compound (4R) = 11.8 min |
| | Compound (3) = 12.6 min |
| Compound (4S)/Compound (4R) Resolution | 2.8 |
| Compound (4R)/Compound (3) Resolution | 2.0 |

Example 4. Synthesis of (S)-2,2,4-trimethylpyrrolidine Hydrochloride from (S)-3,5,5-trimethyl-pyrrolidin-2-one

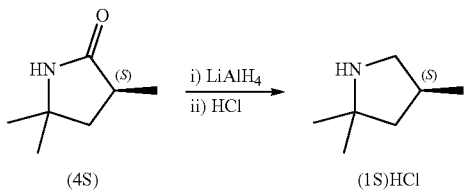

Example 4A

Anhydrous THF (100 ml) was charged to a dry 750 ml reactor and the jacket temperature was set to 50° C. Once the vessel contents were at 50° C., LiAlH₄ pellets (10 g, 263 mmol, 1.34 eq.) were added. The mixture was stirred for 10 minutes, then a solution of (4S) (25 g, 197 mmol) in anhydrous THF (100 ml) was added dropwise over 45 minutes, maintaining the temperature between 50-60° C. Once the addition was complete the jacket temperature was increased to 68° C. and the reaction was stirred for 18.5 hrs. The reaction mixture was cooled to 30° C. then saturated sodium sulfate solution (20.9 ml) was added dropwise over 30 minutes, keeping the temperature below 40° C. Vigorous evolution of hydrogen was observed and the reaction mixture thickened but remained mixable. The mixture thinned towards the end of the addition. The mixture was cooled to 20° C., diluted with iPrOAc (100 ml) and stirred for an additional 10 minutes. The suspension was then drained and collected through the lower outlet valve, washing through with additional iPrOAc (50 ml). The collected suspension was filtered through a Celite pad on a sintered glass funnel under suction and washed with iPrOAc (2×50 ml).

The filtrate was transferred back to the cleaned reactor and cooled to 0° C. under nitrogen. 4M HCl in dioxane (49.1 ml, 197 mmol, 1 eq.) was then added dropwise over 15 minutes, maintaining the temperature below 20° C. A white precipitate formed. The reactor was then reconfigured for distillation, the jacket temperature was increased to 100° C., and distillation of solvent was carried out. Additional i-PrOAc (100 mL) was added during concentration, after >100 mL distillate had been collected. Distillation was continued until ~250 mL total distillate was collected, then a Dean-Stark trap was attached and reflux continued for 1 hour. No water was observed to collect. The reaction mixture was cooled to 20° C. and filtered under suction under nitrogen. The filtered solid was washed with i-PrOAc (100 mL), dried under suction in nitrogen, then transferred to a glass dish and dried in a vacuum oven at 40° C. with a nitrogen bleed. Compound (1S).HCl was obtained as a white solid (24.2 g, 82%).

Synthesis 4B:

To a glass lined 120 L reactor was charged LiAlH₄ pellets (2.5 kg 66 mol, 1.2 equiv.) and dry THF (60 L) and warmed to 30° C. To the resulting suspension was charged (S)-3,5,5-trimethylpyrrolidin-2-one (7.0 kg, 54 mol) in THF (25 L) over 2 hours while maintaining the reaction temperature at 30 to 40° C. After complete addition, the reaction temperature was increased to 60-63° C. and maintained overnight. The reaction mixture was cooled to 22° C. and sampled to check for completion, then cautiously quenched with the addition of EtOAc (1.0 L, 10 moles, 0.16 eq) followed by a mixture of THF (3.4 L) and water (2.5 kg, 2.0 eq) then followed by a mixture of water (1.75 kg) with 50% aqueous sodium hydroxide (750 g, 2 eq water with 1.4 eq sodium hydroxide relative to aluminum), followed by 7.5 L water (6 eq "Fieser" quench). After the addition was completed, the reaction mixture was cooled to room temperature, and the solid was removed by filtration and washed with THF (3×25 L). The filtrate and washings were combined and treated with 5.0 L (58 moles) of aqueous 37% HCl (1.05 equiv.) while maintaining the temperature below 30° C. The resultant solution was concentrated by vacuum distillation to a slurry in two equal part lots on the 20 L Buchi evaporator. Isopropanol (8 L) was charged and the solution reconcentrated to near dryness by vacuum distillation. Isopropanol (4 L) was added and the product slurried by warming to about 50° C. Distillation from Isopropanol continued until water content by KF is ≤0.1%. Methyl tertbutyl ether (6 L) was added and the slurry cooled to 2-5° C. The product was collected by filtration and rinsed with 12 L methyl tert-butyl ether and pulled dry with a strong nitrogen flow and further dried in a vacuum oven (55° C./300 torr/N₂ bleed) to afford (S)-2,2,4-trimethylpyrrolidine-HCl ((1S).HCl) as a white, crystalline solid (6.21 kg, 75% yield). ¹H NMR (400 MHz, DMSO-d6) δ 9.34 (s, 2H), 3.33 (dd, J=11.4, 8.4 Hz, 1H), 2.75 (dd, J=11.4, 8.6 Hz, 1H), 2.50-2.39 (m, 1H), 1.97 (dd, J=12.7, 7.7 Hz, 1H), 1.42 (s, 3H), 1.38 (dd, J=12.8, 10.1 Hz, 1H), 1.31 (s, 3H), 1.05 (d, J=6.6 Hz, 3H).

Synthesis 4C:

With efficient mechanical stirring, a suspension of LiAlH₄ pellets (100 g 2.65 mol; 1.35 eq.) in THF (1 L; 4 vol. eq.) warmed at a temperature from 20° C.-36° C. (heat of mixing). A solution of (S)-3,5,5-trimethylpyrrolidin-2-one (250 g; 1.97 mol) in THF (1 L; 4 vol. eq.) was added to the suspension over 30 min. while allowing the reaction temperature to rise to ~60° C. The reaction temperature was increased to near reflux (~68° C.) and maintained for about 16 h. The reaction mixture was cooled to below 40° C. and cautiously quenched with drop-wise addition of a saturated aqueous solution of Na₂SO₄ (209 mL) over 2 h. After the addition was completed, the reaction mixture was cooled to ambient temperature, diluted with i-PrOAc (1 L), and mixed thoroughly. The solid was removed by filtration (Celite pad) and washed with i-PrOAc (2×500 mL). With external cooling and N₂ blanket, the filtrate and washings were combined and treated with drop-wise addition of anhydrous 4 M HCl in dioxane (492 mL; 2.95 mol; 1 equiv.) while maintaining the temperature below 20° C. After the addition was completed (20 min), the resultant suspension was concentrated by heating at reflux (74-85° C.) and removing the distillate. The suspension was backfilled with i-PrOAc (1 L) during concentration. After about 2.5 L of distillate was collected, a Dean-Stark trap was attached and any residual water was azeotropically removed. The suspension was cooled to below 30° C. when the solid was collected by filtration under a N₂ blanket. The solid is dried under N₂ suction and further dried in a vacuum oven (55° C./300 torr/N₂ bleed) to afford 261 g (89% yield) of (S)-2,2,4-trimethylpyrrolidine-HCl ((1S).HCl) as a white, crystalline solid. ¹H NMR (400 MHz, DMSO-d6) δ 9.34 (s, 2H), 3.33 (dd, J=11.4, 8.4 Hz, 1H), 2.75 (dd, J=11.4, 8.6 Hz, 1H), 2.50-2.39 (m, 1H), 1.97 (dd, J=12.7, 7.7 Hz, 1H), 1.42 (s, 3H), 1.38 (dd, J=12.8, 10.1 Hz, 1H), 1.31 (s, 3H), 1.05 (d, J=6.6 Hz, 3H). ¹H NMR (400 MHz, CDCl₃) δ 9.55 (d, J=44.9 Hz, 2H), 3.52 (ddt, J=12.1, 8.7, 4.3 Hz, 1H), 2.94 (dq, J=11.9, 5.9 Hz, 1H), 2.70-2.51 (m, 1H), 2.02 (dd, J=13.0, 7.5 Hz, 1H), 1.62 (s, 3H), 1.58-1.47 (m, 4H), 1.15 (d, J=6.7 Hz, 3H).

Synthesis 4D:

A 1 L four-neck round bottom flask was degassed three times. A 2M solution of LiAlH₄ in THF (100 mL) was charged via cannula transfer. (S)-3,5,5-trimethylpyrrolidin-2-one (19.0 g) in THF (150 mL) was added dropwise via an addition funnel over 1.5 hours at 50-60° C., washing in with THF (19 mL). Upon completion of the addition, the reaction was stirred at 60° C. for 8 hours and allowed to cool to room temperature overnight. GC analysis showed <1% starting material remained. Deionized water (7.6 mL) was added slowly to the reaction flask at 10-15° C., followed by 15% potassium hydroxide (7.6 mL). Isopropyl acetate (76 mL) was added, the mixture was stirred for 15 minutes and filtered, washing through with isopropyl acetate (76 mL). The filtrate was charged to a clean and dry 500 mL four neck round bottom flask and cooled to 0-5° C. 36% Hydrochloric acid (15.1 g, 1.0 eq.) was added keeping the temperature below 20° C. Distillation of the solvent, backfilling with isopropyl acetate (190 mL), was carried out to leave a residual volume of ~85 mL. Karl Fischer analysis=0.11% w/w H₂O. MTBE (methyl tertiary butyl ether) (19 mL) was added at 20-30° C. and the solids were filtered off under nitrogen at 15-20° C., washing with isopropyl acetate (25 mL) and drying under vacuum at 40-45° C. to give crude (S)-2,2,4-trimethylpyrrolidine hydrochloride as a white crystalline solid (17.4 g, 78% yield). GC purity=99.5%. Water content=0.20% w/w. Chiral GC gave an ee of 99.0% (S). Ruthenium content=0.004 ppm. Lithium content=0.07 ppm. A portion of the dried crude S)-2,2,4-trimethylpyrrolidine hydrochloride (14.3 g) was charged to a clean and dry 250 mL four-neck round bottom flask with isopropanol (14.3 mL) and the mixture held at 80-85° C. (reflux) for 1 hour to give a clear solution. The solution was allowed to cool to 50° C. (solids precipitated on cooling) then MTBE (43 mL) was added and the suspension held at 50-55° C. (reflux) for 3 hours. The solids were filtered off at 10° C., washing with MTBE (14 mL) and dried under vacuum at 40° C. to give recrystallised (S)-2,2,4-trimethylpyrrolidine hydrochloride ((1S).HCl) as a white crystallised solid (13.5 g, 94% yield on recrystallisation, 73% yield). GC purity=99.9%. Water content=0.11% w/w. 99.6% ee (Chiral GC) (S). Ruthenium content=0.001 ppm. Lithium content=0.02 ppm.

Synthesis 4E:

A reactor was charged with lithium aluminum hydride (LAH) (1.20 equiv.) and 2-MeTHF (2-methyltetrahydrofuran) (4.0 vol), and heated to internal temperature of 60° C. while stirring to disperse the LAH. A solution of (S)-3,5,5-trimethylpyrrolidin-2-one (1.0 equiv) in 2-MeTHF (6.0 vol) was prepared and stirred at 25° C. to fully dissolve the (S)-3,5,5-trimethylpyrrolidin-2-one. The (S)-3,5,5-trimethylpyrrolidin-2-one solution was added slowly to the reactor while keeping the off-gassing manageable, followed by rinsing the addition funnel with 2-MeTHF (1.0 vol) and adding it to the reactor. The reaction was stirred at an internal temperature of 60±5° C. for no longer than 6 h. The internal temperature was set to 5±5° C. and the agitation rate was increased. A solution of water (1.35 equiv.) in 2-MeTHF (4.0 v) was prepared and added slowly to the reactor while the internal temperature was maintained at or below 25° C. Additional water (1.35 equiv.) was charged slowly to the reactor while the internal temperature was maintained at or below 25° C. Potassium hydroxide (0.16 equiv.) in water (0.40 vol) was added to the reactor over no less than 20 min while the temperature was maintained at or below 25° C. The resulting solids were removed by filtration, and the reactor and cake were washed with 2-MeTHF (2×2.5 vol). The filtrate was transferred back to a jacketed vessel, agitated, and the temperature was adjusted to 15±5° C. Concentrated aqueous HCl (35-37%, 1.05 equiv.) was added slowly to the filtrate while maintaining the temperature at or below 25° C. and was stirred no less than 30 min. Vacuum was applied and the solution was distilled down to a total of 4.0 volumes while maintaining the internal temperature at or below 55° C., then 2-MeTHF (6.00 vol) was added to the vessel. The distillation was repeated until Karl Fischer analysis (KF)<0.20% w/w H₂O. Isopropanol was added (3.00 vol), and the temperature was adjusted to 70° C. (65-75° C.) to achieve a homogenous solution, and stirred for no less than 30 minutes at 70° C. The solution was cooled to 50° C. (47-53° C.) over 1 hour and stirred for no less than 1 h, while the temperature was maintained at 50° C. (47-53° C.). The resulting slurry was cooled to −10° C. (−15 to −5° C.) linearly over no less than 12 h. The slurry was stirred at −10° C. for no less than 2 h. The solids were isolated via filtration or centrifugation and were washed with a solution of 2-MeTHF (2.25 vol) and IPA (isopropanol) (0.75 vol). The solids were dried under vacuum at 45±5° C. for not less than 6 h to yield (S)-2,2,4-trimethylpyrrolidine hydrochloride ((1S).HCl).

Example 5: Phase Transfer Catalyst (PTC) Screens for the Synthesis of 5,5-dimethyl-3-methylenepyrrolidin-2-one Various PTCs were tested as described below:

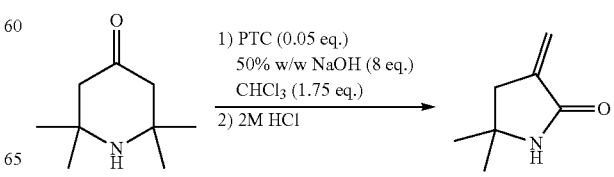

2,2,6,6-tetramethylpiperidin-4-one (500.0 mg, 3.06 mmol, 1.0 eq.), PTC (0.05 eq.), and chloroform (0.64 g, 0.4 mL, 5.36 mmol, 1.75 eq.) were charged into a vial equipped with a magnetic stir bar. The vial was cooled in an ice bath and a solution of 50 wt % sodium hydroxide (0.98 g, 24.48 mmol, 8.0 eq.) was added dropwise over 2 min. The reaction mixture was stirred until completion as assessed by GC analysis. The reaction mixture was diluted with DCM (2.0 mL, 4.0 v) and H$_2$O (3.0 mL, 6.0 v). The phases were separated and the aqueous phase was extracted with DCM (1.0 mL, 2.0 v). The organic phases were combined and 2M hydrochloric acid (0.17 g, 2.3 mL, 4.59 mmol, 1.5 eq.) was added. The reaction mixture was stirred until completion and assessed by HPLC. The aqueous phase was saturated with NaCl and the phases were separated. The aqueous phase was extracted with DCM (1.0 mL, 2.0 v) twice, the organic phases were combined, and 50 mg of biphenyl in 2 mL of MeCN was added as an internal HPLC standard. Solution yield was assessed by HPLC. The reaction results are summarized in the following table:

| Reactions | Conditions | Result |
|---|---|---|
| 5A | 18-crown-6 (0.05 eq.) | Complete in 2 h, 75% solution yield |
| 5B | TBAB (0.05 eq.) | Complete in 2 h, 83% solution yield |
| 5C | TBAC (0.05 eq.) | Complete in 4 h, 67% solution yield |
| 5D | Tetrabutylammonium hydroxide (0.05 eq.) | Complete in 4 h, 74% solution yield |
| 5E | 15-crown-5 (0.05 eq.) | Complete in 4 h, 78% solution yield |
| 5F | No PTC | Incomplete after 4 days |
| 5G | benzyltrimethylammonium chloride (0.05 eq.) | Complete in 7 h, 72% solution yield |
| 5H | Triton B (0.05 eq.) | Almost complete in 7 h (1% starting material leftover), 69% solution yield |
| 5I | Tributylmethylammonium chloride (0.05 eq.) | Complete in 4 h, 75% solution yield |
| 5J | Aliquat 336 (0.05 eq.) | Complete in 6 h, 76% solution yield |

Example 6: Solvent Screens for the Synthesis of 5,5-dimethyl-3-methylenepyrrolidin-2-one Various solvents and amounts were tested as described below:

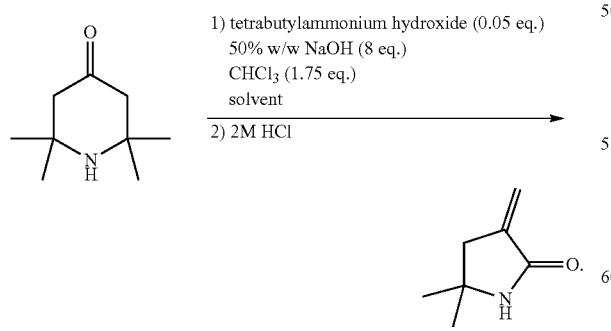

2,2,6,6-tetramethylpiperidin-4-one (500.0 mg, 3.06 mmol, 1.0 eq. ("starting material")), tetrabutylammonium hydroxide (0.12 g, 0.153 mmol, 0.050 eq), chloroform (0.64 g, 0.4 mL, 5.36 mmol, 1.75 eq.), and solvent (2 v or 4 v, as shown below) were charged into a vial equipped with a magnetic stir bar. The vial was cooled in an ice bath and a solution of 50 wt % sodium hydroxide (0.98 g, 24.48 mmol, 8.0 eq.) was added drop wise over 2 min. The reaction mixture was stirred until completion and assessed by GC analysis. The reaction mixture was diluted with DCM (2.0 mL, 4.0 v) and H$_2$O (3.0 mL, 6.0 v). The phases were separated and the aqueous phase was extracted with DCM (1.0 mL, 2.0 v). The organic phases were combined and 2 M hydrochloric acid (0.17 g, 2.3 mL, 4.59 mmol, 1.5 eq.) was added. The reaction mixture was stirred until completion, assessed by HPLC. The aqueous phase was saturated with NaCl and the phases were separated. The aqueous phase was extracted with DCM (1.0 mL, 2.0 v) twice, the organic phases were combined, and 50 mg of biphenyl in 2 mL of MeCN was added as an internal HPLC standard. Solution yield was assessed by HPLC. Reaction results are summarized in the following table:

| Reactions | Solvent | Result |
|---|---|---|
| 6A | CHCl$_3$ (4 vol.) | Complete overnight, 59% solution yield |
| 6B | DCM (4 vol.) | Incomplete overnight |
| 6C | CHCl$_3$ (2 vol.) | Complete in 6.5 h, 67% solution yield |
| 6D | THF (4 vol.) | Incomplete overnight |
| 6E | trifluorotoluene (4 vol.) | Incomplete overnight |
| 6F | NMP (N-methyl pyrrolidone) (4 vol.) | Incomplete overnight |
| 6G | DCM (2 vol.) | Complete overnight, 79% solution yield |
| 6H | THF (2 vol.) | Almost complete overnight (3% starting material), 66% solution yield |
| 6I | trifluorotoluene (2 vol.) | Almost complete overnight (1% starting material), 77% solution yield |
| 6J | heptane (2 vol.) | Almost complete at 6 h (5% starting material), complete over the weekend, 72% solution yield |

Example 7: Base Screens for the Synthesis of 5,5-dimethyl-3-methylenepyrrolidin-2-one In this experiment, various concentrations of NaOH were tested as described below:

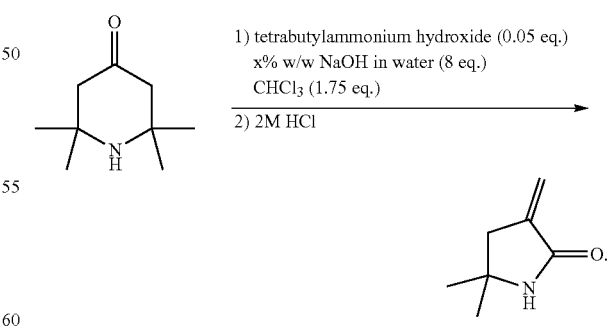

2,2,6,6-tetramethylpiperidin-4-one (500.0 mg, 3.06 mmol, 1.0 eq. ("starting material"), tetrabutylammonium hydroxide (0.12 g, 0.153 mmol, 0.050 eq), and chloroform (0.64 g, 0.4 mL, 5.36 mmol, 1.75 eq.) were charged into a vial equipped with a magnetic stir bar. The vial was cooled in an ice bath, and a solution of an amount wt % sodium hydroxide as shown in the Table below in water (0.98 g, 24.48 mmol, 8.0 eq.) was added drop wise over 2 min. The reaction mixture was stirred until completion and assessed by GC analysis. The reaction mixture was diluted with DCM (2.0 mL, 4.0 v) and H$_2$O (3.0 mL, 6.0 v). The phases were separated and the aqueous phase is extracted with DCM (1.0 mL, 2.0 v). The organic phases were combined and 2 M hydrochloric acid (0.17 g, 2.3 mL, 4.59 mmol, 1.5 eq.) was added. The reaction mixture was stirred until completion, assessed by HPLC. The aqueous phase was saturated with NaCl and the phases were separated. The aqueous phase was extracted with DCM (1.0 mL, 2.0 v) twice, the organic phases were combined, and 50 mg of biphenyl in 2 mL of MeCN was added as an internal HPLC standard. Solution yield was assessed by HPLC. Reaction results are summarized in the following table:

| Reactions | Conditions | Result |
| --- | --- | --- |
| 7A | 50 wt % NaOH (8 eq.) | Almost complete overnight (3% starting material), 81% solution yield |
| 7B | 40 wt % NaOH (8 eq.) | Incomplete overnight (9% starting material), 73% solution yield |
| 7C | 30 wt % NaOH (8 eq.) | Incomplete overnight |
| 7D | solid NaOH (8 eq.) 10 µL water | Complete in 2 h, 38% solution yield |

Example 8: Phase Transfer Catalyst (PTC) Synthesis of 5,5-dimethyl-3-methylenepyrrolidin-2-one Various amounts of PTCs were tested as described below: Tetrabutylammonium hydroxide (0.01 eq.), TBAB (0.01 eq.), Tributylmethylammonium chloride (0.01 eq.), Tetrabutylammonium hydroxide (0.02 eq.), TBAB (0.02 eq.), Tributylmethylammonium chloride (0.02 eq.), Tetrabutylammonium hydroxide (0.03 eq.), TBAB (0.03 eq.), Tributylmethylammonium chloride (0.03 eq.).

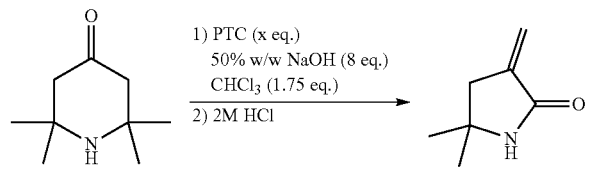

2,2,6,6-tetramethylpiperidin-4-one (500.0 mg, 3.06 mmol, 1.0 eq. ("starting material")), PTC (0.12 g, 0.153 mmol, 0.050 eq), and chloroform (1.75 eq.) were charged into a vial equipped with a magnetic stir bar. The vial was cooled in an ice bath, and a solution of 50 wt % sodium hydroxide (0.98 g, 24.48 mmol, 8.0 eq.) was added drop wise over 2 min. The reaction mixture was stirred until completion, assessed by GC analysis. The reaction mixture was diluted with DCM (2.0 mL, 4.0 v) and H$_2$O (3.0 mL, 6.0 v). The phases were separated and the aqueous phase was extracted with DCM (1.0 mL, 2.0 v). The organic phases were combined and 2 M hydrochloric acid (0.17 g, 2.3 mL, 4.59 mmol, 1.5 eq.) was added. The reaction mixture was stirred until completion, assessed by HPLC. The aqueous phase was saturated with NaCl and the phases were separated. The aqueous phase was extracted with DCM (1.0 mL, 2.0 v) twice, the organic phases were combined, and 50 mg of biphenyl in 2 mL of MeCN was added as an internal HPLC standard. Solution yield was assessed by HPLC. The reaction results are summarized in the following table:

| Reactions | Conditions | Result |
| --- | --- | --- |
| 8A | Tetrabutylammonium hydroxide (0.01 eq.) | Slow, incomplete over the weekend |
| 8B | TBAB (0.01 eq.) | Slow, incomplete over the weekend |
| 8C | Tributylmethylammonium chloride (0.01 eq.) | Incomplete over 2 days |
| 8D | Tetrabutylammonium hydroxide (0.02 eq.) | Almost complete overnight (2% starting material), 82% solution yield |
| 8E | TBAB (0.02 eq.) | Almost complete overnight (2% starting material), 71% solution yield |
| 8F | Tributylmethylammonium chloride (0.02 eq.) | Incomplete overnight (4% starting material), 72% solution yield |
| 8G | Tetrabutylammonium hydroxide (0.03 eq.) | Almost complete overnight (3% starting material), 76% solution yield |
| 8H | TBAB (0.03 eq.) | Almost complete overnight (3% starting material), 76% solution yield |
| 8I | Tributylmethylammonium chloride (0.03 eq.) | Almost complete overnight (2% starting material), 78% solution yield |

Example 9. Preparation of 2,2,6,6-tetramethylpiperidin-4-one hydrochloride

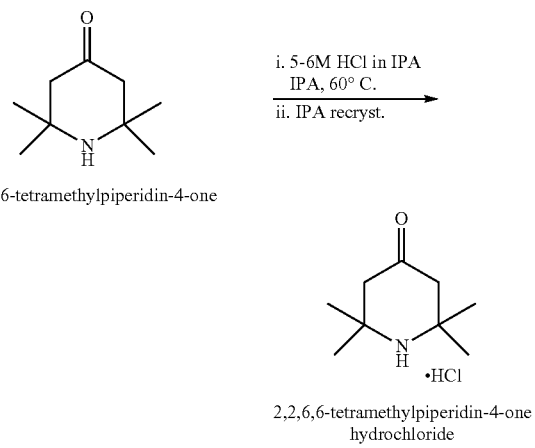

2,2,6,6-tetramethyl-4-piperidinone (30 g, 193.2 mmol, 1.0 eq) was charged to a 500 mL nitrogen purged three necked round bottomed flask equipped with condenser. IPA (300 mL, 10 vol) was added to the flask and the mixture heated to 60° C. until dissolved.

To the solution at 60° C. was added 5-6 M HCl in IPA (40 mL, 214.7 mmol, 1.1 eq) over 10 min and the resulting suspension stirred at 60° C. for 30 min then allowed to cool to ambient temperature. The suspension was stirred at ambient temperature overnight, then filtered under vacuum and washed with IPA (3×60 mL, 3×2 vol). The cream colored solid was dried on the filter under vacuum for 10 min.

The wet cake was charged to a 1 L nitrogen purged three necked round bottomed flask equipped with condenser. IPA (450 mL, 15 vol) was added to the flask and the suspension heated to 80° C. until dissolved. The mixture was allowed to cool slowly to ambient temperature over 3 h and the resulting suspension stirred overnight at ambient temperature.

The suspension was filtered under vacuum, washed with IPA (60 mL, 2 vol) and dried on the filter under vacuum for 30 min. The resulting product was dried in a vacuum oven at 40° C. over the weekend to give a white crystalline solid, 21.4 g, 64% yield.

Example 10. Synthesis of (S)-2,2,4-trimethylpyrrolidine hydrochloride from (S)-3,5,5-trimethyl-pyrrolidin-2-one

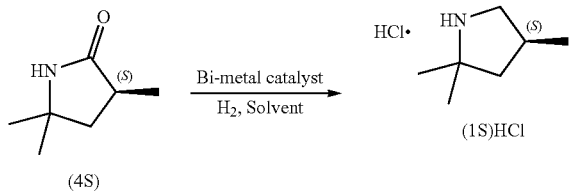

Each reactor was charged with (S)-3,5,5-trimethyl-pyrrolidin-2-one in THF, H$_2$, and the catalyst shown in the below table. The reactor was heated to 200° C. and pressurized to 60 bar, and allowed to react for 12 hours. GC analysis showed that (S)-2,2,4-trimethylpyrrolidine was produced in the columns denoted by "+."

| Catalyst | Product obtained (+) |
|---|---|
| 4% Pt—2% Re/TiO$_2$ | + |
| 4% Rh—2% Re/TiO$_2$ | + |
| 4% Rh/TiO$_2$ | + |
| 4% Pd/TiO$_2$ | + |
| 4% Pt/TiO$_2$ | + |
| 4% Pt—2% Sn/TiO$_2$ | + |
| 4% Pt—2% Co/TiO$_2$ | + |

A 2.5% solution of (S)-3,5,5-trimethyl-pyrrolidin-2-one in THF was flowed at 0.05 mL/min into a packed bed reactor prepacked with 2% Pt-0.5% Sn/SiO$_2$ catalyst immobilized on silica gel. H$_2$ gas was also flowed into the packed bed reactor at 20 mL/min. The reaction was carried out at 130° C. under 80 bar pressure with a WHSV (Weigh Hourly Space Velocity) of 0.01-0.02 h$^{-1}$. The product feed was collected in a batch tank and converted to (S)-2,2,4-trimethylpyrrolidine HCl in batch mode: 36% Hydrochloric acid (1.1 eq.) was added keeping the temperature below 20° C. Distillation of the solvent, backfilling with isopropyl acetate (4 v), was carried out to leave a residual volume of 5 v. Karl Fischer analysis <0.2% w/w H$_2$O. MTBE (methyl tertiary butyl ether) (1 v) was added at 20-30° C. and the solids were filtered off under nitrogen at 15-20° C., washing with isopropyl acetate (1.5 v) and drying under vacuum at 40-45° C. to give (S)-2,2,4-trimethylpyrrolidine hydrochloride as a white crystalline solid (74.8% yield, 96.1% ee).

Alternate Synthesis

A 2.5% solution of (S)-3,5,5-trimethyl-pyrrolidin-2-one in THF was flowed at 0.05 mL/min into a packed bed reactor prepacked with 4% Pt-2% Sn/TiO$_2$ catalyst immobilized on silica gel. H$_2$ gas was also flowed into the packed bed reactor at 20 mL/min. The reaction was carried out at 200° C. under 50 bar pressure with a WHSV (Weigh Hourly Space Velocity) of 0.01-0.02 h$^{-1}$. The product feed was collected in a batch tank and converted to (S)-2,2,4-trimethylpyrrolidine HCl in batch mode: 36% Hydrochloric acid (1.1 eq.) was added keeping the temperature below 20° C. Distillation of the solvent, backfilling with isopropyl acetate (4 v), was carried out to leave a residual volume of 5 v. Karl Fischer analysis <0.2% w/w H$_2$O. MTBE (methyl tertiary butyl ether) (1 v) was added at 20-30° C. and the solids were filtered off under nitrogen at 15-20° C., washing with isopropyl acetate (1.5 v) and drying under vacuum at 40-45° C. to give (S)-2,2,4-trimethylpyrrolidine hydrochloride as a white crystalline solid (88.5% yield, 29.6% ee).

Alternate Synthesis

A 2.5% solution of (S)-3,5,5-trimethyl-pyrrolidin-2-one in THF was flowed at 0.05 mL/min into a packed bed reactor prepacked with 2% Pt-0.5% Sn/TiO$_2$ catalyst immobilized on silica gel. H$_2$ gas was also flowed into the packed bed reactor at 20 mL/min. The reaction was carried out at 150° C. under 50 bar pressure with a WHSV (Weigh Hourly Space Velocity) of 0.01-0.02 h$^{1}$. The product feed was collected in a batch tank and converted to (S)-2,2,4-trimethylpyrrolidine HCl in batch mode: 36% Hydrochloric acid (1.1 eq.) was added keeping the temperature below 20° C. Distillation of the solvent, backfilling with isopropyl acetate (4 v), was carried out to leave a residual volume of 5 v. Karl Fischer analysis <0.2% w/w H$_2$O. MTBE (methyl tertiary butyl ether) (1 v) was added at 20-30° C. and the solids were filtered off under nitrogen at 15-20° C., washing with isopropyl acetate (1.5 v) and drying under vacuum at 40-45° C. to give (S)-2,2,4-trimethylpyrrolidine hydrochloride as a white crystalline solid (90.9% yield, 98.0% ee).

Alternate Synthesis

A 2.5% solution of (S)-3,5,5-trimethyl-pyrrolidin-2-one in THF was flowed at 0.03 mL/min into a packed bed reactor prepacked with 2% Pt-8% Sn/TiO$_2$ catalyst immobilized on silica gel. H$_2$ gas was also flowed into the packed bed reactor at 40 mL/min. The reaction was carried out at 180° C. under 55 bar pressure with a residence time of 6 min. The product feed was collected in a batch tank and converted to (S)-2,2,4-trimethylpyrrolidine HCl in batch mode: 36% Hydrochloric acid (1.1 eq.) was added keeping the temperature below 20° C. Distillation of the solvent, backfilling with isopropyl acetate (4 v), was carried out to leave a residual volume of 5 v. Karl Fischer analysis <0.2% w/w H$_2$O. MTBE (methyl tertiary butyl ether) (1 v) was added at 20-30° C. and the solids were filtered off under nitrogen at 15-20° C., washing with isopropyl acetate (1.5 v) and drying under vacuum at 40-45° C. to give (S)-2,2,4-trimethylpyrrolidine hydrochloride as a white crystalline solid (90.4% yield, 96.8% ee).

The invention claimed is:

1. A process for preparing (S)-2,2,4-trimethylpyrrolidine or a salt thereof comprising:
    (a) reacting 2,2,6,6-tetramethyl-piperidin-4-one or a salt thereof with chloroform and at least one base;
    (b) reacting the products of the reaction in (a) with an acid to produce 5,5-dimethyl-3-methylenepyrrolidin-2-one;
    (c) hydrogenating 5,5-dimethyl-3-methylenepyrrolidin-2-one to produce (S)-3,5,5-trimethyl-pyrrolidin-2-one;
    (d) reducing (S)-3,5,5-trimethyl-pyrrolidin-2-one to produce (S)-2,2,4-trimethylpyrrolidine; and
    (e) optionally treating (S)-2,2,4-trimethylpyrrolidine with acid to produce a salt of (S)-2,2,4-trimethylpyrrolidine.

2. A process for preparing (R)-2,2,4-trimethylpyrrolidine or a salt thereof comprising:
    (a) reacting 2,2,6,6-tetramethyl-piperidin-4-one or a salt thereof with chloroform and at least one base;

(b) reacting the products of the reaction in (a) with an acid to produce 5,5-dimethyl-3-methylenepyrrolidin-2-one;
(c) hydrogenating 5,5-dimethyl-3-methylenepyrrolidin-2-one to produce (R)-3,5,5-trimethyl-pyrrolidin-2-one;
(d) reducing (R)-3,5,5-trimethyl-pyrrolidin-2-one to produce (R)-2,2,4-trimethylpyrrolidine; and
(e) optionally treating (R)-2,2,4-trimethylpyrrolidine with acid to produce a salt of (R)-2,2,4-trimethylpyrrolidine.

3. A process for preparing (S)-3,5,5-trimethylpyrrolidin-2-one comprising:
(a) reacting 2,2,6,6-tetramethyl-piperidin-4-one or a salt thereof with chloroform and at least one base;
(b) reacting the products of the reaction in (a) with an acid to produce 5,5-dimethyl-3-methylenepyrrolidin-2-one; and
(c) hydrogenating 5,5-dimethyl-3-methylenepyrrolidin-2-one to produce (S)-3,5,5-trimethyl-pyrrolidin-2-one.

4. A process for preparing (R)-3,5,5-trimethylpyrrolidin-2-one comprising:
(a) reacting 2,2,6,6-tetramethyl-piperidin-4-one or a salt thereof with chloroform and at least one base;
(b) reacting the products of the reaction in (a) with an acid to produce 5,5-dimethyl-3-methylenepyrrolidin-2-one; and
(c) hydrogenating 5,5-dimethyl-3-methylenepyrrolidin-2-one to produce (R)-3,5,5-trimethyl-pyrrolidin-2-one.

5. A process for preparing 5,5-dimethyl-3-methylenepyrrolidin-2-one comprising:
(a) reacting 2,2,6,6-tetramethyl-piperidin-4-one or a salt thereof with chloroform and at least one base; and
(b) reacting the products of the reaction in (a) with an acid to produce 5,5-dimethyl-3-methylenepyrrolidin-2-one.

6. The process according to claim 1, further comprising treating (S)-2,2,4-trimethylpyrrolidine with HCl to generate (S)-2,2,4-trimethylpyrrolidine hydrochloride.

7. The process according to claim 1 or 3, wherein the at least one base is chosen from potassium t-butoxide, potassium hydroxide, and sodium hydroxide.

8. The process according to claim 7, wherein the at least one base is sodium hydroxide.

9. The process according to claim 1 or 3, wherein the at least one base added for the reaction in (a) is in the form of an aqueous solution having a concentration ranging from 20 wt % to 80 wt % relative to the total weight of the aqueous solution.

10. The process according to claim 1 or 3, wherein the 2,2,6,6-tetramethyl-piperidin-4-one or a salt thereof is reacted with chloroform, at least one base, and at least one phase transfer catalyst.

11. The process according to claim 10, wherein the at least one phase transfer catalyst is chosen from tetraalkylammonium salts and crown ethers.

12. The process according to claim 10, wherein the at least one phase transfer catalyst is chosen from tetraalkylammonium halides.

13. The process according to claim 10, wherein the at least one phase transfer catalyst is chosen from tributylmethylammonium chloride, tributylmethylammonium bromide, tetrabutylammonium bromide (TBAB), tetrabutylammonium chloride (TBAC), tetrabutylammonium iodide (TBAI), tetrabutylammonium hydroxide (TBAH), benzyltrimethylammonium chloride, tetraoctylammonium bromide (TOAB), tetraoctylammonium chloride (TOAC), tetraoctylammonium iodide (TOAI), trioctylmethylammonium chloride, and trioctylmethylammonium bromide.

14. The process according to claim 1 or 3, wherein the acid of the reaction in (b) is chosen from aqueous solutions of protic acids.

15. The process according to claim 14, wherein the protic acids are chosen from hydrochloric acid, methane sulfonic acid, triflic acid, and sulfuric acid.

16. The process according to claim 1 or 3, wherein the hydrogenating reaction in (c) comprises reacting 5,5-dimethyl-3-methylenepyrrolidin-2-one with at least one catalyst and hydrogen gas to produce (S)-3,5,5-trimethyl-pyrrolidin-2-one.

17. The process according to claim 16, wherein the at least one catalyst is chosen from ruthenium hydrogenation catalysts, rhodium hydrogenation catalysts, and iridium hydrogenation catalysts.

18. The process according to claim 1, wherein the reducing reaction in (d) comprises reacting (S)-3,5,5-trimethyl-pyrrolidin-2-one with a hydride to produce (S)-2,2,4-trimethylpyrrolidine.

19. The process according to claim 18, wherein the hydride is chosen from lithium aluminum hydride, sodium bis(2-methoxyethoxy)aluminumhydride, and borane.

20. The process according to claim 1 or 3, wherein 2,2,6,6-tetramethyl-piperidin-4-one or a salt thereof is reacted with chloroform, at least one base, and in the presence of at least one solvent.

21. The process according to claim 20, wherein the at least one solvent is chosen from organic solvents.

22. The process according to claim 21, wherein the at least one solvent is chosen from dichloromethane, heptane, chloroform, trifluorotoluene, tetrahydrofuran (THF), and N-methylpyrrolidone (NMP).

* * * * *